(12) United States Patent
Buyse et al.

(10) Patent No.: US 9,745,372 B2
(45) Date of Patent: Aug. 29, 2017

(54) TNF BINDERS

(71) Applicant: Ablynx N.V., Zwijnaarde (BE)

(72) Inventors: Marie-Ange Buyse, Merelbeke (BE); Joachim Boucneau, De Pinte (BE); Peter Casteels, Erpe-Mere (BE); Gino Van Heeke, Eine (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 0 days.

(21) Appl. No.: 15/456,824

(22) Filed: Mar. 13, 2017

(65) Prior Publication Data

US 2017/0190769 A1    Jul. 6, 2017

Related U.S. Application Data

(63) Continuation of application No. 15/501,011, filed as application No. PCT/EP2016/077595 on Nov. 14, 2016.

(60) Provisional application No. 62/254,375, filed on Nov. 12, 2015.

(51) Int. Cl.
A61K 39/395    (2006.01)
C07K 16/24    (2006.01)

(52) U.S. Cl.
CPC ........ C07K 16/241 (2013.01); C07K 2317/24 (2013.01); C07K 2317/569 (2013.01); C07K 2317/94 (2013.01)

(58) Field of Classification Search
None
See application file for complete search history.

(56) References Cited

FOREIGN PATENT DOCUMENTS

| WO | WO 2004/041862 A2 | 5/2004 |
|---|---|---|
| WO | WO 2006/122786 A2 | 11/2006 |
| WO | WO 2006/122787 A1 | 11/2006 |
| WO | WO 2007/025977 A2 | 3/2007 |
| WO | WO 2012/175741 A2 | 12/2012 |
| WO | WO 2013/024059 A2 | 2/2013 |
| WO | WO 2015/173325 A2 | 11/2015 |

OTHER PUBLICATIONS

Amiot et al., Current, new and future biological agents on the horizon for the treatment of inflammatory bowel diseases. Therap Adv Gastroenterol. Mar. 2015;8(2):66-82. doi: 10.1177/1756283X14558193.
Dumoulin et al., Single-domain antibody fragments with high conformational stability. Protein Sci. Mar. 2002;11(3):500-15.
Harmsen et al., Selection and optimization of proteolytically stable llama single-domain antibody fragments for oral immunotherapy. Appl Microbiol Biotechnol. Sep. 2006;72(3):544-51.
Holland et al., Autoantibodies to variable heavy (VH) chain Ig sequences in humans impact the safety and clinical pharmacology of a VH domain antibody antagonist of TNF-[alpha] receptor 1. J Clin Immunol. Jul. 6, 2013;33(7):1192-1203.
Hussack et al., Characterization of single-domain antibodies with an engineered disulfide bond. Methods Mol Biol. 2012;911:417-29. doi:10.1007/978-1-61779-968-6_25.
Hussack et al., Neutralization of Clostridium difficile toxin A with single-domain antibodies targeting the cell receptor binding domain. J Biol Chem. Mar. 18, 2011;286(11):8961-76. doi: 10.1074/jbc.M110.198754.
MacCallum et al., Antibody-antigen interactions: contact analysis and binding site topography. J Mol Biology. Jan. 1, 1996;262(5):732-745.
Singh et al., Past, present, and future technologies for oral delivery of therapeutic proteins. J Pharm Sci. Jul. 2008;97(7):2497-523.

*Primary Examiner* — Zachary Skelding
(74) *Attorney, Agent, or Firm* — Wolf, Greenfield & Sacks, P.C.

(57) ABSTRACT

The present invention relates to amino acid sequences, compounds and polypeptides binding to tumor necrosis factor alpha ("TNF" or "TNF-alpha"). In particular, the present invention relates to improved heavy-chain immunoglobulin single variable domains (also referred to herein as "ISV's" or "ISVDs") binding to tumor necrosis factor alpha, as well as to proteins, polypeptides and other constructs, compounds, molecules or chemical entities that comprise such ISVDs, collectively TNF binders. Other aspects, embodiments, features, uses and advantages of the invention will be clear to the skilled person based on the disclosure herein.

2 Claims, 21 Drawing Sheets

Figure 1

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: http://www.bioc.uzh.ch/plueckthun/antibody/Numbering/NumFrame.html

Figure 2

```
                                10        20        30        40
                       ----:----|----:----|----:----|----:----|
SEQ ID NO: 58          QVQLVESGGGLVQAGGSLRLSCTASGQTSSTADMGWFRQP
SEQ ID NO:  1          E.............P.............F.F........A
SEQ ID NO: 59          E........V..P.............F.F........A 50        60        70        80
                       ----:----|--a--:----|----:----|----:----|
SEQ ID NO: 58          PGKGREFVARISGIDGTTYYDEPVKGRFTISRDKAQNTVYL
SEQ ID NO:  1          ........S........................N.K..L..
SEQ ID NO: 59          ........S........................N.K..L..

90       100       110
                       --abc--:----|----:----|abcd----:----|----
SEQ ID NO: 58          QMDSLKPEDTAVYYCRSPRYADQWSAYDYWGQGTQVTVSS-
SEQ ID NO:  1          ..N..R.......................L......-
SEQ ID NO: 59          ..N..R.....R.................L......-
```

Figure 3

| SEQ ID NO | Description | Sequence |
|---|---|---|
| 1 | reference A: | EVQLVESGGGLVQPGGSLRLSCTASGFTFSTADMGWFRQAPGKGREFVSRI SGIDGTTYYDEPVKGRFTISRDNAKNTLYLQMNSLRPEDTAVYYCRSPRYA DQWSAYDYWGQGTLVTVSS |
| 2 | CDR1 (Kabat) | TADMG |
| 3 | CDR2 (Kabat) | RISGIDGTTYYDEPVKG |
| 4 | CDR3 (Kabat/Abm) | PRYADQWSAYDY |
| 5 | CDR1 (Abm) | GFTFSTADMG |
| 6 | CDR2 (Abm) | RISGIDGTTY |
| 7 | CDR3 (Kabat/Abm) | PRYADQWSAYDY |
| 8 | Reference A (89T) | EVQLVESGGGLVQPGGSLRLSCTASGFTFSTADMGWFRQAPGKGREFVSRI SGIDGTTYYDEPVKGRFTISRDNAKNTLYLQMNSLRPEDTATYYCRSPRYA DQWSAYDYWGQGTLVTVSS |
| 9 | Reference A (11V + 110K) | EVQLVESGGGVVQPGGSLRLSCTASGFTFSTADMGWFRQAPGKGREFVSRI SGIDGTTYYDEPVKGRFTISRDNAKNTLYLQMNSLRPEDTAVYYCRSPRYA DQWSAYDYWGQGTLVKVSS |
| 10 | Reference A (11V + 110Q) | EVQLVESGGGVVQPGGSLRLSCTASGFTFSTADMGWFRQAPGKGREFVSRI SGIDGTTYYDEPVKGRFTISRDNAKNTLYLQMNSLRPEDTAVYYCRSPRYA DQWSAYDYWGQGTLVQVSS |
| 11 | Reference A (11V + 112K) | EVQLVESGGGVVQPGGSLRLSCTASGFTFSTADMGWFRQAPGKGREFVSRI SGIDGTTYYDEPVKGRFTISRDNAKNTLYLQMNSLRPEDTAVYYCRSPRYA DQWSAYDYWGQGTLVTVKS |
| 12 | Reference A (11V + 112Q) | EVQLVESGGGVVQPGGSLRLSCTASGFTFSTADMGWFRQAPGKGREFVSRI SGIDGTTYYDEPVKGRFTISRDNAKNTLYLQMNSLRPEDTAVYYCRSPRYA DQWSAYDYWGQGTLVTVQS |

Figure 3 (continued)

| SEQ ID NO | Description | Sequence |
|---|---|---|
| 13 | Reference A (89L + 110K) | EVQLVESGGGLVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVKVSS |
| 14 | Reference A (89L + 110Q) | EVQLVESGGGLVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVQVSS |
| 15 | Reference A (89L + 112K) | EVQLVESGGGLVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVTVKS |
| 16 | Reference A (89L + 112Q) | EVQLVESGGGLVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVTVQS |
| 17 | Reference A (11V + 89L) | EVQLVESGGGVVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVTVSS |
| 18 | Reference A (11V + 89L + 110K) | EVQLVESGGGVVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVKVSS |
| 19 | Reference A (11V + 89L + 110Q) | EVQLVESGGGVVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVQVSS |
| 20 | Reference A (11V + 89L + 112K) | EVQLVESGGGVVQPGGSLRLSCTASGFTFSTADMGWFRQAPGKGRE FVSRISGIDGTTYYDEPVKGRFTISRDNAKNTLYLQMNSLRPEDTA LYYCRSPRYADQWSAYDYWGQGTLVTVKS |

Figure 3 (continued)

| SEQ ID NO | Description | Sequence |
|---|---|---|
| 21 | Reference A (11V + 89L + 112Q) | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVQS |
| 22 | Reference A (89T)+ A | EVQLVESGGGLVQPGGSLRLSCTASGFTFSTADMGWFRQAPGKGREFVSRISGIDGTTYYDEPVKGRFTISRDNAKNTLYLQMNSLRPEDTATYYCRSPRYADQWSAYDYWGQGTLVTVSSA |
| 23 | Reference A (11V + 110K)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTAVYYCRSPRYADQWSAYDYWGQGTLVKVSSA |
| 24 | Reference A (11V + 110Q)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTAVYYCRSPRYADQWSAYDYWGQGTLVQVSSA |
| 25 | Reference A (11V + 112K)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTAVYYCRSPRYADQWSAYDYWGQGTLVTVKSA |
| 26 | Reference A (11V + 112Q)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTAVYYCRSPRYADQWSAYDYWGQGTLVTVQSA |
| 27 | Reference A (89L + 110K)+ A | EVQLVESGGGLVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVKVSSA |
| 28 | Reference A (89L + 110Q)+ A | EVQLVESGGGLVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVQVSSA |

Figure 3 (continued)

| SEQ ID NO | Description | Sequence |
|---|---|---|
| 29 | Reference A (89L + 112K)+A | EVQLVESGGGLVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVKSA |
| 30 | Reference A (89L + 112Q)+A | EVQLVESGGGLVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVQSA |
| 31 | Reference A (11V + 89L)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVSSA |
| 32 | Reference A (11V + 89L + 110K)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVKVSSA |
| 33 | Reference A (11V + 89L + 110Q)+ A | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVQVSSA |
| 34 | Reference A (11V + 89L + 112K)+A | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVKSA |
| 35 | Reference A (11V + 89L + 112Q)+A | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVQSA |
| 36 | TNF binder of the invention (00016) | DVQLVESGGGVVQPGGSLRLSCTASGFTFSTADMGWFRQAPGKGREFVARISGIDGTTYYDEPVKGRFTISRDNSKNTLYLQMNSLRPEDTALYYCRSPRYADQWSAYDYWGQGTLVTVSSA |
| 37 | TNF binder of the invention (00018) | DVQLVESGGGVVQPGGSLRLSCTASGFTFSTADMGWFRQAPGKGREFVSRISGIDGTTYYDEPVKGRFTISRDNSKNTLYLQMNSLRPEDTALYYCRSPRYADQWSAYDYWGQGTLVTVSSA |

Figure 3 (continued)

| SEQ ID NO | Description | Sequence |
|---|---|---|
| 38 | TNF binder of the invention (00019) | DVQLVESGGGVVQPGGSLRLSCTASGFTFSTADMGWFRQAPGKGREFVSRISGIDGTTYYDEPVKGRFTISRDNSKNTVYLQMNSLRPEDTALYYCRSPRYADQWSAYDYWGQGTLVTVSSA |
| 39 | TNF binder of the invention (00020) | DVQLVESGGGVVQPGGSLRLSCTASGFTFSTADMGWFRQAPGKGREFVARISGIDGTTYYADSVKGRFTISRDNSKNTVYLQMNSLRPEDTALYYCRSPRYADQWSAYDYWGQGTLVTVSSA |
| 40 | TNF binder of the invention (00021) | DVQLVESGGGVVQPGGSLRLSCTASGFTFSTADMGWFRQAPGKGREFVARISGIDGTTYYDEPVKGRFTISRDNSKNTVYLQMNSLRPEDTALYYCRSPRYADQWSAYDYWGQGTLVTVSSA |
| 41 | TNF binder of the invention (00030) | DVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVSSA |
| 42 | HIS6-FLAG3 tag | HHHHHHGAADYKDHDGDYKDHDIDYKDDDDKGAA |
| 43 | C-terminal end | VTVKS |
| 44 | C-terminal end | VTVQS |
| 45 | C-terminal end | VKVSS |
| 46 | C-terminal end | VQVSS |
| 47 | C-terminal end | VTVKSX(n) |
| 48 | C-terminal end | VTVQSX(n) |
| 49 | C-terminal end | VKVSSX(n) |
| 50 | C-terminal end | VQVSSX(n) |
| 51 | C-terminal end | VTVKSA |
| 52 | C-terminal end | VTVQSA |
| 53 | C-terminal end | VKVSSA |
| 54 | C-terminal end | VQVSSA |
| 55 | C-terminal end | VTVSS |
| 56 | C-terminal end | VTVSSX$_{(n)}$ |
| 57 | C-terminal end | VTVSSA |
| 58 | NC55TNF-NC7 (PMP6C11) WO2006/122786: SEQ ID NO: 125 | QVQLVESGGGLVQAGGSLRLSCTASGQTSSTADMGWFRQPPGKGREFVARISGIDGTTYYDEPVKGRFTISRDKAQNTVYLQMDSLKPEDTAVYYCRSPRYADQWSAYDYWGQGTQVTVSS |
| 59 | WO2015/173325 seq id NO: 345 | EVQLVESGGGVVQPGGSLRLSCTASGFTFSTADMGWFRQAPGKGREFVSRISGIDGTTYYDEPVKGRFTISRDNAKNTLYLQMNSLRPEDTALYYCRSPRYADQWSAYDYWGQGTLVTVSS |

Figure 3 (continued)

| 60 | TNF200 | DVQLVESGGGLVQPGGSLRLSCTASGFTFSTADMGWFRQAPGKGRE FVSRISGIDGTTYYDEPVKGRFTISRDNAKNTLYLQMNSLRPEDTA VYYCRSPRYADQWSAYDYWGQGTLVTVSS |
|---|---|---|
| 61 | A016600015 (TNF200A) | DVQLVESGGGLVQPGGSLRLSCTASGFTFSTADMGWFRQAPGKGRE FVSRISGIDGTTYYDEPVKGRFTISRDNAKNTLYLQMNSLRPEDTA VYYCRSPRYADQWSAYDYWGQGTLVTVSSA |
| 62 | A016600046 100dL (00046) | DVQLVESGGGVVQPGGSLRLSCTASGFTFSTADMGWFRQAPGKGRE FVARISGIDGTTYYDEPVKGRFTISRDNSKNTVYLQMNSLRPEDTA LYYCRSPRYADQWSALDYWGQGTLVTVSSA |
| 63 | A016600052 (49C-69C + 100dL (00052) | DVQLVESGGGVVQPGGSLRLSCTASGFTFSTADMGWFRQAPGKGRE FVCRISGIDGTTYYDEPVKGRFTCSRDNSKNTVYLQMNSLRPEDTA LYYCRSPRYADQWSALDYWGQGTLVTVSSA |
| 64 | A016600038 (00038) | DVQLVESGGGVVQPGGSLRLSCTASGFTFSTADMGWFRQAPGKGRE FVARISGIDGTTYYDEPVKGRFTISRDNAKNTVYLQMNSLRPEDTA LYYCRSPRYADQWSAYDYWGQGTLVTVSSA |
| 65 | A016600013 (00013) | EVQLVESGGGLVQPGGSLRLSCTASGFTFSTADMGWFLQAPGKGRE FVSRISGIDGTTYYDEPVQGRFTISRDNAKNTLYLQMNSLRPEDTA VYYCRPSQYADQWSAYDYWGQGTLVTVSS |
| 66 | A016600014 (00014) | EVQLVESGGGLVQPGGSLRLSCTASGFTFSTADMGWFRQAPGKGRE FVSRISGIDGTTYYDEPVQGRFTISRDNAKNTLYLQMNSLRPEDTA VYYCRPSQYADQWSAYDYWGQGTLVTVSS |
| 67 | A016600040 (00040) | QVQLVESGGGLVQAGGSLRLSCTASGQTSSTADMGWFRQPPGKGRE FVARISGIDGTTYYDEPVKGRFTISRDKAQNTVYLQMDSLKPEDTA VYYCRSPRYADQWSAYDYWGQGTQVTVSS |
| 68 | A016600039 (00039) | QVQLVESGGGLVQAGGSLRLSCTASGQTSSTADMGWFRQPPGKGRE FVARISGIDGTTYYDEPVKGRFTISRDKSQNTVYLQMDSLKPEDTA VYYCRSPRYADQWSAYDYWGQGTQVTVSS |
| 69 | A016600045 (00045) | DVQLVESGGGVVQPGGSLRLSCTASGFTFSTADMGWFRQAPGKGRE FVARISGIDGTTYYDEPVKGRFTISRDNSKNTVYLQMNSLRPEDTA LYYCRSPRYADQWSAHDYWGQGTLVTVSSA |

```
SEQIDNO:1    S -  121
SEQIDNO:8      -  121
SEQIDNO:9      -  121
SEQIDNO:11     -  121
SEQIDNO:10     -  121
SEQIDNO:12     -  121
SEQIDNO:13     -  121
SEQIDNO:14     -  121
SEQIDNO:15     -  121
SEQIDNO:16     -  121
SEQIDNO:17     -  121
SEQIDNO:18     -  121
SEQIDNO:19     -  121
SEQIDNO:20     -  121
SEQIDNO:21     -  121
SEQIDNO:22     A  122
SEQIDNO:23     A  122
SEQIDNO:24     A  122
SEQIDNO:25     A  122
SEQIDNO:26     A  122
SEQIDNO:27     A  122
SEQIDNO:28     A  122
SEQIDNO:29     A  122
SEQIDNO:30     A  122
SEQIDNO:31     A  122
SEQIDNO:32     A  122
SEQIDNO:33     A  122
SEQIDNO:34     A  122
SEQIDNO:35     A  122
SEQIDNO:36     A  122
SEQIDNO:37     A  122
SEQIDNO:38     A  122
SEQIDNO:39     A  122
SEQIDNO:40     A  122
SEQIDNO:41     A  122
SEQIDNO:58     -  121
```

Figure 5

| | | | | | | |
|---|---|---|---|---|---|---|
| SEQIDNO:31 | EVQLVESGGG | VVQPGGSLRL | SCTASGFTFS | TADMGWFRQA | PGKGREFVSR | ISGISGTTYY 60 |
| SEQIDNO:36 | D......... | .......... | .......... | .......... | .....A.... | ............ 60 |
| SEQIDNO:37 | D......... | .......... | .......... | .......... | .......... | ............ 60 |
| SEQIDNO:38 | S......... | .......... | .......... | .......... | .......... | ............ 60 |
| SEQIDNO:39 | S......... | .......... | .......... | .......... | .....A.... | ............ 60 |
| SEQIDNO:40 | D......... | .......... | .......... | .......... | .....A.... | ............ 60 |
| SEQIDNO:41 | S......... | .......... | .......... | .......... | .......... | ............ 60 |
| SEQIDNO:1 | .......... | .L........ | .......... | .......... | .......... | ............ 60 |

| | | | | | | |
|---|---|---|---|---|---|---|
| SEQIDNO:31 | DEPVKGRFTI | SRDNAKNTLY | LQMNSLRPED | TALYYCRSPR | YADQWSAYDY | WGQGTLVTVS 120 |
| SEQIDNO:36 | .......... | .....S.... | .......... | .......... | .......... | ............ 120 |
| SEQIDNO:37 | .......... | .....S.... | .......... | .......... | .......... | ............ 120 |
| SEQIDNO:38 | .......... | .....S...V. | .......... | .......... | .......... | ............ 120 |
| SEQIDNO:39 | ADS....... | .....S...V. | .......... | .......... | .......... | ............ 120 |
| SEQIDNO:40 | .......... | .....S...V. | .......... | .......... | .......... | ............ 120 |
| SEQIDNO:41 | .......... | .......... | .......... | .......... | .......... | ............ 120 |
| SEQIDNO:1 | .......... | .......... | .......... | ...V...... | .......... | ............ 120 |

SEQIDNO:31 SA 122
SEQIDNO:36 .. 122
SEQIDNO:37 .. 122
SEQIDNO:38 .. 122
SEQIDNO:39 .. 122
SEQIDNO:40 .. 122
SEQIDNO:41 .. 122
SEQIDNO:1 .- 121

Figure 7

| Sample | Normalized PreAb binding levels (RU at 125 s) | | | | | % Reduction PreAb binding compared to Reference A | | | |
|---|---|---|---|---|---|---|---|---|---|
| | SEQ ID NO:58 (Q108L) | Reference A | Reference A (L11V) | Reference A (L11V, A74S, V89L) | Reference A (L11V, S49A, V89L) | SEQ ID NO:58 (Q108L) | Reference A | Reference A (L11V, A74S, V89L) | Reference A (L11V, S49A, V89L) |
| IHuS#ABL-0042-02 | -15 | -11 | -20 | -23 | -15 | | | | |
| IHuS#ABL-0088-03 | 118 | 200 | 3 | -3 | 12 | 41 | 99 | 100 | 94 |
| IHuS#ABL-0137-01 | -17 | 8 | -16 | -22 | -14 | | | | |
| IHuS#ABL-0138-01 | -11 | 19 | -14 | -17 | -17 | | | | |
| IHuS#ABL-0139-01 | 0 | 37 | -9 | -12 | -11 | 100 | 100 | 100 | 100 |
| IHuS#ABL-0141-01 | -17 | -2 | -15 | -15 | -10 | | | | |
| IHuS#ABL-0149-01 | 34 | 121 | 14 | -10 | 32 | 71 | 88 | 100 | 73 |
| IHuS#ABL-0150-01 | 11 | 17 | -20 | -19 | -13 | | | | |
| IHuS#ABL-0151-01 | 38 | 126 | -10 | -15 | -6 | 70 | 100 | 100 | 100 |
| IHuS#ABL-0152-01 | -2 | 50 | -10 | -12 | -11 | 100 | 100 | 100 | 100 |
| IHuS#ABL-0153-01 | 61 | 145 | -16 | -23 | -15 | 58 | 100 | 100 | 100 |
| IHuS#ABL-0154-01 | -32 | -19 | -29 | -31 | -25 | | | | |
| IHuS#ABL-0159-01 | -22 | -5 | -23 | -34 | -33 | | | | |
| IHuS#ABL-0160-01 | -15 | -12 | -22 | -19 | -12 | | | | |
| IHuS#ABL-0161-01 | -17 | -5 | -11 | -18 | -8 | | | | |
| IHuS#ABL-0162-01 | -15 | -10 | -13 | -17 | -17 | | | | |
| IHuS#ABL-0148-01 | 290 | 369 | -8 | -13 | -10 | 21 | 100 | 100 | 100 |
| IHuS#ABL-0163-01 | 236 | 310 | -3 | -6 | 5 | 24 | 99 | 100 | 98 |
| IHuS#ABL-0171-01 | -17 | -8 | -21 | -24 | -18 | | | | |
| IHuS#ABL-0172-01 | 47 | 48 | -18 | -17 | -11 | 0 | 100 | 100 | 100 |

Figure 7 (continued)

| Sample | SEQ ID NO:58 (Q108L) | Reference A | Reference A (L11V, V89L) | Reference A (L11V, A74S, V89L) | Reference A (L11V, S49A, V89L) | SEQ ID NO:58 (Q108L) | Reference A (L11V, V89L) | Reference A (L11V, A74S, V89L) | Reference A (L11V, S49A, V89L) |
|---|---|---|---|---|---|---|---|---|---|
| IHuS#ABL-0218-01 | 63 | 72 | -12 | -15 | -9 | 13 | 100 | 100 | 100 |
| IHuS#ABL-0040-03 | 284 | 342 | 1 | -11 | -7 | 17 | 100 | 100 | 100 |
| IHuS#ABL-0090-02 | 413 | 433 | 25 | -3 | 31 | 8 | 94 | 100 | 93 |
| IHuS#ABL-0173-01 | 186 | 229 | -14 | -16 | -13 | 19 | 100 | 100 | 100 |
| IHuS#ABL-0188-01 | -14 | -8 | -21 | -23 | -16 | | | | |
| IHuS#ABL-0006-02 | 458 | 468 | 66 | 34 | 84 | 2 | 86 | 93 | 82 |
| IHuS#ABL-0189-01 | -12 | -1 | -10 | -13 | -8 | | | | |
| IHuS#ABL-0190-01 | -11 | -3 | -11 | -13 | -16 | | | | |
| IHuS#ABL-0191-01 | -21 | -10 | -17 | -19 | -20 | | | | |
| IHuS#ABL-0192-01 | -14 | 3 | -20 | -17 | -15 | | | | |
| IHuS#ABL-0198-01 | -3 | 8 | -17 | -20 | -13 | | | | |
| IHuS#ABL-0165-01 | 206 | 240 | -20 | -21 | -13 | 14 | 100 | 100 | 100 |
| IHuS#ABL-0199-01 | 229 | 250 | 16 | 5 | 16 | 8 | 94 | 98 | 94 |
| IHuS#ABL-0200-01 | -12 | 12 | -11 | -12 | -14 | | | | |
| IHuS#ABL-0201-01 | 11 | 30 | -2 | -9 | -1 | 63 | 100 | 100 | 100 |
| IHuS#ABL-0202-01 | 29 | 90 | -13 | -17 | -9 | 67 | 100 | 100 | 100 |
| IHuS#ABL-0044-02 | -25 | -23 | -26 | -23 | -22 | | | | |
| IHuS#ABL-0209-01 | 9 | 18 | -15 | -15 | -8 | | | | |
| IHuS#ABL-0210-01 | -10 | 3 | -11 | -13 | -9 | | | | |
| IHuS#ABL-0211-01 | 2 | 31 | -11 | -13 | -14 | 92 | 100 | 100 | 100 |
| IHuS#ABL-0212-01 | 47 | 137 | 4 | -5 | 9 | 66 | 97 | 100 | 97 |
| IHuS#ABL-0213-01 | -14 | 0 | -14 | -13 | -11 | | | | |

Figure 7 (continued)

| Sample | SEQ ID NO:58 (Q108L) | Reference A | Reference A (L11V, V89L) | Reference A (L11V, A74S, V89L) | Reference A (L11V, S49A, V89L) | SEQ ID NO:58 (Q108L) | Reference A (L11V, V89L) | Reference A (L11V, A74S, V89L) | Reference A (L11V, S49A, V89L) |
|---|---|---|---|---|---|---|---|---|---|
| IHuS#ABL-0183-01 | 290 | 353 | -3 | -1 | -17 | 18 | 96 | 100 | 95 |
| IHuS#ABL-0005-06 | -18 | -18 | -21 | -20 | -18 | | | | |
| IHuS#ABL-0219-01 | -3 | 7 | -12 | -14 | -8 | | | | |
| IHuS#ABL-0221-01 | -2 | 19 | -20 | -23 | -24 | | | | |
| IHuS#ABL-0222-01 | 140 | 144 | -11 | -13 | -12 | 3 | 100 | 100 | 100 |
| IHuS#ABL-0223-01 | 177 | 267 | -31 | -36 | -27 | 34 | 100 | 100 | 100 |
| IHuS#ABL-0142-01 | -2 | 25 | -22 | -23 | -15 | 100 | 100 | 100 | 100 |
| IHuS#ABL-0143-01 | 12 | 14 | -17 | -14 | -7 | | | | |
| IHuS#ABL-0144-01 | 1 | 83 | -11 | -16 | -8 | 99 | 100 | 100 | 100 |
| IHuS#ABL-0145-01 | 87 | 81 | -14 | -16 | -16 | -7 | 100 | 100 | 100 |
| IHuS#ABL-0146-01 | 16 | 61 | -16 | -17 | -16 | 74 | 100 | 100 | 100 |
| IHuS#ABL-0147-01 | 72 | 163 | -24 | -29 | -20 | 56 | 100 | 100 | 100 |
| IHuS#ABL-0031-04 | -35 | 24 | -13 | -28 | -17 | 100 | 100 | 100 | 100 |
| IHuS#ABL-0047-02 | -6 | 24 | -27 | -26 | -18 | 100 | 100 | 100 | 100 |
| IHuS#ABL-0155-01 | 49 | 65 | -4 | -14 | 0 | 24 | 100 | 100 | 100 |
| IHuS#ABL-0156-01 | 26 | 59 | -7 | -11 | -10 | 57 | 100 | 100 | 100 |
| IHuS#ABL-0157-01 | 98 | 261 | -4 | -13 | -9 | 63 | 100 | 100 | 100 |
| IHuS#ABL-0158-01 | 175 | 222 | -13 | -16 | -7 | 21 | 100 | 100 | 100 |
| IHuS#ABL-0164-01 | -19 | 17 | -19 | -22 | -14 | | | | |
| IHuS#ABL-0166-01 | -19 | -19 | -19 | -18 | -11 | | | | |
| IHuS#ABL-0167-01 | -33 | 237 | -20 | -31 | -11 | 100 | 100 | 100 | 100 |
| IHuS#ABL-0168-01 | -14 | -11 | -13 | -14 | -14 | | | | |

Figure 7 (continued)

| Sample | SEQ ID NO:58 (Q108L) | Reference A | Reference A (L11V, V89L) | Reference A (L11V, A74S, V89L) | Reference A (L11V, S49A, V89L) | SEQ ID NO:58 (Q108L) | Reference A (L11V, V89L) | Reference A (L11V, A74S, V89L) | Reference A (L11V, S49A, V89L) |
|---|---|---|---|---|---|---|---|---|---|
| IHuS#ABL-0169-01 | -5 | 21 | -10 | -12 | -11 | 100 | 100 | 100 | 100 |
| IHuS#ABL-0170-01 | 86 | 242 | -16 | -19 | -11 | 64 | 100 | 100 | 100 |
| ABL-0041-01_C | 34 | 77 | -19 | -31 | -19 | 55 | 100 | 100 | 100 |
| ABL-0053-01_C | 176 | 302 | -11 | -10 | -3 | 42 | 100 | 100 | 100 |
| ABL-0054-01_C | 249 | 293 | -8 | -13 | -6 | 15 | 100 | 100 | 100 |
| ABL-0045-01_C | 379 | 434 | 43 | 21 | 36 | 13 | 90 | 95 | 92 |
| ABL-0062-01_C | 268 | 375 | -7 | -18 | -6 | 29 | 100 | 100 | 100 |
| ABL-0039-01_C | 361 | 410 | 31 | 11 | 30 | 12 | 92 | 97 | 93 |
| HSI#260620081nd11 | 450 | 512 | 156 | 100 | 161 | 10 | 70 | 80 | 69 |
| IHuS#29Sep2011Ind14F | 151 | 221 | 36 | 22 | 39 | 32 | 84 | 90 | 82 |
| IHuS#29Sep2011Ind39F | 7 | 167 | -9 | -17 | -9 | 96 | 100 | 100 | 100 |
| IHuS#29Sep2011Ind43M | 32 | 55 | -9 | -14 | -11 | 42 | 100 | 100 | 100 |
| IHuS#29Sep2011Ind44F | 276 | 412 | 31 | 12 | 39 | 33 | 92 | 97 | 91 |
| IHuS#P6012314A20 | 76 | 102 | -10 | -10 | -8 | 25 | 100 | 100 | 100 |
| IHuS#P7012314A06 | 133 | 216 | -7 | -16 | -4 | 38 | 100 | 100 | 100 |
| IHuS#P7012314A12 | 121 | 191 | -10 | -15 | -13 | 37 | 100 | 100 | 100 |
| IHuS#ABL-0195-01 | 231 | 296 | -6 | -10 | 1 | 22 | 100 | 100 | 100 |
| IHuS#ABL-0208-01 | 351 | 384 | 50 | 26 | 49 | 9 | 87 | 93 | 87 |
| IHuS#ABL-0184-01 | 66 | 238 | -4 | -13 | -6 | 72 | 100 | 100 | 100 |
| NB130259-004 | 39 | 71 | -12 | -12 | -9 | 44 | 100 | 100 | 100 |
| IHuS#04APR2012Ind05m | 74 | 178 | 0 | -14 | 4 | 59 | 100 | 100 | 98 |

Figure 7 (continued)

| +`12111Q | 1Q | 11 | Referen ce A (L11V, V89L) | 1` | Referen ce A (L11V, S49A, V89L) | SEQ ID NO:58 (Q108L) | Referen ce A (L11V, V89L) | Referen ce A (L11V, A74S, V89L) | Referen ce A (L11V, S49A, V89L) |
|---|---|---|---|---|---|---|---|---|---|
| IHuS#04APR20 12Ind06m | 70 | 194 | -4 | -6 | 3 | 64 | 100 | 100 | 98 |
| IHuS#04APR20 12Ind07m | 41 | 146 | 3 | -3 | 4 | 72 | 98 | 100 | 97 |
| IHuS#04APR20 12Ind09m | 70 | 189 | 2 | -3 | -2 | 63 | 99 | 100 | 100 |
| IHuS#04APR20 12Ind10m | 138 | 234 | -2 | -6 | -2 | 41 | 100 | 100 | 100 |
| IHuS#04APR20 12Ind03F | 245 | 342 | 10 | 8 | 17 | 28 | 97 | 98 | 95 |
| IHuS#04APR20 12Ind04F | 351 | 387 | -8 | -11 | -9 | 9 | 100 | 100 | 100 |
| IHuS#04APR20 12Ind15F | 174 | 293 | 40 | 23 | 47 | 41 | 86 | 92 | 84 |
| IHuS#04APR20 12Ind27F | 160 | 319 | 29 | 7 | 26 | 50 | 91 | 98 | 92 |
| IHuS#04APR20 12Ind29F | 187 | 256 | -2 | -3 | -6 | 27 | 100 | 100 | 100 |
| IHuS#04APR20 12Ind31F | 118 | 265 | 96 | 56 | 97 | 56 | 64 | 79 | 63 |
| IHuS#04APR20 12Ind40F | 95 | 257 | -31 | -40 | -29 | 63 | 100 | 100 | 100 |

Figure 8A Predicted (P) and Experimentally (E) determined trypsin and chymotrypsin cleavage sites
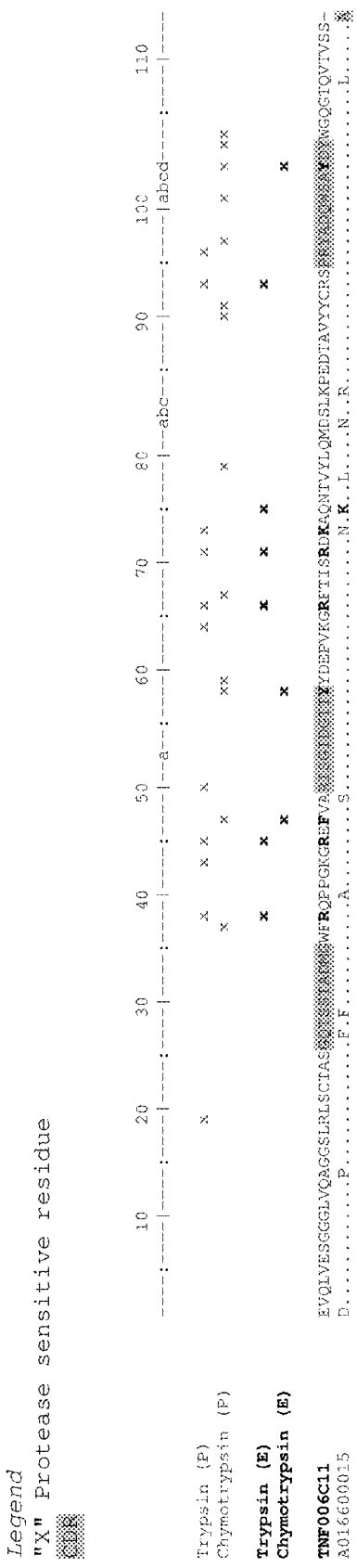
Figure 8B A01660015 analysis on Coomassie stained SDS PAGE gel
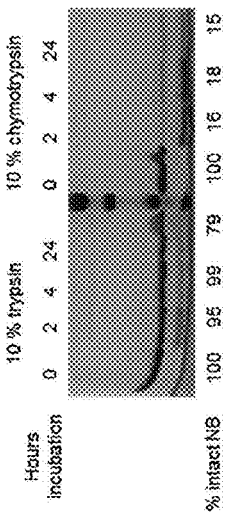

Figure 10
A
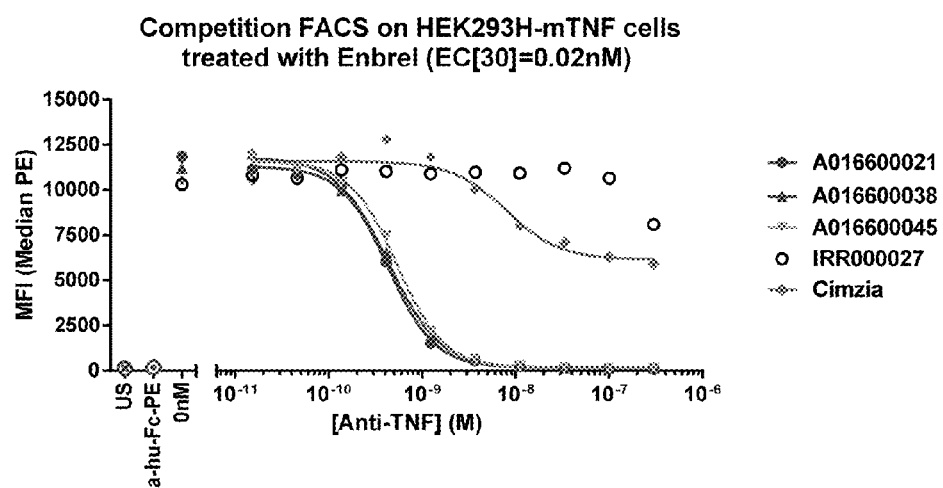
B
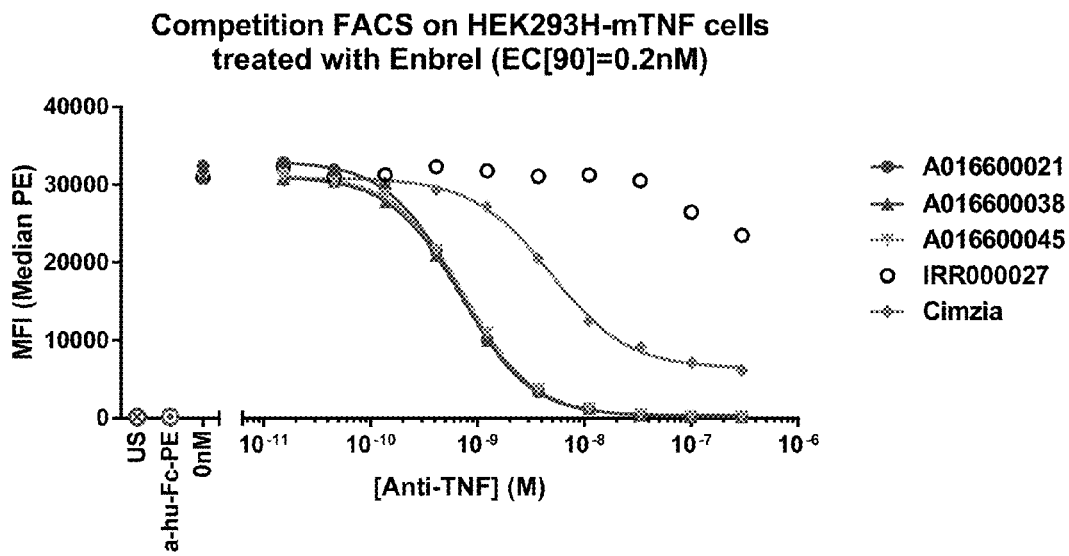

SEQUENCE LISTING

<160> NUMBER OF SEQ ID NOS: 105

<210> SEQ ID NO 1
<211> LENGTH: 121
<212> TYPE: PRT
<213> ORGANISM: Artificial Sequence
<220> FEATURE:
<223> OTHER INFORMATION: CDR Sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: CDR Sequence

<400> SEQUENCE: 2

Thr Ala Asp Met Gly
1               5

<210> SEQ ID NO 3
<211> LENGTH: 17
<212> TYPE: PRT
<213> ORGANISM: Artificial Sequence

```
<220> FEATURE:
<223> OTHER INFORMATION: CDR Sequence

<400> SEQUENCE: 3

Arg Ile Ser Gly Ile Asp Gly Thr Thr Tyr Tyr Asp Glu Pro Val Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: CDR Sequence

<400> SEQUENCE: 4

Pro Arg Tyr Ala Asp Gln Trp Ser Ala Tyr Asp Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: CDR Sequence

<400> SEQUENCE: 5

Gly Phe Thr Phe Ser Thr Ala Asp Met Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: CDR Sequence

<400> SEQUENCE: 6

Arg Ile Ser Gly Ile Asp Gly Thr Thr Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: CDR Sequence

<400> SEQUENCE: 7

Pro Arg Tyr Ala Asp Gln Trp Ser Ala Tyr Asp Tyr
1               5                   10

<210> SEQ ID NO 8
<211> LENGTH: 121
<212> TYPE: PRT
<213> ORGANISM: Artificial Sequence
<220> FEATURE:
<223> OTHER INFORMATION: CDR Sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
```

```
                    35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Arg Ser Pro Arg Tyr Ala Asp Gln Trp Ser Ala Tyr Tyr Trp Gly
                100                 105                 110

Gln Gly Thr Leu Val Thr Val Ser Ser
        115                 120

<210> SEQ ID NO 9
<211> LENGTH: 121
<212> TYPE: PRT
<213> ORGANISM: Artificial Sequence
<220> FEATURE:
<223> OTHER INFORMATION: CDR Sequence

<400> SEQUENCE: 9

Glu Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
                20                  25                  30

Asp Met Gly Trp Phe Arg Gln Ala Pro Gly Lys Gly Arg Glu Phe Val
                35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Arg Ser Pro Arg Tyr Ala Asp Gln Trp Ser Ala Tyr Tyr Trp Gly
                100                 105                 110

Gln Gly Thr Leu Val Lys Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: CDR Sequence

<400> SEQUENCE: 10

Glu Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
                20                  25                  30

Asp Met Gly Trp Phe Arg Gln Ala Pro Gly Lys Gly Arg Glu Phe Val
                35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95
```

Arg Ser Pro Arg Tyr Ala Asp Gln Trp Ser Ala Tyr Asp Tyr Trp Gly
            100                 105                 110

Gln Gly Thr Leu Val Gln Val Ser Ser
        115                 120

<210> SEQ ID NO 11
<211> LENGTH: 121
<212> TYPE: PRT
<213> ORGANISM: Artificial Sequence
<220> FEATURE:
<223> OTHER INFORMATION: CDR Sequence

<400> SEQUENCE: 11

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ser Arg Ile Ser Gly Ile Asp Gly Thr Thr Tyr Tyr Asp Glu Pro Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Lys Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: CDR Sequence

<400> SEQUENCE: 12

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ser Arg Ile Ser Gly Ile Asp Gly Thr Thr Tyr Tyr Asp Glu Pro Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Gln Ser
        115                 120

<210> SEQ ID NO 13
<211> LENGTH: 121
<212> TYPE: PRT
<213> ORGANISM: Artificial Sequence

```
<220> FEATURE:
<223> OTHER INFORMATION: CDR Sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Lys Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: CDR Sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Gln Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: CDR Sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30
```

```
Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
65                   70                  75                  80

Leu Gln Met Asn Ser Leu Arg Pro Glu Asp Thr Ala Leu Tyr Tyr Cys
                 85                  90                  95

Arg Ser Pro Arg Tyr Ala Asp Gln Trp Ser Ala Tyr Asp Tyr Trp Gly
            100                 105                 110

Gln Gly Thr Leu Val Thr Val Lys Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: CDR Sequence

<400> SEQUENCE: 16

Glu Val Gln Leu Val Glu Ser Gly Gly Gly Leu Val Gln Pro Gly Gly
 1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
65                   70                  75                  80

Leu Gln Met Asn Ser Leu Arg Pro Glu Asp Thr Ala Leu Tyr Tyr Cys
                 85                  90                  95

Arg Ser Pro Arg Tyr Ala Asp Gln Trp Ser Ala Tyr Asp Tyr Trp Gly
            100                 105                 110

Gln Gly Thr Leu Val Thr Val Gln Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: CDR Sequence

<400> SEQUENCE: 17

Glu Val Gln Leu Val Glu Ser Gly Gly Gly Val Val Gln Pro Gly Gly
 1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
65                   70                  75                  80

Leu Gln Met Asn Ser Leu Arg Pro Glu Asp Thr Ala Leu Tyr Tyr Cys
                 85                  90                  95
```

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: CDR Sequence

<400> SEQUENCE: 18

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Lys Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: CDR Sequence

<400> SEQUENCE: 19

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Gln Val Ser Ser
        115                 120

<210> SEQ ID NO 20
<211> LENGTH: 121
<212> TYPE: PRT

<213> ORGANISM: Artificial Sequence
<220> FEATURE:
<223> OTHER INFORMATION: CDR Sequence

<400> SEQUENCE: 20

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Tyr Trp Gly
            100                 105                 110

Gln Gly Thr Leu Val Thr Val Lys Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: CDR Sequence

<400> SEQUENCE: 21

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Tyr Trp Gly
            100                 105                 110

Gln Gly Thr Leu Val Thr Val Gln Ser
        115                 120

<210> SEQ ID NO 22
<211> LENGTH: 122
<212> TYPE: PRT
<213> ORGANISM: Artificial Sequence
<220> FEATURE:
<223> OTHER INFORMATION: CDR Sequence

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

-continued

```
Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Arg Ser Pro Arg Tyr Ala Asp Gln Trp Ser Ala Tyr Asp Tyr Trp Gly
                100                 105                 110

Gln Gly Thr Leu Val Thr Val Ser Ser Ala
            115                 120

<210> SEQ ID NO 23
<211> LENGTH: 122
<212> TYPE: PRT
<213> ORGANISM: Artificial Sequence
<220> FEATURE:
<223> OTHER INFORMATION: CDR Sequence

<400> SEQUENCE: 23

Glu Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
             20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Arg Ser Pro Arg Tyr Ala Asp Gln Trp Ser Ala Tyr Asp Tyr Trp Gly
                100                 105                 110

Gln Gly Thr Leu Val Lys Val Ser Ser Ala
            115                 120

<210> SEQ ID NO 24
<211> LENGTH: 122
<212> TYPE: PRT
<213> ORGANISM: Artificial Sequence
<220> FEATURE:
<223> OTHER INFORMATION: CDR Sequence

<400> SEQUENCE: 24

Glu Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
             20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
```

```
                85                  90                  95
Arg Ser Pro Arg Tyr Ala Asp Gln Trp Ser Ala Tyr Asp Tyr Trp Gly
            100                 105                 110

Gln Gly Thr Leu Val Gln Val Ser Ser Ala
            115                 120

<210> SEQ ID NO 25
<211> LENGTH: 122
<212> TYPE: PRT
<213> ORGANISM: Artificial Sequence
<220> FEATURE:
<223> OTHER INFORMATION: CDR Sequence

<400> SEQUENCE: 25

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Lys Ser Ala
            115                 120

<210> SEQ ID NO 26
<211> LENGTH: 122
<212> TYPE: PRT
<213> ORGANISM: Artificial Sequence
<220> FEATURE:
<223> OTHER INFORMATION: CDR Sequence

<400> SEQUENCE: 26

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Gln Ser Ala
            115                 120

<210> SEQ ID NO 27
<211> LENGTH: 122
```

```
<212> TYPE: PRT
<213> ORGANISM: Artificial Sequence
<220> FEATURE:
<223> OTHER INFORMATION: CDR Sequence

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Lys Val Ser Ser Ala
        115                 120

<210> SEQ ID NO 28
<211> LENGTH: 122
<212> TYPE: PRT
<213> ORGANISM: Artificial Sequence
<220> FEATURE:
<223> OTHER INFORMATION: CDR Sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Gln Val Ser Ser Ala
        115                 120

<210> SEQ ID NO 29
<211> LENGTH: 122
<212> TYPE: PRT
<213> ORGANISM: Artificial Sequence
<220> FEATURE:
<223> OTHER INFORMATION: CDR Sequence

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
```

-continued

```
                 20                  25                  30
Asp Met Gly Trp Phe Arg Gln Ala Pro Gly Lys Gly Arg Glu Phe Val
            35                  40                  45

Ser Arg Ile Ser Gly Ile Asp Gly Thr Thr Tyr Tyr Asp Glu Pro Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Lys Ser Ala
            115                 120

<210> SEQ ID NO 30
<211> LENGTH: 122
<212> TYPE: PRT
<213> ORGANISM: Artificial Sequence
<220> FEATURE:
<223> OTHER INFORMATION: CDR Sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Gln Ser Ala
            115                 120

<210> SEQ ID NO 31
<211> LENGTH: 122
<212> TYPE: PRT
<213> ORGANISM: Artificial Sequence
<220> FEATURE:
<223> OTHER INFORMATION: CDR Sequence

<400> SEQUENCE: 31

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 32
<211> LENGTH: 122
<212> TYPE: PRT
<213> ORGANISM: Artificial Sequence
<220> FEATURE:
<223> OTHER INFORMATION: CDR Sequence

<400> SEQUENCE: 32

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Lys Val Ser Ser Ala
        115                 120

<210> SEQ ID NO 33
<211> LENGTH: 122
<212> TYPE: PRT
<213> ORGANISM: Artificial Sequence
<220> FEATURE:
<223> OTHER INFORMATION: CDR Sequence

<400> SEQUENCE: 33

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Gln Val Ser Ser Ala
        115                 120

<210> SEQ ID NO 34
```

<211> LENGTH: 122
<212> TYPE: PRT
<213> ORGANISM: Artificial Sequence
<220> FEATURE:
<223> OTHER INFORMATION: CDR Sequence

<400> SEQUENCE: 34

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Lys Ser Ala
        115                 120

<210> SEQ ID NO 35
<211> LENGTH: 122
<212> TYPE: PRT
<213> ORGANISM: Artificial Sequence
<220> FEATURE:
<223> OTHER INFORMATION: CDR Sequence

<400> SEQUENCE: 35

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Gln Ser Ala
        115                 120

<210> SEQ ID NO 36
<211> LENGTH: 122
<212> TYPE: PRT
<213> ORGANISM: Artificial Sequence
<220> FEATURE:
<223> OTHER INFORMATION: CDR Sequence

<400> SEQUENCE: 36

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ala Arg Ile Ser Gly Ile Asp Gly Thr Thr Tyr Tyr Asp Glu Pro Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
            85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
            115                 120

<210> SEQ ID NO 37
<211> LENGTH: 122
<212> TYPE: PRT
<213> ORGANISM: Artificial Sequence
<220> FEATURE:
<223> OTHER INFORMATION: CDR Sequence

<400> SEQUENCE: 37

Asp Val Gln Leu Val Glu Ser Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
            85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
            115                 120

<210> SEQ ID NO 38
<211> LENGTH: 122
<212> TYPE: PRT
<213> ORGANISM: Artificial Sequence
<220> FEATURE:
<223> OTHER INFORMATION: CDR Sequence

<400> SEQUENCE: 38

Asp Val Gln Leu Val Glu Ser Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ser Arg Ile Ser Gly Ile Asp Gly Thr Thr Tyr Tyr Asp Glu Pro Val
50                  55                  60

Lys Gly Arg Phe Thr Ile Ser Arg Asp Asn Ser Lys Asn Thr Val Tyr
65                  70                  75                  80

```
Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 39
<211> LENGTH: 122
<212> TYPE: PRT
<213> ORGANISM: Artificial Sequence
<220> FEATURE:
<223> OTHER INFORMATION: CDR Sequence

<400> SEQUENCE: 39

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 40
<211> LENGTH: 122
<212> TYPE: PRT
<213> ORGANISM: Artificial Sequence
<220> FEATURE:
<223> OTHER INFORMATION: CDR Sequence

<400> SEQUENCE: 40

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120
```

```
<210> SEQ ID NO 41
<211> LENGTH: 122
<212> TYPE: PRT
<213> ORGANISM: Artificial Sequence
<220> FEATURE:
<223> OTHER INFORMATION: CDR Sequence

<400> SEQUENCE: 41

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 42
<211> LENGTH: 34
<212> TYPE: PRT
<213> ORGANISM: Artificial Sequence
<220> FEATURE:
<223> OTHER INFORMATION: HIS6-FLAG3 tag

<400> SEQUENCE: 42

His His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 43
<211> LENGTH: 5
<212> TYPE: PRT
<213> ORGANISM: Artificial Sequence
<220> FEATURE:
<223> OTHER INFORMATION: C-terminal end

<400> SEQUENCE: 43

Val Thr Val Lys Ser
1               5

<210> SEQ ID NO 44
<211> LENGTH: 5
<212> TYPE: PRT
<213> ORGANISM: Artificial Sequence
<220> FEATURE:
<223> OTHER INFORMATION: C-terminal end

<400> SEQUENCE: 44

Val Thr Val Gln Ser
1               5

<210> SEQ ID NO 45
```

```
<211> LENGTH: 5
<212> TYPE: PRT
<213> ORGANISM: Artificial Sequence
<220> FEATURE:
<223> OTHER INFORMATION: C-terminal end

<400> SEQUENCE: 45

Val Lys Val Ser Ser
1               5

<210> SEQ ID NO 46
<211> LENGTH: 5
<212> TYPE: PRT
<213> ORGANISM: Artificial Sequence
<220> FEATURE:
<223> OTHER INFORMATION: C-terminal end

<400> SEQUENCE: 46

Val Gln Val Ser Ser
1               5

<210> SEQ ID NO 47
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 47

Val Thr Val Lys Ser Xaa
1               5

<210> SEQ ID NO 48
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 48

Val Thr Val Gln Ser Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 49

Val Lys Val Ser Ser Xaa
```

```
1               5
```

<210> SEQ ID NO 50
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 50

```
Val Gln Val Ser Ser Xaa
1               5
```

<210> SEQ ID NO 51
<211> LENGTH: 6
<212> TYPE: PRT
<213> ORGANISM: Artificial Sequence
<220> FEATURE:
<223> OTHER INFORMATION: C-terminal end

<400> SEQUENCE: 51

```
Val Thr Val Lys Ser Ala
1               5
```

<210> SEQ ID NO 52
<211> LENGTH: 6
<212> TYPE: PRT
<213> ORGANISM: Artificial Sequence
<220> FEATURE:
<223> OTHER INFORMATION: C-terminal end

<400> SEQUENCE: 52

```
Val Thr Val Gln Ser Ala
1               5
```

<210> SEQ ID NO 53
<211> LENGTH: 6
<212> TYPE: PRT
<213> ORGANISM: Artificial Sequence
<220> FEATURE:
<223> OTHER INFORMATION: C-terminal end

<400> SEQUENCE: 53

```
Val Lys Val Ser Ser Ala
1               5
```

<210> SEQ ID NO 54
<211> LENGTH: 6
<212> TYPE: PRT
<213> ORGANISM: Artificial Sequence
<220> FEATURE:
<223> OTHER INFORMATION: C-terminal end

<400> SEQUENCE: 54

```
Val Gln Val Ser Ser Ala
1               5
```

<210> SEQ ID NO 55
<211> LENGTH: 5
<212> TYPE: PRT
<213> ORGANISM: Artificial Sequence
<220> FEATURE:

<223> OTHER INFORMATION: C-terminal end

<400> SEQUENCE: 55

Val Thr Val Ser Ser
1               5

<210> SEQ ID NO 56
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 56

Val Thr Val Ser Ser Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: C-terminal end

<400> SEQUENCE: 57

Val Thr Val Ser Ser Ala
1               5

<210> SEQ ID NO 58
<211> LENGTH: 121
<212> TYPE: PRT
<213> ORGANISM: Artificial Sequence
<220> FEATURE:
<223> OTHER INFORMATION: CDR Sequence

<400> SEQUENCE: 58

Gln Val Gln Leu Val Glu Ser Gly Gly Gly Leu Val Gln Ala Gly Gly
1               5                   10                  15

Ser Leu Arg Leu Ser Cys Thr Ala Ser Gly Gln Thr Ser Ser Thr Ala
            20                  25                  30

Asp Met Gly Trp Phe Arg Gln Pro Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Lys Ala Gln Asn Thr Val Tyr
65                  70                  75                  80

Leu Gln Met Asp Ser Leu Lys Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Gln Val Thr Val Ser Ser
        115                 120

<210> SEQ ID NO 59
<211> LENGTH: 121
<212> TYPE: PRT
<213> ORGANISM: Artificial Sequence
<220> FEATURE:

-continued

<223> OTHER INFORMATION: CDR Sequence

<400> SEQUENCE: 59

Glu Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: CDR Sequence

<400> SEQUENCE: 60

Asp Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 61
<211> LENGTH: 122
<212> TYPE: PRT
<213> ORGANISM: Artificial Sequence
<220> FEATURE:
<223> OTHER INFORMATION: CDR Sequence

<400> SEQUENCE: 61

Asp Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val

```
                35                  40                  45
Ser Arg Ile Ser Gly Ile Asp Gly Thr Thr Tyr Tyr Asp Glu Pro Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Arg Ser Pro Arg Tyr Ala Asp Gln Trp Ser Ala Tyr Tyr Trp Gly
            100                 105                 110

Gln Gly Thr Leu Val Thr Val Ser Ser Ala
        115                 120

<210> SEQ ID NO 62
<211> LENGTH: 122
<212> TYPE: PRT
<213> ORGANISM: Artificial Sequence
<220> FEATURE:
<223> OTHER INFORMATION: CDR Sequence

<400> SEQUENCE: 62

Asp Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
                20                  25                  30

Asp Met Gly Trp Phe Arg Gln Ala Pro Gly Lys Gly Arg Glu Phe Val
            35                  40                  45

Ala Arg Ile Ser Gly Ile Asp Gly Thr Thr Tyr Tyr Asp Glu Pro Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Arg Ser Pro Arg Tyr Ala Asp Gln Trp Ser Ala Leu Asp Tyr Trp Gly
            100                 105                 110

Gln Gly Thr Leu Val Thr Val Ser Ser Ala
        115                 120

<210> SEQ ID NO 63
<211> LENGTH: 122
<212> TYPE: PRT
<213> ORGANISM: Artificial Sequence
<220> FEATURE:
<223> OTHER INFORMATION: CDR Sequence

<400> SEQUENCE: 63

Asp Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
                20                  25                  30

Asp Met Gly Trp Phe Arg Gln Ala Pro Gly Lys Gly Arg Glu Phe Val
            35                  40                  45

Cys Arg Ile Ser Gly Ile Asp Gly Thr Thr Tyr Tyr Asp Glu Pro Val
 50                  55                  60

Lys Gly Arg Phe Thr Cys Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95
```

```
Arg Ser Pro Arg Tyr Ala Asp Gln Trp Ser Ala Leu Asp Tyr Trp Gly
            100                 105                 110

Gln Gly Thr Leu Val Thr Val Ser Ser Ala
        115                 120

<210> SEQ ID NO 64
<211> LENGTH: 122
<212> TYPE: PRT
<213> ORGANISM: Artificial Sequence
<220> FEATURE:
<223> OTHER INFORMATION: CDR Sequence

<400> SEQUENCE: 64

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 65
<211> LENGTH: 121
<212> TYPE: PRT
<213> ORGANISM: Artificial Sequence
<220> FEATURE:
<223> OTHER INFORMATION: CDR Sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Leu Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Gln Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Pro Ser Gln Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
```

<220> FEATURE:
<223> OTHER INFORMATION: CDR Sequence

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ser Arg Ile Ser Gly Ile Asp Gly Thr Thr Tyr Tyr Asp Glu Pro Val
    50                  55                  60

Gln Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Arg Pro Ser Gln Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: CDR Sequence

<400> SEQUENCE: 67

Gln Val Gln Leu Val Glu Ser Gly Gly Gly Leu Val Gln Ala Gly Gly
1               5                   10                  15

Ser Leu Arg Leu Ser Cys Thr Ala Ser Gly Gln Thr Ser Ser Thr Ala
            20                  25                  30

Asp Met Gly Trp Phe Arg Gln Pro Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Lys Ala Gln Asn Thr Val Tyr
65                  70                  75                  80

Leu Gln Met Asp Ser Leu Lys Pro Glu Asp Thr Ala Val Tyr Tyr Cys
                85                  90                  95

Arg Ser Pro Arg Tyr Ala Asp Trp Ser Ala Tyr Asp Tyr Trp Gly
            100                 105                 110

Gln Gly Thr Gln Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: CDR Sequence

<400> SEQUENCE: 68

Gln Val Gln Leu Val Glu Ser Gly Gly Gly Leu Val Gln Ala Gly Gly
1               5                   10                  15

Ser Leu Arg Leu Ser Cys Thr Ala Ser Gly Gln Thr Ser Ser Thr Ala
            20                  25                  30

Asp Met Gly Trp Phe Arg Gln Pro Pro Gly Lys Gly Arg Glu Phe Val
            35                  40                  45

Ala Arg Ile Ser Gly Ile Asp Gly Thr Thr Tyr Tyr Asp Glu Pro Val
 50                  55                  60

Lys Gly Arg Phe Thr Ile Ser Arg Asp Lys Ser Gln Asn Thr Val Tyr
 65                  70                  75                  80

Leu Gln Met Asp Ser Leu Lys Pro Glu Asp Thr Ala Val Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Gln Val Thr Val Ser Ser
            115                 120

<210> SEQ ID NO 69
<211> LENGTH: 122
<212> TYPE: PRT
<213> ORGANISM: Artificial Sequence
<220> FEATURE:
<223> OTHER INFORMATION: CDR Sequence

<400> SEQUENCE: 69

Asp Val Gln Leu Val Glu Ser Gly Gly Gly Val Val Gln Pro Gly Gly
 1               5                  10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
            35                  40                  45

Ala Arg Ile Ser Gly Ile Asp Gly Thr Thr Tyr Tyr Asp Glu Pro Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala His Asp Tyr Trp Gly
            100                 105                 110

Gln Gly Thr Leu Val Thr Val Ser Ser Ala
            115                 120

<210> SEQ ID NO 70
<211> LENGTH: 115
<212> TYPE: PRT
<213> ORGANISM: Artificial Sequence
<220> FEATURE:
<223> OTHER INFORMATION: CDR Sequence

<400> SEQUENCE: 70

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

-continued

```
Thr Ile Gly Gly Ser Leu Ser Arg Ser Ser Gln Gly Thr Leu Val Thr
            100                 105                 110

Val Ser Ser
        115

<210> SEQ ID NO 71
<211> LENGTH: 115
<212> TYPE: PRT
<213> ORGANISM: Artificial Sequence
<220> FEATURE:
<223> OTHER INFORMATION: CDR Sequence

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 72
<211> LENGTH: 116
<212> TYPE: PRT
<213> ORGANISM: Artificial Sequence
<220> FEATURE:
<223> OTHER INFORMATION: CDR Sequence

<400> SEQUENCE: 72

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 73
<211> LENGTH: 116
<212> TYPE: PRT
```

<213> ORGANISM: Artificial Sequence
<220> FEATURE:
<223> OTHER INFORMATION: CDR Sequence

<400> SEQUENCE: 73

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 74
<211> LENGTH: 115
<212> TYPE: PRT
<213> ORGANISM: Artificial Sequence
<220> FEATURE:
<223> OTHER INFORMATION: CDR Sequence

<400> SEQUENCE: 74

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 75
<211> LENGTH: 116
<212> TYPE: PRT
<213> ORGANISM: Artificial Sequence
<220> FEATURE:
<223> OTHER INFORMATION: CDR Sequence

<400> SEQUENCE: 75

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30
```

```
Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 76
<211> LENGTH: 115
<212> TYPE: PRT
<213> ORGANISM: Artificial Sequence
<220> FEATURE:
<223> OTHER INFORMATION: CDR Sequence

<400> SEQUENCE: 76

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 77
<211> LENGTH: 116
<212> TYPE: PRT
<213> ORGANISM: Artificial Sequence
<220> FEATURE:
<223> OTHER INFORMATION: CDR Sequence

<400> SEQUENCE: 77

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
```

```
                    85                  90                  95
Thr Ile Gly Gly Ser Leu Ser Arg Ser Ser Gln Gly Thr Leu Val Thr
                100                 105                 110

Val Ser Ser Ala
        115

<210> SEQ ID NO 78
<211> LENGTH: 117
<212> TYPE: PRT
<213> ORGANISM: Artificial Sequence
<220> FEATURE:
<223> OTHER INFORMATION: CDR Sequence

<400> SEQUENCE: 78

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser Ala Ala
        115

<210> SEQ ID NO 79
<211> LENGTH: 118
<212> TYPE: PRT
<213> ORGANISM: Artificial Sequence
<220> FEATURE:
<223> OTHER INFORMATION: CDR Sequence

<400> SEQUENCE: 79

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser Ala Ala Ala
        115

<210> SEQ ID NO 80
<211> LENGTH: 116
```

<212> TYPE: PRT
<213> ORGANISM: Artificial Sequence
<220> FEATURE:
<223> OTHER INFORMATION: CDR Sequence

<400> SEQUENCE: 80

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 81
<211> LENGTH: 117
<212> TYPE: PRT
<213> ORGANISM: Artificial Sequence
<220> FEATURE:
<223> OTHER INFORMATION: CDR Sequence

<400> SEQUENCE: 81

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 82
<211> LENGTH: 118
<212> TYPE: PRT
<213> ORGANISM: Artificial Sequence
<220> FEATURE:
<223> OTHER INFORMATION: CDR Sequence

<400> SEQUENCE: 82

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe

```
                    20                  25                  30
Gly Met Ser Trp Val Arg Gln Ala Pro Gly Lys Gly Leu Glu Trp Val
                35                  40                  45
Ser Ser Ile Ser Gly Ser Gly Ser Asp Thr Leu Tyr Ala Asp Ser Val
        50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Leu Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly
            115

<210> SEQ ID NO 83
<211> LENGTH: 115
<212> TYPE: PRT
<213> ORGANISM: Artificial Sequence
<220> FEATURE:
<223> OTHER INFORMATION: CDR Sequence

<400> SEQUENCE: 83

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Arg Ser Phe
                20                  25                  30
Gly Met Ser Trp Val Arg Gln Ala Pro Gly Lys Gly Pro Glu Trp Val
                35                  40                  45
Ser Ser Ile Ser Gly Ser Gly Ser Asp Thr Leu Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Leu Tyr Tyr Cys
                85                  90                  95
Thr Ile Gly Gly Ser Leu Ser Arg Ser Ser Gln Gly Thr Leu Val Thr
            100                 105                 110
Val Ser Ser
        115

<210> SEQ ID NO 84
<211> LENGTH: 116
<212> TYPE: PRT
<213> ORGANISM: Artificial Sequence
<220> FEATURE:
<223> OTHER INFORMATION: CDR Sequence

<400> SEQUENCE: 84

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Arg Ser Phe
                20                  25                  30
Gly Met Ser Trp Val Arg Gln Ala Pro Gly Lys Gly Pro Glu Trp Val
                35                  40                  45
Ser Ser Ile Ser Gly Ser Gly Ser Asp Thr Leu Tyr Ala Asp Ser Val
        50                  55                  60
Lys Gly Arg Phe Thr Ile Ser Arg Asp Asn Ser Lys Asn Thr Leu Tyr
65                  70                  75                  80
```

-continued

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 85
<211> LENGTH: 5
<212> TYPE: PRT
<213> ORGANISM: Artificial Sequence
<220> FEATURE:
<223> OTHER INFORMATION: Linker

<400> SEQUENCE: 85

Gly Gly Gly Gly Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Linker

<400> SEQUENCE: 86

Ser Gly Gly Ser Gly Gly Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Linker

<400> SEQUENCE: 87

Gly Gly Gly Gly Cys Gly Gly Gly Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Linker

<400> SEQUENCE: 88

Gly Gly Gly Gly Ser Gly Gly Gly Ser
1               5

<210> SEQ ID NO 89
<211> LENGTH: 10
<212> TYPE: PRT
<213> ORGANISM: Artificial Sequence
<220> FEATURE:
<223> OTHER INFORMATION: Linker

<400> SEQUENCE: 89

Gly Gly Gly Gly Ser Gly Gly Gly Gly Ser
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Linker

<400> SEQUENCE: 90

Gly Gly Gly Gly Ser Gly Gly Gly Gly Ser Gly Gly Gly Gly Ser
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: Linker

<400> SEQUENCE: 91

Gly Gly Gly Gly Ser Gly Gly Gly Gly Ser Gly Gly Gly Gly Gly
1               5                   10                  15

Gly Ser

<210> SEQ ID NO 92
<211> LENGTH: 20
<212> TYPE: PRT
<213> ORGANISM: Artificial Sequence
<220> FEATURE:
<223> OTHER INFORMATION: Linker

<400> SEQUENCE: 92

Gly Gly Gly Gly Ser Gly Gly Gly Gly Ser Gly Gly Gly Gly Ser Gly
1               5                   10                  15

Gly Gly Gly Ser
            20

<210> SEQ ID NO 93
<211> LENGTH: 25
<212> TYPE: PRT
<213> ORGANISM: Artificial Sequence
<220> FEATURE:
<223> OTHER INFORMATION: Linker

<400> SEQUENCE: 93

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 94
<211> LENGTH: 30
<212> TYPE: PRT
<213> ORGANISM: Artificial Sequence
<220> FEATURE:
<223> OTHER INFORMATION: Linker

<400> SEQUENCE: 94

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 95
<211> LENGTH: 35
<212> TYPE: PRT
<213> ORGANISM: Artificial Sequence
<220> FEATURE:
<223> OTHER INFORMATION: Linker

```
<400> SEQUENCE: 95

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser
        35

<210> SEQ ID NO 96
<211> LENGTH: 40
<212> TYPE: PRT
<213> ORGANISM: Artificial Sequence
<220> FEATURE:
<223> OTHER INFORMATION: Linker

<400> SEQUENCE: 96

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser
        35                  40

<210> SEQ ID NO 97
<211> LENGTH: 15
<212> TYPE: PRT
<213> ORGANISM: Artificial Sequence
<220> FEATURE:
<223> OTHER INFORMATION: G1 Hinge

<400> SEQUENCE: 97

Glu Pro Lys Ser Cys Asp Lys Thr His Thr Cys Pro Pro Cys Pro
1               5                   10                  15

<210> SEQ ID NO 98
<211> LENGTH: 24
<212> TYPE: PRT
<213> ORGANISM: Artificial Sequence
<220> FEATURE:
<223> OTHER INFORMATION: 9GS-G1 hinge

<400> SEQUENCE: 98

Gly Gly Gly Gly Ser Gly Gly Gly Ser Glu Pro Lys Ser Cys Asp Lys
1               5                   10                  15

Thr His Thr Cys Pro Pro Cys Pro
                20

<210> SEQ ID NO 99
<211> LENGTH: 12
<212> TYPE: PRT
<213> ORGANISM: Artificial Sequence
<220> FEATURE:
<223> OTHER INFORMATION: Llama upper long hinge region

<400> SEQUENCE: 99

Glu Pro Lys Thr Pro Lys Pro Gln Pro Ala Ala Ala
1               5                   10

<210> SEQ ID NO 100
<211> LENGTH: 62
<212> TYPE: PRT
<213> ORGANISM: Artificial Sequence
<220> FEATURE:
<223> OTHER INFORMATION: G3 hinge
```

<400> SEQUENCE: 100

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 101
<211> LENGTH: 5
<212> TYPE: PRT
<213> ORGANISM: Artificial Sequence
<220> FEATURE:
<223> OTHER INFORMATION: CDR Sequence

<400> SEQUENCE: 101

Ser Phe Gly Met Ser
1               5

<210> SEQ ID NO 102
<211> LENGTH: 17
<212> TYPE: PRT
<213> ORGANISM: Artificial Sequence
<220> FEATURE:
<223> OTHER INFORMATION: CDR Sequence

<400> SEQUENCE: 102

Ser Ile Ser Gly Ser Gly Ser Asp Thr Leu Tyr Ala Asp Ser Val Lys
1               5                   10                  15

Gly

<210> SEQ ID NO 103
<211> LENGTH: 6
<212> TYPE: PRT
<213> ORGANISM: Artificial Sequence
<220> FEATURE:
<223> OTHER INFORMATION: CDR Sequence

<400> SEQUENCE: 103

Gly Gly Ser Leu Ser Arg
1               5

<210> SEQ ID NO 104
<211> LENGTH: 121
<212> TYPE: PRT
<213> ORGANISM: Artificial Sequence
<220> FEATURE:
<223> OTHER INFORMATION: TNF006C11

<400> SEQUENCE: 104

Glu Val Gln Leu Val Glu Ser Gly Gly Gly Leu Val Gln Ala Gly Gly
1               5                   10                  15

Ser Leu Arg Leu Ser Cys Thr Ala Ser Gly Gln Thr Ser Ser Thr Ala
            20                  25                  30

Asp Met Gly Trp Phe Arg Gln Pro Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Lys Ala Gln Asn Thr Val Tyr

-continued

```
                65                  70                  75                  80
Leu Gln Met Asp Ser Leu Lys Pro Glu Asp Thr Ala Val Tyr Tyr Cys
                    85                  90                  95

Arg Ser Pro Arg Tyr Ala Asp Gln Trp Ser Ala Tyr Asp Tyr Trp Gly
                100                 105                 110

Gln Gly Thr Gln Val Thr Val Ser Ser
            115                 120

<210> SEQ ID NO 105
<211> LENGTH: 4
<212> TYPE: PRT
<213> ORGANISM: Artificial Sequence
<220> FEATURE:
<223> OTHER INFORMATION: Tag

<400> SEQUENCE: 105

Gly Gly Gly Cys
1
```

TNF BINDERS

RELATED APPLICATIONS

This application is continuation of U.S. Ser. No. 15/501,011, filed Feb. 1, 2017, which is a national stage filing under 35 U.S.C. §371 of International Application No. PCT/EP2016/077595, filed Nov. 14, 2016, and claims the benefit under 35 U.S.C. §119(e) of U.S. provisional application Ser. No. 62/254,375, filed Nov. 12, 2015, the entire contents of each of which is incorporated by reference herein in its entirety.

SUMMARY

The present invention relates to amino acid sequences, compounds and polypeptides binding to tumor necrosis factor alpha ("TNF" or "TNF-alpha"). In particular, the present invention relates to improved heavy-chain immunoglobulin single variable domains (also referred to herein as "ISV's" or "ISVDs") binding to tumor necrosis factor alpha, as well as to proteins, polypeptides and other constructs, compounds, molecules or chemical entities that comprise such ISVDs, collectively TNF binders. Other aspects, embodiments, features, uses and advantages of the invention will be clear to the skilled person based on the disclosure herein.

BACKGROUND

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regard to the CDRs, as is well-known in the art, there are multiple conventions to define and describe the CDRs of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims, even though the CDRs according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website http://www.bioinf.org.uk/abs/.

Inflammatory bowel disease (IBD), Crohn's disease (CD) and ulcerative colitis (UC) are chronic, disabling and progressive diseases. Most non-biological drug therapies such as aminosalicylates, steroids and immunomodulators provide symptomatic improvement but fail to stop the underlying inflammatory process and do not change the disease course. The advent of anti-tumor necrosis factor-α (anti-TNF-α) agents (infliximab, adalimumab, certolizumab pegol) has dramatically changed the way IBD is treated by changing both disease course (fewer surgeries, less hospitalizations, better quality of life, steroid sparing, greater clinical remission and mucosal healing rates in both CD and UC) and patients' quality of life and work productivity (cf. Amiot and Peyrin-Biroulet 2015 Ther Adv Gastroenterol 8:66-82). The most common route of administration for these therapeutic proteins is injection. Since most of these proteins have short serum half-lives, they need to be administered frequently or in high doses to be effective. Systemic administration is furthermore associated with an increased risk of infections. Together this results in a loss of patient compliance (cf. Singh et al. 2008 J Pharm Sci 97:2497-2523).

However, the undesirable long-term side effects and opportunistic infections, including tuberculosis and non-Hodgkins lymphoma are caused by the generalized immunosuppression and result from repeated systemic injections of the currently used monoclonal antibody treatment (Ali et al., 2013; Galloway et al., 2011; Ford & Peyrin-Biroulet, 2013; Kozuch & Hanauer, 2008; Schreiber et al., 2007; Syed et al., 2013).

Oral administration of anti-TNF-α antibodies should avoid some of these side effects.

However, these anti-TNF-α agents are complex proteins. Oral delivery results in degradation in the acidic and protease-rich environment of the gastrointestinal (GI) tract.

In using decoy proteins to protect the therapeutic antibody, a patient based study comprising polyclonal bovine colostral antibodies to human TNF alpha (AVX-470) administered via the oral route has recently been conducted by Avaxia Biologics Inc. in ulcerative colitis patients. However, the study was discontinued.

Hence, there is a need for new IBD drugs.

ISVDs (and in particular Nanobodies) that can bind to TNF and their uses are well-known in the art, for example from WO 2004/041862 and WO 2006/122786, which describe Nanobodies against TNF and their use for the prevention and/or treatment of diseases and disorders associated with and/or mediated by TNF-α or TNF-α signaling, such as inflammation, rheumatoid arthritis, Crohn's disease, ulcerative colitis, inflammatory bowel syndrome, multiple sclerosis, Addison's disease, autoimmune hepatitis, autoimmune parotitis, diabetes type 1, epididymitis, glomerulonephritis, Graves' disease, Guillain-Barre syndrome, Hashimoto's disease, hemolytic anemia, systemic lupus erythematosus, male infertility, myasthenia gravis, pemphigus, psoriasis, rheumatic fever, sarcoidosis, scleroderma, Sjogren's syndrome, spondyloarthropathies, thyroiditis, and vasculitis.

WO 2006/122786 disclosed as SEQ ID NO: 125 a specific anti-TNF-α Nanobody referred to as NC55TNF_NC7 (PMP6C11). The sequence of this prior art Nanobody is given in Table A below as SEQ ID NO: 58. Table A also gives (as SEQ ID NO: 1) the sequence of a sequence optimized version (also referred to herein as "Reference A") of this prior art TNF binder, together with its CDRs (according to the Kabat and Abm conventions). As can be seen from the alignment in FIG. 2, this sequence optimized version contains, compared to the prior art sequence of SEQ ID NO: 58, the following mutations: Q1E, A14P, Q27F, S29F, P40A, A49S, K73N, Q75K, V78L, D82aN, K83R and Q108L (according to Kabat numbering).

WO 2015/1733256 relates to improved immunoglobulin domains, comprising C-terminal extensions preventing the binding of so-called pre-existing antibodies ("PEAs"). WO 2015/1733256 discloses SEQ ID NO: 345 as a specific anti-TNF-α Nanobody, which is referred to herein also as TNF345 (SEQ ID NO: 59). As can be seen from the alignment in FIG. 2, the sequence optimized version Reference A contains, compared to the prior art sequence of SEQ ID NO: 59, the following mutations: V11L and L89V (according to Kabat numbering).

A cocktail of toxin-neutralizing llama monoclonal VHH antibody fragments has recently been proposed for potential oral therapy (Hussack et al., 2011 J Biol Chem 286, 8961-76.). However, Dumoulin et al. (2002 Protein Sci, 11, 500-15), Harmsen et al. (2006 Appl Microbiol Biotechnol, 72, 544-51) and Hussack et al. (2012 Methods Mol Biol, 911, 417-29) alleged that the single domain llama antibody fragments appear to be greatly susceptible to proteolytic destruction within the human gastrointestinal system.

WO2007/025977 describes a treatment of chronic enterocolitis, involving in situ secretion of anti-mTNF Nanobodies by orally administered *L. lactis* bacteria.

SUMMARY OF THE INVENTION

The present invention aims to provide improved TNF binders, in particular improved anti-TNF compounds and polypeptides, more particularly anti-TNF ISVDs and even more in particular improved anti-TNF Nanobodies. The improved TNF binders provided by the invention are also referred to herein as the "TNF binders of the invention" or "TNF binders".

More in particular, the present invention aims to provide improved TNF-binders that would be useful in treating diseases of the digestive tract such as for instance inflammatory bowel disease (IBD), irritable bowel syndrome, Crohn's disease, ulcerative colitis, mucositis, aphthous stomatitis, celiac disease, trauma to the digestive tract and cancers to the digestive tract. Those TNF-binders should preferably be stable and amenable for oral administration.

It is expected that orally administered TNF-binders not only neutralize TNF in the lumen of the digestive tract but gain access to the lamina propria and submucosa as the intestinal barrier of the digestive tract may be breached or compromised through gross inflammation and/or ulceration, including but not limited to periodontal disease, aphthous stomatitis, bacterial, viral, fungal or parasitic infections of the digestive tract, peptic ulcers, ulcers associated with stress or *H. pylori* infection, damage caused by esophageal reflux, inflammatory bowel disease, damage caused by cancer of the digestive tract, food intolerance, including celiac disease, or ulcers induced by NSAIDs or other ingested or systemically delivered drugs.

Hence, the invention aims to provide improved TNF binders that are variants of Reference A and that have reduced binding by interfering factors (generally referred to as "pre-existing antibodies" or "PEAS") that may be present in the sera from some healthy human subjects as well as from patients. Reference is made to WO 2012/175741, WO 2013/024059 and also for example, to Holland et al. (J. Clin. Immunol. 2013, 33(7):1192-203) as well as to the co-pending published PCT application WO2015/173325 (Appl. no. PCT/EP2015/060643) by Ablynx N.V. filed on May 13, 2015 and entitled "Improved immunoglobulin variable domains".

As further described herein, the TNF binders of the invention preferably have the same combination of CDRs (i.e. CDR1, CDR2 and CDR3) as are present in Reference A.

Some preferred, but non-limiting TNF binders of the invention are listed in FIG. 3 as SEQ ID NOs: 8 to 41, 62, 63, 64, 65, 66 and 69. FIG. 4 shows an alignment of the sequences SEQ ID NO: 8-41 with SEQ ID NO: 1 (Reference A) and SEQ ID NO: 58 (PMP6C11). The binders of SEQ ID NOs: 22 to 41, 62-66 and 69 are examples of TNF binders of the invention having a C-terminal alanine extension, i.e. an alanine residue at the C-terminal end of the ISVD-sequence (also sometimes referred to as "position 114") compared to the usual C-terminal sequence VTVSS (SEQ ID NO: 55, as present in Reference A). As described in WO 2012/175741 (but also for example in WO 2013/024059 and WO2015/173325), this C-terminal alanine extension can prevent the binding of so-called "pre-existing antibodies" (assumed to be IgG's) to a putative epitope that is situated at the C-terminal region of the ISVD. This epitope is assumed to include, among other residues, the surface-exposed amino acid residues of the C-terminal sequence VTVSS as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in a lot of cases even essentially fully prevent) the binding of the "pre-existing antibodies" that can be found in the sera from a range of subjects (both healthy subjects as well as patients), it has been found that the sera from some subjects (such as the sera from patients with some immune diseases such as SLE) can contain pre-existing antibodies that can bind to the C-terminal region of an ISVD (when such region is exposed) even when the ISVD contains such a C-terminal alanine (or more generally, such C-terminal extension). Reference is again made to the co-pending published PCT application WO2015/173325 by Assignee filed on May 13, 2015 and entitled "Improved immunoglobulin variable domains".

Accordingly, one specific objective of the invention is to provide TNF binders that are improved variants of the anti-TNF Nanobody referred to herein as "Reference A" and that have reduced binding by so-called "pre-existing antibodies", and in particular of the kind described in WO2015/173325 (i.e. those pre-existing antibodies that can bind to an exposed C-terminal region of an ISVD even in the presence of a C-terminal extension).

Generally, the invention achieves this objective by providing amino acid sequences that are variants of the sequence of SEQ ID NO: 1 that comprise the following amino acid residues (i.e. mutations compared to the sequence of SEQ ID NO: 1):

89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, in the TNF binders provided by the invention:
- the amino acid residue at position 11 is preferably chosen from L or V; and
- the amino acid residue at position 89 is preferably suitably chosen from T, V or L; and
- the amino acid residue at position 110 is preferably suitably chosen from T, K or Q; and
- the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

Of the amino acid sequences provided by the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

In a particularly preferred embodiment, in the TNF binders provided by the invention, the amino acid residue at position 11 is V, the amino acid residue at position 89 is L, the amino acid residue at position 110 is T and the amino acid residue at position 112 is S.

In a particularly preferred embodiment, the present invention relates to TNF binders, such as Immunoglobulin single variable domains (ISVD), having:
 a CDR1 (according to Abm) that is the amino acid sequence GFTFSTADMG (SEQ ID NO: 5); and
 a CDR2 (according to Abm) that is the amino acid sequence RISGIDGTTY (SEQ ID NO: 6); and
 a CDR3 (according to Abm) that is the amino acid sequence PRYADQWSAYDY (SEQ ID NO: 4);
 and having:
 a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;
 and/or
 no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);
 and
 the amino acid residue at position 11 is V; and
 the amino acid residue at position 89 is L; and
 the amino acid residue at position 110 is T; and
 the amino acid residue at position 112 is 5; and
 the amino acid residue at position 49 is A; and
 the amino acid residue at position 74 is S.

As mentioned, the amino acid sequences provided by the invention described herein can bind (and in particular, can specifically bind) to TNF.

The amino acid sequences provided by the invention preferably have EC50 value in the cell-based assay using KYM cells described in Example 1, under 3), of WO 04/041862 that is better than 50 nM, more preferably better than 25 nM, such as less than 10 nM.

Table B lists some non-limiting possible combinations of the amino acid residues that can be present at positions 11, 89, 110 and 112 in the TNF binders of the invention. Combinations that are particularly preferred are indicated in bold, and the most preferred combinations are indicated in bold/underline.

However, upon optimizing the sequences ("sequence optimization") of the TNF-binders with regard to minimizing or eliminating binding sites for pre-existing antibodies on the one hand and humanizing on the other hand, various properties of the TNF-binders, including stability, were (remarkably) influenced negatively. In particular, the melting temperature as a measure for physical stability decreased, production in both the eukaryotic host *P. pastoris* and prokaryotic host *E. coli* was diminished, and the stability in GI fluids was reduced.

Instead of "mutating back" the binding sites for PEAs and the humanizing mutations, thereby compromising sequence optimization, the present inventors surprisingly found that amino acid residues 49 and/or 74 could be altered such that both seemingly mutually exclusive requirements were satisfied. Tables B-1 and B-2 list some non-limiting possible combinations of the amino acid residues that can be present at positions 11, 89, 110, 112, 49 and/or 74 in the TNF binders of the invention.

The TNF binders provided by the invention are further as described in the description, examples and figures herein, i.e. they have CDRs that are as described herein and have an overall degree of sequence identity (as defined herein) with the sequence of SEQ ID NO: 1 that is as disclosed herein and/or may have a limited number of "amino acid differences" (as described herein) with (one of) these reference sequences.

The TNF binders of the invention preferably comprise the following CDRs (according to the Kabat convention):
 a CDR1 (according to Kabat) that is the amino acid sequence TADMG (SEQ ID NO: 2); and
 a CDR2 (according to Kabat) that is the amino acid sequence RISGIDGTTYYDEPVKG (SEQ ID NO: 3); and
 a CDR3 (according to Kabat) that is the amino acid sequence PRYADQWSAYDY (SEQ ID NO:4).

Alternatively, when the CDRs are given according to the Abm convention, the TNF binders of the invention preferably comprise the following CDRs:
 a CDR1 (according to Abm) that is the amino acid sequence GFTFSTADMG (SEQ ID NO:5); and
 a CDR2 (according to Abm) that is the amino acid sequence RISGIDGTTY (SEQ ID NO:6); and
 a CDR3 (according to Abm) that is the amino acid sequence PRYADQWSAYDY (SEQ ID NO:4).

A TNF binder of the invention preferably also has:
 a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%; and/or
 no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs).

With regard to the various aspects and preferred aspects of the TNF binders of the invention provided by the invention, when it comes to the degree of sequence identity with respect to SEQ ID NO: 1 and/or the number and kind of "amino acid differences" that may be present in such a binder of the invention (i.e. compared to the sequence of SEQ ID NO: 1), it should be noted that, when it is said that (i) an amino acid sequence of the invention has a degree of sequence identity with the sequence of SEQ ID NO: 1 of at least 85%, preferably at least 90%, more preferably at least 95% (in which the CDRs, any C-terminal extension that may be present, as well as the mutations at positions 11, 89, 110 and/or 112 required by the specific aspect involved, are not taken into account for determining the degree of sequence identity); and/or when it is said that (ii) an amino acid sequence of the invention has no more than 7, preferably no more than 5, such as only 3, 2 or 1 "amino acid differences" with the sequence of SEQ ID NO: 1 (again, not taking into account any C-terminal extension that may be present and not taking into account the mutations at positions 11, 89, 110 and/or 112 required by the specific aspect involved), then this also includes sequences that have no amino acid differences with the sequence of SEQ ID NO: 1 other than the mutations at positions 11, 89, 110 and/or 112 required by the specific aspect involved) and any C-terminal extension that may be present.

Thus, in one specific aspect of the invention, the TNF binders of the invention may have 100% sequence identity with SEQ ID NO: 1 (including the CDRs, but not taking into account the mutation(s) or combination of mutations at positions 11, 49, 74 89, 110 and/or 112 disclosed herein, and/or any C-terminal extension that may be present) and/or may have no amino acid differences with SEQ ID NO: 1 (i.e. other than the mutation(s) or combination of mutations at positions 11, 89, 110 and/or 112 disclosed herein and any C-terminal extension that may be present).

When any amino acid differences are present (i.e. besides any C-terminal extension and the mutations at positions 11, 89, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the TNF binders of the invention have the same CDRs (defined according to the Abm convention) as are present in SEQ ID NO: 1.

Also, when a TNF binder of the invention according to any aspect of the invention has one or more amino acid differences with the sequence of SEQ ID NO: 1 (besides the mutations at positions 11, 89, 110 and/or 112 that are required by the specific aspect involved), then some specific, but non-limiting examples of such mutations/amino acid differences that may be present (i.e. compared to the sequences of SEQ ID NO: 1) are for example E1D, P40A, P40L, P40S (and in particular P40A), S49A, A74S, L78V, T87A or any suitable combination thereof. Also, the TNF binders of the invention may suitably comprise (a suitable combination of) D60A, E61D and/or P62S mutations, in particular as an ADS motif at positions 60-62 (see SEQ ID NO: 39 for a non-limiting example). Other examples of mutations are (a suitable combination of) one or more suitable "humanizing" substitutions; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions).

Of the aforementioned mutations, the presence of an S49A, A74S and/or L78V mutation (or any suitable combination of any two thereof, including all three thereof) is preferred (see SEQ ID NOs: 40, 39, 36, 64, 69, 37, 38, 41, and 62-63). FIG. 5 shows an alignment of SEQ ID NO: 1, SEQ ID NO: 31 and SEQ ID NOs: 36 to 41.

Also, when the TNF binders of the invention are present at and/or form the N-terminal part of the polypeptide or compound in which they are present, then they preferably contain a D at position 1 (i.e. an E1D mutation compared to Reference A). Accordingly, in a further aspect, the invention relates to a polypeptide of the invention (which is as further described herein) that has a TNF binder of the invention (which is as further described herein) at its N-terminal end, wherein said TNF binder of the invention has a D at position 1.

Similarly, when a TNF binder of the invention is used in monovalent format, it preferably has both a C-terminal extension X(n) as described herein and a D at position 1.

Some preferred but non-limiting examples of monovalent TNF binders with a D at position 1 and a C-terminal extension are given as SEQ ID NOs: 40, 39, 36, 64, 69, 37, 38, 41, and 62-63, preferably SEQ ID NO:s 36, 39 and 40, most preferably, SEQ ID NO: 40. In this respect, it should be noted that the TNF binders of SEQ ID NOs: 40, 39, 36, 64, 69, 37, 38, 41, and 62-63 can also be used in a compound or polypeptide of the invention that is not in a monovalent format. In that case, when the TNF binders of SEQ ID NOs: 40, 39, 36, 64, 69, 37, 38, 41, and 62-63 will preferably have an E instead of a D at their N-terminal end (i.e. an D1E mutation compared to the sequences of SEQ ID NOs: 40, 39, 36, 64, 69, 37, 38, 41, and 62-63) when they are not present at the N-terminal end of said polypeptide or compound of the invention (instead, preferably, the N-terminal ISVD of said polypeptide or compound of the invention will have a D at position 1; also, they will preferably not contain a C-terminal extension (such as the C-terminal alanine present in SEQ ID NOs: 40, 39, 36, 64, 69, 37, 38, 41, and 62-63) when they are not present at the C-terminal end of the compound or polypeptide (instead, preferably, the C-terminal ISVD of said polypeptide or compound of the invention will have a C-terminal extension).

By means of preferred, but non-limiting examples, SEQ ID NOs: 40, 39, 36, 64, 69, 37, 38 and 62-63 are also examples of TNF binders of the invention having further amino acid differences with SEQ ID NO: 1, i.e. S49A, A74S and/or L78V. Thus, in a specific aspect, the invention relates to TNF binders of the invention (i.e. having mutations at positions 11, 89, 110 and/or 112 as described herein and also further being as described herein) that at least have a suitable combination of an S49A, A74S and/or L78V mutation, and preferably a suitable combination of any two of these mutations, such as all three of these mutations.

The TNF binders of the invention, when they are used in a monovalent format and/or when they are present at and/or form the C-terminal end of the protein, polypeptide or other compound or construct in which they are present (or when they otherwise have an "exposed" C-terminal end in such protein, polypeptide or other compound or construct, by which is generally meant that the C-terminal end of the ISV is not associated with or linked to a constant domain (such as a CH1 domain); reference is again made to WO 2012/175741 and WO 2015/1733256), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as follows:

(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a TNF binder of the invention does not contain a (free) cysteine residue (unless said cysteine residue is used or intended for further functionalization, for example for pegylation).

Some specific, but non-limiting examples of useful C-terminal extensions are the following amino acid sequences: A, AA, AAA, G, GG, GGG, AG, GA, AAG, AGG, AGA, GGA, GAA or GAG.

When the TNF binders of the invention contain mutations at positions 110 or 112 (optionally in combination with mutations at position 11 and/or 89 as described herein), the C-terminal amino acid residues of framework 4 (starting from position 109) can be as follows: (i) if no C-terminal extension is present: VTVKS (SEQ ID NO: 43), VTVQS (SEQ ID NO: 44), VKVSS (SEQ ID NO: 45) or VQVSS (SEQ ID NO: 46); or (ii) if a C-terminal extension is present: $VTVKSX_{(n)}$ (SEQ ID NO: 47), VTVQSX(n) (SEQ ID NO: 48), VKVSSX(n) (SEQ ID NO: 49) or $VQVSSX_{(n)}$ (SEQ ID NO: 50), such as VTVKSA (SEQ ID NO: 51), VTVQSA (SEQ ID NO: 52), VKVSSA (SEQ ID NO: 53) or VQVSSA (SEQ ID NO: 54). When the TNF binders of the invention do not contain mutations at positions 110 or 112 (but only mutations at position 11 and/or 89 as described herein), the C-terminal amino acid residues of framework 4 (starting from position 109) will usually be either: (i) when no C-terminal extension is present: VTVSS (SEQ ID NO: 55) (as in the sequence of SEQ ID NO: 1); or (ii) when a C-terminal extension is present: $VTVSSX_{(n)}$ (SEQ ID NO: 56) such as VTVSSA (SEQ ID NO: 57). In these C-terminal sequences, X and n are as defined herein for the C-terminal extensions.

As can be seen from the alignment in FIG. 4 as well as from FIG. 3, the TNF binders of SEQ ID NOs: 40, 39, 36, 64, 69, 37, 38, 41, and 62-63 have both an E1D mutation and a C-terminal alanine extension. As mentioned, the presence of both a D at position 1 as well as a C-terminal extension make these TNF binders (and other TNF binders of the invention with a D at position 1 and a C-terminal extension) particularly suitable for use in a monovalent format (i.e. for the purposes described herein).

Accordingly, in a further aspect, the invention relates to a TNF binder of the invention (which is as further described herein) that has a D at position 1 and a C-terminal extension X(n) (which is preferably a single Ala residue). Said TNF binders are preferably (used and/or intended for use) in a monovalent format. In one specific aspect, said monovalent TNF binder is chosen from SEQ ID NOs: 40, 39, 36, 64, 69, 37, 38, 62, 63 and 41.

Some preferred but non-limiting examples of TNF binders of the invention are given in SEQ ID NOs: 8 to 41 and 62-69, and each of these sequences forms a further aspect of the invention (as do proteins, polypeptides or other compounds or constructs that comprise one of these sequences).

Some particularly preferred TNF binders of the invention are the sequences of SEQ ID NOs: 40, 39, 36, 64, 69, 37, 38, 41 and 62-63 (or, as described herein, variants thereof with an E at position 1 and/or without a C-terminal extension, depending on their intended use in a polypeptide or compound of the invention).

Thus, in a first aspect, the invention relates to an immunoglobulin single variable domain having:
 a CDR1 (according to Kabat) that is the amino acid sequence TADMG (SEQ ID NO: 2); and
 a CDR2 (according to Kabat) that is the amino acid sequence RISGIDGTTYYDEPVKG (SEQ ID NO: 3); and
 a CDR3 (according to Kabat) that is the amino acid sequence PRYADQWSAYDY (SEQ ID NO: 4);
and having:
 a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;
and/or
 no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:

the amino acid residue at position 11 is preferably chosen from L or V; and the amino acid residue at position 89 is preferably suitably chosen from T, V or L; and the amino acid residue at position 110 is preferably suitably chosen from T, K or Q; and the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, the invention relates to an immunoglobulin single variable domain having:

a CDR1 (according to Kabat) that is the amino acid sequence TADMG (SEQ ID NO: 2); and a CDR2 (according to Kabat) that is the amino acid sequence RISGIDGTTYYDEPVKG (SEQ ID NO: 3); and a CDR3 (according to Kabat) that is the amino acid sequence PRYADQWSAYDY (SEQ ID NO: 4);

and having:

a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

which immunoglobulin single variable domain comprises the following amino acid residues (i.e. mutations compared to the amino acid sequence of SEQ ID NO: 1) at the positions mentioned (numbering according to Kabat):

89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, the TNF binders of the invention preferably have no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs).

In particular, in the TNF binders provided by the invention, the amino acid residue at position 11 is V, the amino acid residue at position 89 is L, the amino acid residue at position 110 is T and the amino acid residue at position 112 is S.

As described herein, some specific, but non-limiting examples of such mutations/amino acid differences that may be present (i.e. in suitable combination) are for example E1D, P40A, P40L, P40S (and in particular P40A), 549A, A74S, L78V, T87A or any suitable combination thereof, as well as for example (a suitable combination of) D60A, E61D and/or P62S mutations (in particular as an ADS motif at positions 60-62) and (a suitable combination of, see e.g. SEQ ID NO: 39) one or more suitable "humanizing" substitutions. As also mentioned, the presence of an 549A, A74S and/or L78V mutation (or any suitable combination of any two thereof, including all three thereof) is preferred (as well as the presence of a D at position 1 when the TNF binder is present at and/or forms the N-terminal end of a compound or polypeptide of the invention or is in monovalent format).

In a preferred aspect, the TNF binder of the invention such as an ISVD comprises an alanine at position 49 (A49).

In a further preferred aspect, the TNF binder of the invention such as an ISVD comprises a serine at position 74 (S74).

In a further preferred aspect, the TNF binder of the invention such as an ISVD comprises an asparagine at position 73 (N73) and or a lysine at position 75 (K75).

As mentioned, in the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to an immunoglobulin single variable domain having:

a CDR1 (according to Kabat) that is the amino acid sequence TADMG (SEQ ID NO: 2); and a CDR2 (according to Kabat) that is the amino acid sequence RISGIDGTTYYDEPVKG (SEQ ID NO: 3); and a CDR3 (according to Kabat) that is the amino acid sequence PRYADQWSAYDY (SEQ ID NO: 4).

and having:

a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:

the amino acid residue at position 11 is preferably chosen from L or V; and the amino acid residue at position 89 is T; and the amino acid residue at position 110 is preferably suitably chosen from T, K or Q (and is preferably T); and the amino acid residue at position 112 is preferably suitably chosen from S, K or Q (and in preferably S).

In another preferred aspect, the invention relates to an immunoglobulin single variable domain having:

a CDR1 (according to Kabat) that is the amino acid sequence TADMG (SEQ ID NO: 2); and a CDR2 (according to Kabat) that is the amino acid sequence RISGIDGTTYYDEPVKG (SEQ ID NO: 3); and a CDR3 (according to Kabat) that is the amino acid sequence PRYADQWSAYDY (SEQ ID NO: 4);

and having:

a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:

the amino acid residue at position 11 is V; and the amino acid residue at position 89 is L; and the amino acid residue at position 110 is preferably suitably chosen from T, K or Q; and the amino acid residue at position 112 is preferably suitably chosen from S, K or Q.

In one specific, but non-limiting aspect, the TNF binders of the invention comprise the following amino acid residues (i.e. mutations compared to the sequence of SEQ ID NO: 1) at the positions mentioned (numbering according to Kabat):

11V in combination with 89L; or
11V in combination with 110K or 110Q;
11V in combination with 112K or 112Q;
11V in combination with 89L and 110K or 110Q; or
11V in combination with 89L and 112K or 112Q;

and have CDRs (according to Kabat) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):

89L in combination with 11V; or
89L in combination with 110K or 110Q; or
89L in combination with 112K or 112Q; or
89L in combination with 11V and 110K or 110Q; or
89L in combination with 11V and 112K or 112Q;

and have CDRs (according to Kabat) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):

110K or 110Q in combination with 11V; or
110K or 110Q in combination with 89L; or
110K or 110Q in combination with 11V and 89L;

and have CDRs (according to Kabat) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):

112K or 112Q in combination with 11V; or
112K or 112Q in combination with 89L; or
112K or 112Q in combination with 11V and 89L;

and have CDRs (according to Kabat) and have an overall degree of sequence identity with the amino acid sequence of SEQ ID NO: 1 that are as described herein.

In another aspect, the TNF binders of the invention comprise a T at position 89 and have CDRs (according to Kabat) and have an overall degree of sequence identity with the amino acid sequence of SEQ ID NO: 1 that are as described herein.

In another aspect, the TNF binders of the invention comprise a V at position 11 and an L at position 89 and have CDRs (according to Kabat) and have an overall degree of sequence identity with the amino acid sequence of SEQ ID NO: 1 that are as described herein.

As mentioned, the TNF binders of the invention according to the above aspects are preferably further such that they contain a suitable combination of an S49A, A74S and/or L78V mutation, and preferably a suitable combination of any two of these mutations, such as all three of these mutations (and again, when the TNF binder is monovalent or present at the N-terminal end of a compound or polypeptide of the invention, preferably also an E1D mutation).

In another aspect, the invention relates to an immunoglobulin single variable domain having:
- a CDR1 (according to Abm) that is the amino acid sequence GFTFSTADMG (SEQ ID NO: 5); and
- a CDR2 (according to Abm) that is the amino acid sequence RISGIDGTTY (SEQ ID NO: 6); and
- a CDR3 (according to Abm) that is the amino acid sequence PRYADQWSAYDY (SEQ ID NO: 4);

and having:
- a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:
the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, the invention relates to an immunoglobulin single variable domain having:
- a CDR1 (according to Abm) that is the amino acid sequence GFTFSTADMG (SEQ ID NO: 5); and
- a CDR2 (according to Abm) that is the amino acid sequence RISGIDGTTY (SEQ ID NO: 6); and
- a CDR3 (according to Abm) that is the amino acid sequence PRYADQWSAYDY (SEQ ID NO: 4);

and having:
- a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

which immunoglobulin single variable domain comprises the following amino acid residues (i.e. mutations compared to the amino acid sequence of SEQ ID NO: 1) at the positions mentioned (numbering according to Kabat):
89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

As mentioned, when a TNF binder of the invention is used in a monovalent format and/or is present at the C-terminal end of a compound of the invention (as defined herein), the TNF binder (and consequently, the resulting compound of the invention) preferably has a C-terminal extension X(n), which C-terminal extension may be as described herein for the TNF binders of the invention and/or as described in WO 2012/175741 or WO2015/173325.

As mentioned, in the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to an immunoglobulin single variable domain having:
- a CDR1 (according to Abm) that is the amino acid sequence GFTFSTADMG (SEQ ID NO: 5); and
- a CDR2 (according to Abm) that is the amino acid sequence RISGIDGTTY (SEQ ID NO: 6); and
- a CDR3 (according to Abm) that is the amino acid sequence PRYADQWSAYDY (SEQ ID NO: 4);

and having:
- a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:
- the amino acid residue at position 11 is preferably chosen from L or V; and
- the amino acid residue at position 89 is T; and
- the amino acid residue at position 110 is preferably suitably chosen from T, K or Q (and is preferably T); and
- the amino acid residue at position 112 is preferably suitably chosen from S, K or Q (and in preferably S).

In another preferred aspect, the invention relates to an immunoglobulin single variable domain having:
- a CDR1 (according to Abm) that is the amino acid sequence GFTFSTADMG (SEQ ID NO: 5); and
- a CDR2 (according to Abm) that is the amino acid sequence RISGIDGTTY (SEQ ID NO: 6); and
- a CDR3 (according to Abm) that is the amino acid sequence PRYADQWSAYDY (SEQ ID NO: 4);

and having:
- a degree of sequence identity with the amino acid sequence of SEQ ID NO: 1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which:
- the amino acid residue at position 11 is V; and
- the amino acid residue at position 89 is L; and
- the amino acid residue at position 110 is preferably suitably chosen from T, K or Q; and
- the amino acid residue at position 112 is preferably suitably chosen from S, K or Q.

In one specific, but non-limiting aspect, the TNF binders of the invention comprise the following amino acid residues (i.e. mutations compared to the sequence of SEQ ID NO: 1) at the positions mentioned (numbering according to Kabat):
- 11V in combination with 89L; or
- 11V in combination with 110K or 110Q;
- 11V in combination with 112K or 112Q;
- 11V in combination with 89L and 110K or 110Q; or
- 11V in combination with 89L and 112K or 112Q;

and have CDRs (according to Abm) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):
- 89L in combination with 11V; or
- 89L in combination with 110K or 110Q; or
- 89L in combination with 112K or 112Q; or
- 89L in combination with 11V and 110K or 110Q; or
- 89L in combination with 11V and 112K or 112Q;

and have CDRs (according to Abm) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):
- 110K or 110Q in combination with 11V; or
- 110K or 110Q in combination with 89L; or
- 110K or 110Q in combination with 11V and 89L;

and have CDRs (according to Abm) and have an overall degree of sequence identity with the amino acid sequence of SEQ ID NO: 1 that are as described herein.

In another specific, but non-limiting aspect, the TNF binders of the invention comprise the following amino acid residues (i.e. mutations compared to the sequence of SEQ ID NO: 1) at the positions mentioned (numbering according to Kabat):
- 112K or 112Q in combination with 11V; or
- 112K or 112Q in combination with 89L; or
- 112K or 112Q in combination with 11V and 89L;

and have CDRs (according to Abm) and have an overall degree of sequence identity with the amino acid sequence of SEQ ID NO: 1 that are as described herein.

In another aspect, the TNF binders of the invention comprise a T at position 89 and have CDRs (according to Abm) and have an overall degree of sequence identity with the amino acid sequence of SEQ ID NO: 1 that are as described herein.

In another aspect, the TNF binders of the invention comprise a V at position 11 and an L at position 89 and have CDRs (according to Abm) and have an overall degree of sequence identity with the amino acid sequence of SEQ ID NO: 1 that are as described herein.

As mentioned, the TNF binders of the invention according to the above aspects are preferably further such that they contain a suitable combination of an S49A, A74S and/or L78V mutation, and preferably a suitable combination of any two of these mutations, such as all three of these mutations (and again, when the TNF binder is monovalent or present at the N-terminal end of a compound or polypeptide of the invention, preferably also an E1D mutation).

In another specific, but non-limiting aspect, the invention relates to a TNF binder as described herein that is in a monovalent format, and in particular to a TNF binder as described herein that is in a monovalent format and that has a D at position 1 (and/or an E1D mutation) and a C-terminal extension X(n) as described herein (such as a C-terminal alanine residue).

In another specific, but non-limiting aspect, the invention relates to an immunoglobulin single variable domain that is or essentially consists of an amino acid sequence chosen from one of the following amino acid sequences: SEQ ID NO: 40, SEQ ID NO: 39, SEQ ID NO: 36, SEQ ID NO: 64, SEQ ID NO: 69, SEQ ID NO: 62, SEQ ID NO: 63, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 37, SEQ ID NO: 38, SEQ ID NO: 41, SEQ ID NO: 65, SEQ ID NO: 66, SEQ ID NO: 67 and SEQ ID NO: 68.

In another specific, but non-limiting aspect, the invention relates to an immunoglobulin single variable domain that is or essentially consists of an amino acid sequence chosen from one of the following amino acid sequences: SEQ ID NO: 40, SEQ ID NO: 39, SEQ ID NO: 36, SEQ ID NO: 64, SEQ ID NO: 69, SEQ ID NO: 62, SEQ ID NO: 63, SEQ ID NO: 37, SEQ ID NO: 38, SEQ ID NO: 41, SEQ ID NO: 65, SEQ ID NO: 66, SEQ ID NO: 67 and SEQ ID NO: 68.

For the purposes of the invention, the digestive tract consists of the mouth, pharynx, esophagus, stomach, small intestine (duodenum, jejunum, ileum), large intestine (cecum, colon, rectum) and anus.

For the purposes of the invention, the "gastrointestinal tract", or "GI tract" is understood to include the stomach, small intestine (duodenum, jejunum, ileum), large intestine (cecum, colon, rectum) and anus. The term "gastric digestion" as used herein is understood to describe digestion in the stomach, small intestine and/or large intestine.

The term "gastric degradation" of an antibody is used herein to refer to degradation of an ISVD, compound or polypeptide of the invention in the stomach, small intestine, large intestine by endogenous or exogenous enzymes present in the stomach, small intestine and large intestine or due to exposure to acidic conditions during gastric digestion.

The term "stabilized ISVD", "stabilized compounds" and "stabilized polypeptides" as used herein is understood to describe an ISVD, compound or polypeptide, respectively that has been engineered to make it more stable to degradation in the digestive tract when administered topically. As compared to an ISVD, compound or polypeptide that has not been processed or engineered in accordance with the invention, a stabilized ISVD, compound or polypeptide that is engineered in accordance with the invention is degraded more slowly or to a lesser extent by gastric digestion, such as digestion by endogenous or exogenous enzymes present in the stomach, small intestine and large intestine and/or by the acidic conditions present in the stomach. "Stabilized ISVDs", "stabilized compounds" and "stabilized polypeptides" are also referred to as "ISVDs with enhanced stability to degradation in the GI tract", "compounds with enhanced stability to degradation in the GI tract" and "polypeptides with enhanced stability to degradation in the GI tract", respectively.

Topical administration of an ISVD, compound or polypeptide to the digestive tract is challenging because the digestive tract degrades and digests the topically applied ISVDs, compounds and polypeptides. In the stomach, the low pH and the protease pepsin degrade ingested ISVDs, compounds and polypeptides. In the small intestine, the enzymes trypsin and chymotrypsin, among others, degrade ingested ISVDs, compounds and polypeptides. In the large intestine, bacterially-derived proteases degrade ingested ISVDs, compounds and polypeptides. ISVDs, compounds and polypeptides with improved stability to gastric digestion would be preferred for topical application to the GI tract.

Stabilized ISVDs, compounds and polypeptides may be generated by the mutation of one or more amino acid residues that are susceptible to gastric degradation into amino acid residues that are resistant to gastric degradation. Stabilized ISVDs, compounds and polypeptides may be generated by the mutation of multiple amino acid residues moieties that increase stability to gastric degradation.

Hence, the present invention relates to identifying amino acid residues imparting stability of the TNF binder of the invention, and enhancing the stability of the TNF binder. Preferably, the TNF binder is mad more resistant to gastric degradation by one or more of low pH conditions or the activities of one or more of proteases such as pepsin, trypsin, chemotrypsin, and/or bacterially-derived proteases.

In an embodiment the invention relates to a method of identifying an amino acid residue that imparts stability of an ISVD, compound or polypeptide to gastric degradation comprising the steps of: (a) degrading an ISVD, compound or polypeptide by one or more proteases into fragments; and (b) analysing the fragments of step (a) by a suitable means, such as e.g. LC-MS; thereby identifying the amino acid residue(s) imparting stability of an ISVD, compound or polypeptide to gastric degradation.

In an embodiment the invention relates to a method of enhancing the stability of an ISVD, compound or polypeptide to gastric degradation comprising the steps (a) and (b) above, followed by: (c) mutating the amino acid residue(s) imparting stability of an ISVD, compound or polypeptide to gastric degradation; and (d) repeating steps (a) and (b) of above; whereby the absence of one or more fragments indicates an enhanced stability of the ISVD, compound or polypeptide to gastric degradation.

In the present specification:
the term "immunoglobulin single variable domain" (also referred to as "ISV" or ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VH's), IgNAR, domains, (single domain) antibodies (such as dAb's™) that are VH domains or that are derived from a VH domain and (single domain) antibodies (such as dAb's™) that are VL domains or that are derived from a VL domain. Unless explicitly mentioned otherwise herein, ISVDs that are based on and/or derived from heavy chain variable domains (such as VH or VHH domains) are generally preferred. Most preferably, unless explicitly indicated otherwise herein, an ISVD will be a Nanobody.

the term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

Generally, unless indicated otherwise herein, the ISVDs, Nanobodies, polypeptides, proteins and other compounds and constructs referred to herein will be intended for use in prophylaxis or treatment of diseases or disorders in man (and/or optionally also in warmblooded animals and in particular mammals). Thus, generally, the ISVDs, Nanobodies, polypeptides, proteins and other compounds and constructs described herein are preferably such that they can be used as, and/or can suitably be a part of, a (biological) drug or other pharmaceutically or therapeutically active compound and/or of a pharmaceutical product or composition. Such a drug, compound or product is preferably such that it is suitable for administration to a human being, e.g. for prophylaxis or treatment of a subject in need of such prophylaxis or treatment or for example as part of a clinical trial. As further described herein, for this purpose, such a drug or compound may contain other moieties, entities or binding units besides the ISVDs provided by the invention (which, as also described herein, may for example be one or more other further therapeutic moieties and/or one or more other moieties that influence the pharmacokinetic or pharmacodynamic properties of the ISVD-based or Nanobody-based biological, such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 2009/138159. An ISVD-based biological or Nanobody-based biological is preferably a therapeutic or intended for use as a therapeutic (which includes prophylaxis and diagnosis) and for this purpose preferably contains at least one ISVD against a therapeutically relevant target (such as for example RANK-L, vWF, IgE, RSV, CXCR4, IL-23 or other interleukins, etc.). For some specific but non-limiting examples of such ISVD-based or Nanobody-based biologicals, reference is to Examples 8 to 18 and also for example made to the various applications by Ablynx N.V. (such as for example and without limitation WO 2004/062551, WO 2006/122825, WO 2008/020079 and WO 2009/068627), as well as for example (and without limitation) to applications such as WO 2006/038027, WO 2006/059108, WO 2007/063308, WO 2007/063311, WO 2007/066016 and WO 2007/085814. Also, as further described herein, the further moiety may be an ISVD or Nanobody as described herein directed against a (human) serum protein such as (human) serum albumin, and such an ISVD or Nanobody may also find therapeutic uses, in particular in and/or for extending the half-life of the TNF binders described herein. Reference is for example made to WO 2004/041865, WO 2006/122787 and WO 2012/175400, which generally describe the use of serum-albumin binding Nanobodies for half-life extension. Also, in the present specification, unless explicitly mentioned otherwise herein, all terms mentioned herein have the meaning given in WO 2009/138519 (or in the prior art cited in WO 2009/138519) or WO 2008/020079 (or in the prior art cited in WO 2008/020079). Also, where a method or technique is not specifically described herein, it can be performed as described in WO 2009/138519 (or in the prior art cited in WO 2009/138519) or WO 2008/020079 (or in the prior art cited in WO 2008/020079). Also, as described herein, any pharmaceutical product or composition comprising any ISVD or compound of the invention may also comprise one or more further components known per se for use in pharmaceutical products or compositions (i.e. depending on the intended pharmaceutical form) and/or for example one or more other compounds or active principles intended for therapeutic use (i.e. to provide a combination product).

Also, when used in the present specification or claims, the following terms have the same meaning as given on, and/or where applicable can be determined in the manner described in, pages 62-75 of WO 2009/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 2010/130832 of Ablynx N.V. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 2009/138519, WO 2010/130832 or WO 2008/020079.

The term "half-life" as used here in relation to an ISVD, Nanobody, ISVD-based biological, Nanobody-based biological or any other amino acid sequence, compound or polypeptide referred to herein can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t½-alpha, t½-beta and the area under the curve (AUC). In this respect it should be noted that the term "half-life" as used herein in particular refers to the t½-beta or terminal half-life (in which the t½-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t½-beta, either with or without an increase in the t½-alpha and/or the AUC or both.

Accordingly, in an aspect the present invention relates to a compound as described herein, wherein said compound further comprises a serum protein binding moiety.

In a further aspect, the present invention relates to a compound as described herein, wherein said serum protein binding moiety binds serum albumin.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al., eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDRs, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

The invention also relates to proteins, polypeptides and other constructs, molecules or chemical entities that comprise or essentially consist of the TNF binders of the invention as described herein (i.e. that comprise or essentially consist of one or more of such TNF binders, such as one, two or three such TNF binders); to methods for expressing/producing the TNF binders of the invention and/or for expressing/producing proteins, polypeptides and other constructs, molecules or chemical entities comprising the same; to compositions and products (such as pharmaceutical compositions and products) that comprise the TNF binders of the invention and/or proteins, polypeptides and other constructs, molecules or chemical entities comprising the same; to nucleotide sequence and nucleic acids that encode the TNF binders of the invention and/or that encode proteins or polypeptides comprising the same; and to uses (and in particular therapeutic, prophylactic and diagnostic uses) of the TNF binders of the invention and of proteins, polypeptides and other constructs, molecules or chemical entities comprising the same.

These and other aspects, embodiments, advantages, applications and uses of the invention will become clear from the further description herein.

Accordingly, in a further aspect, the invention relates to proteins (such as fusion proteins), polypeptides, constructs, compounds or other chemical entities that comprise or essentially consist of at least one (such as one, two or three) TNF binder of the invention (also collectively referred to herein as "compounds of the invention", "polypeptides of the invention", "constructs of the invention", or "fusion proteins of the invention"). Hence, the compound of the invention can be a polypeptide.

Such compounds of the invention can, besides the one or more TNF binders of the invention, further contain one or more other amino acid sequences, chemical entities or moieties. These other amino acid sequences, chemical entities or moieties can confer one or more desired properties to the (resulting) compound of the invention and/or can alter the properties of the (resulting) compound of the invention in a desired manner, for example to provide the (resulting) compound of the invention with a desired biological and/or therapeutic activity (for example, to provide the resulting compound of the invention with affinity and preferably potency against another therapeutically relevant target such that the resulting compound becomes "bispecific" with respect to TNF and that other therapeutically relevant target), to provide a desired half-life and/or to (otherwise) modify or improve pharmacokinetic and/or pharmacodynamic properties, to target the compound of the invention to specific cells, tissues or organs (including cancer cells and cancer tissues), to provide a cytotoxic effect and/or to serve as a detectable tag or label. Some non-limiting examples of such other amino acid sequences, chemical entities or moieties are:

one or more suitable linkers (such a 9GS, 15G5 or 35GS linker); and/or one or more binding domains or binding units that are directed against a therapeutically relevant target other than TNF (i.e. so as to provide a compound of the invention that is bispecific for both TNF and the other therapeutically relevant target); and/or one or more binding domains or binding units that provide for an increase in half-life (for example, a binding domain or binding unit that can bind against a serum protein such as serum albumin); and/or one or more binding domains or binding units that target the compound of the invention to a desired cell, tissue or organ (such as a cancer cell); and/or one or more binding domains or binding units that provide for increased specificity against TNF (usually, these will be able to bind to TNF but will generally by themselves essentially not be functional against TNF); and/or a binding domain, binding unit or other chemical entity that allows for the compound of the invention to be internalized into a (desired) cell (for example, an internalizing anti-EGFR Nanobody as described in WO 2005/044858); and/or a moiety that improves half-life such as a suitable polyethyleneglycol group (i.e. PEGylation) or an amino acid sequence that provides for increased half-life such as human serum albumin or a suitable fragment thereof (i.e. albumin fusion) or for example a serum albumin binding peptide as described in WO 2008/068280; and/or a payload such as a cytotoxic payload; and/or a detectable label or tag, such as a radiolabel or fluorescent label; and/or a tag that can help with immobilization, detection and/or purification of the compound of the invention, such as a HIS or FLAG3 tag; and/or a tag that can be functionalized, such as a C-terminal GGC or GGGC tag; and/or a C-terminal extension X(n), which may be as further described herein for the TNF binders of the invention and/or as described in WO 2012/175741 or WO2015/173325.

Although usually less preferred, it is also not excluded from the scope of the invention that the compounds of the invention can also contain one or more parts or fragments of a (preferably human) conventional antibody (such as an Fc part or a functional fragment thereof or one or more constant domains) and/or from a Camelid heavy-chain only antibody (such as one or more constant domains).

In a particular aspect, the present invention relates to a construct that comprises or essentially consists of an ISVD as defined herein or a compound as defined herein, and which further comprises one or more other groups, residues, moieties or binding units, optionally linked via one or more peptidic linkers.

In a further particular aspect, the present invention relates to a construct as defined herein, in which said one or more other groups, residues, moieties or binding units is chosen from the group consisting of a polyethylene glycol molecule, serum proteins or fragments thereof, binding units that can bind to serum proteins, an Fc portion, and small proteins or peptides that can bind to serum proteins.

When the compounds of the invention contain one or more further binding domains or binding units (e.g. a further essentially non-functional binding domain or binding unit against TNF that provides for increased specificity against TNF, a binding domain or binding unit against a therapeutic target other than TNF, a binding domain or binding unit against a target such as human serum albumin that provides for increased half-life, and/or a binding domain or binding unit that targets the compound of the invention to a specific cell, tissue or organ and/or that allows for the compound of the invention to be internalized into a cell), these other binding domains or binding units preferably comprise one or more ISVDs, and more preferably are all ISVDs. For example and without limitation, these one or more further binding domains or binding units can be one or more Nanobodies (including a VHH, a humanized VHH and/or a camelized VHs such as camelized human VH's), a (single domain) antibody that is a VH domain or that is derived from a VH domain, a dAb that is or essentially consists of a VH domain or that is derived from a VH domain, or even a (single) domain antibody or a dAb that is or essentially consists of VL domain. In particular, these one or more binding domains or binding units, when present, may comprise one or more Nanobodies, and more in particular are all Nanobodies.

When a compound of the invention has an ISVD at its C-terminal end (which C-terminal ISVD may be a TNF binder of the invention or may for example be, if present in the compound of the invention, a further essentially non-functional ISVD against TNF that provides for increased specificity against TNF, an ISVD against a therapeutic target other than TNF, an ISVD against a target such as human serum albumin that provides for increased half-life, or an ISVD that targets the compound of the invention to a specific cell, tissue or organ and/or that allows for the compound of the invention to be internalized into a cell), then the compound of the invention (i.e. said C-terminal ISVD) preferably has a C-terminal extension X(n), which C-terminal extension may be as described herein for the TNF binders of the invention and/or as described in WO 2012/175741 or WO2015/173325.

When a compound of the invention contains, in addition to the one or more TNF binders of the invention, any further ISVDs (which one or more further ISVDs may, as mentioned, be a further essentially non-functional ISVD against TNF that provides for increased specificity against TNF, an ISVD against a therapeutic target other than TNF, an ISVD against a target such as human serum albumin that provides for increased half-life, and/or an ISVD that targets the compound of the invention to a specific cell, tissue or organ and/or that allows for the compound of the invention to be internalized into a cell), and where such further ISVDs are Nanobodies or are ISVDs that are, that essentially consist of and/or that are derived from VH sequences, then according to a preferred aspect of the invention said one or more (and preferably all) further ISVDs present in the compound of the invention will contain within their sequence one or more framework mutations that reduce binding by pre-existing antibodies. In particular, according to this aspect of the invention, such further ISVDs may contain (a suitable combination of) amino acid residues/mutations at positions 11, 89, 110 and/or 112 that are as described in WO2015/173325 and/or that essentially are as described herein for the TNF binders of the invention. In one specific aspect, when the compound of the invention has such an ISVD at its C-terminal end (i.e. does not have TNF binder of the invention at its C-terminal end), then at least said ISVD that is present at and/or forms the C-terminal end has such framework mutations that reduce binding by pre-existing antibodies (and said C-terminal ISVD will preferably also have a C-terminal extension X(n) as described herein).

As mentioned, when the compound of the invention is to have an increased half-life (i.e. compared to the monovalent TNF binder of the invention), the compound of the invention preferably contains at least one (such as one) ISVD (and in particular Nanobody) that provides for such increased half-life. Such an ISVD will usually be directed against a suitable serum protein such as transferrin and in particular against (human) serum albumin. In particular, such an ISVD or Nanobody may be a (single) domain antibody or dAb against human serum albumin as described in for example EP 2 139 918, WO 2011/006915, WO 2012/175400, WO 2014/111550 and may in particular be a serum albumin binding Nanobody as described in WO 2004/041865, WO 2006/122787, WO 2012/175400 or WO2015/173325. Particularly preferred serum albumin binding ISVDs are the Nanobody Alb-1 (see WO 2006/122787) or its humanized variants such as Alb-8 (WO 2006/122787, SEQ ID NO: 62), Alb-23 (WO 2012/175400, SEQ ID NO: 1) and other humanized (and preferably also sequence-optimized) variants of Alb-1 and/or variants of Alb-8 or Alb-23 (or more generally ISVDs that have essentially the same CDRs as Alb-1, Alb-8 and Alb-23).

Again, as mentioned, such a serum albumin binding ISVD, when present, may contain within its sequence one or more framework mutations that reduce binding by pre-existing antibodies. In particular, when such a serum albumin binding ISVD is a Nanobody or a (single) domain antibody that is, essentially consist of and/or is derived from a VH domain, the serum albumin binding ISVD may contain (a suitable combination of) amino acid residues/mutations at positions 11, 89, 110 and/or 112 that are as described in WO2015/173325 and/or that essentially are as described herein for the TNF binders of the invention. For example, WO2015/173325 describes a number of variants of Alb-1, Alb-8 and Alb-23 that contain amino acid residues/mutations at positions 11, 89, 110 and/or 112 that reduce binding by pre-existing antibodies that can be used in the compounds of the invention.

In a particular but non-limiting aspect of the invention, the invention provides a compound of the invention, such as a polypeptide of the invention, comprising besides the one or more building blocks, e.g. ISVDs, binding TNF, at least one building block binding serum albumin, such as a serum albumin binding ISVD, preferably binding human serum albumin as described herein, wherein said serum albumin binding ISVD essentially consists of 4 framework regions (FR1 to FR4, respectively) and 3 complementarity determining regions (CDR1 to CDR3 respectively), in which CDR1 is SFGMS (SEQ ID NO: 101), CDR2 is SISGSGS-DTLYADSVKG (SEQ ID NO: 102) and CDR3 is GGSLSR (SEQ ID NO: 103). Preferably, said ISVD binding human serum albumin is chosen from the group consisting of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 (cf. Table D).

Again, when such a serum albumin binding ISVD is present at the C-terminal end of a compound of the invention, the serum albumin binding ISVD (and as a result, the compound of the invention) preferably has a C-terminal extension X(n), which C-terminal extension may be as described herein for the TNF binders of the invention and/or as described in WO 2012/175741 or WO2015/173325. It also preferably has mutations that reduce the binding of pre-existing antibodies, like (a suitable combination of) the amino acid residues/mutations at positions 11, 89, 110 and/or 112 described in WO2015/173325.

However, as mentioned, other means of increasing the half-life of a compound of the invention (such as PEGylation, fusion to human albumin or a suitable fragment thereof, or the use of a suitable serum albumin-binding peptide), although less preferred, are also included in the scope of the invention.

Accordingly, in an embodiment the present invention relates to a compound as described herein, wherein said serum protein binding moiety is a non-antibody based polypeptide.

In a further embodiment the present invention relates to a compound as described herein, further comprising PEG.

Generally, when a compound of the invention has increased half-life (e.g. through the presence of a half-life increasing ISVD or any other suitable way of increasing half-life), the resulting compound of the invention preferably has a half-life (as defined herein) that is at least 2 times, preferably at least 5 times, for example at least 10 times or more than 20 times, greater than the half-life of the monovalent TNF binder of the invention (as measured in either in man and/or a suitable animal model, such as mouse or cynomolgus monkey). In particular, a compound of the invention preferably has a half-life (as defined herein) in human subjects of at least 1 day, preferably at least 3 days, more preferably at least 7 days, such as at least 10 days.

It will be clear from the disclosure herein that compounds of the invention that are based on one or more ISVDs can have different "formats", e.g. essentially be monovalent, bivalent or trivalent, can be monospecific, bispecific, trispecific etc., and can be biparatopic (as defined herein and in for example WO 2009/068625). For example, a compound of the invention can be:

(essentially) monovalent, i.e. (essentially) comprising a single TNF binder of the invention. As mentioned, when used in monovalent format, a TNF binder of the invention preferably has a C-terminal extension X(n) as further described herein. Such a compound of the invention may also be half-life extended;

(essentially) bivalent or trivalent and monospecific. Such a compound of the invention will comprise two or more ISVDs against TNF, which may be the same or different and when different may be directed against the same epitope on TNF or against different epitopes on TNF (in the latter case, so as to provide a biparatopic or multiparatopic compound of the invention). Such a compound of the invention may also be half-life extended; (essentially) bivalent, trivalent (or multivalent) and bispecific or trispecific (or multispecific). Such a compound of the invention will be directed against TNF and at least one other target. As described herein, said other target may for example be another therapeutically relevant target (i.e. other than TNF) so as to provide a compound of the invention that is bispecific with regards to TNF and said other therapeutic target. Said other target may also be a target that provides for increased half-life (such as human serum albumin), so as to provide a compound of the invention that has increased half-life. As also mentioned herein, such other target may allow also for the compound of the invention to be targeted to specific cells, tissues or organs or may allow for the compound of the invention to be internalized into a cell. It is also possible to combine these approaches/ISVDs, for example to provide a compound of the invention that is bispecific for TNF and for at least one other therapeutically relevant target and that is half-life extended.

Again, preferably, when these compounds of the invention contain one or more ISVDs other than the at least one TNF binder of the invention, at least one and preferably all of these other ISVDs will contain within its sequence one or more framework mutations that reduce binding by pre-existing antibodies (such as, in particular, a combination of amino acid residues/mutations at positions 11, 89, 110 and/or 112 that is as described herein for the TNF binders of the invention and/or as generally described in WO2015/173325). Also, when such compounds of the invention have a TNF binder of the invention at their C-terminal end, then said C-terminal TNF binder (and as a result, the compound of the invention) will preferably have a C-terminal extension X(n) as described herein. Similarly, when such compounds of the invention have another ISVD at their C-terminal end (i.e. not a TNF binder of the invention, but for example a half-life extending ISVD), then said C-terminal ISVD (and as a result, the compound of the invention) will preferably have a C-terminal extension X(n) as described herein and/or will contain within its sequence one or more framework mutations that reduce binding by pre-existing antibodies (again, as further described herein and in WO2015/173325).

As will be clear to the skilled person, when a compound of the invention is intended for topical use (e.g. on the skin or in the eye) or is for example meant to have a (localized) therapeutic action somewhere in for example the GI tract (Gastro-intestinal; e.g. after oral administration or administration by suppository) or in the lungs (e.g. after administration by inhalation) or is otherwise meant to be directly applied to its intended place of action (for example, by direct injection), a compound of the invention will usually not require half-life extension. Also, for treatment of certain acute conditions or indications, it may be preferable not to have a prolonged half-life. In these cases, the use of a monovalent compound of the invention or of a compound of the invention (comprising the TNF binder) without half-life extension (for example, a compound of the invention that is bivalent or biparatopic with respect to TNF) is preferred.

Some preferred, but non-limiting examples of such compounds of the invention are schematically represented in Table C-1 below, and each of these forms a further aspect of the invention. Other examples of suitable compounds of the invention without half-life extension will be clear to the skilled person based on the disclosure herein.

As will be clear to the skilled person, when a compound of the invention is intended for systemic administration and/or for prevention and/or treatment of a chronic disease or disorder, it will usually be preferred that said compound of the invention has increased half-life (as defined herein), i.e. compared to the TNF binder(s) present in such compound of the invention. More preferably, such a compound of the invention will contain a half-life extending ISVD such as, preferably, an ISVD and in particular a Nanobody binding to human serum albumin (as described herein).

Some preferred, but non-limiting examples of such compounds of the invention are schematically represented in Table C-2 below, and each of these forms a further aspect of the invention. Other examples of suitable compounds of the invention with half-life extension will be clear to the skilled person based on the disclosure herein. Generally, for compounds of the invention with half-life extension, the presence of a C-terminal extension is much preferred.

The immunoglobulin single variable domains may be used as a "building block" for the preparation of a compound, such as a polypeptide of the invention, which may optionally contain one or more further "building blocks", such as ISVDs, against the same or another epitope on TNF and/or against one or more other antigens, proteins or targets than TNF, e.g. building blocks having a therapeutic mode of action.

Generally, compounds, polypeptides or constructs that comprise or essentially consist of a single building block, single immunoglobulin single variable domain or single Nanobody will be referred to herein as "monovalent" compounds or "monovalent" polypeptides or as "monovalent constructs", respectively. Compounds, polypeptides or constructs that comprise two or more building blocks or binding units (such as e.g., ISVDs) will also be referred to herein as "multivalent" compounds, polypeptides or constructs, and the building blocks/ISVDs present in such compounds, polypeptides or constructs will also be referred to herein as being in a "multivalent format". For example, a "bivalent" compound or polypeptide may comprise two immunoglobulin single variable domains, optionally linked via a linker sequence, whereas a "trivalent" compound or polypeptide may comprise three immunoglobulin single variable domains, optionally linked via two linker sequences; whereas a "tetravalent" compound or polypeptide may comprise four immunoglobulin single variable domains, optionally linked via three linker sequences, etc.

In a multivalent compound, polypeptide or construct, the two or more ISVDs, such as Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. Compounds, polypeptides or constructs that contain at least two building blocks (such as e.g., ISVDs) in which at least one building block is directed against a first antigen (i.e., TNF) and at least one building block is directed against a second antigen (i.e., different from TNF) will also be referred to as "multispecific" compounds, polypeptides or constructs, respectively, and the building blocks (such as e.g., ISVDs) present in such compounds, polypeptides or constructs will also be referred to herein as being in a "multispecific format". Thus, for example, a "bispecific" compound or polypeptide of the invention is a compound or polypeptide that comprises at least one ISVD directed against a first antigen (i.e., TNF) and at least one further ISVD directed against a second antigen (i.e., different from TNF), whereas a "trispecific" compound or polypeptide of the invention is a compound or polypeptide that comprises at least one ISVD directed against a first antigen (i.e., TNF), at least one further ISVD directed against a second antigen (i.e., different from TNF) and at least one further ISVD directed against a third antigen (i.e., different from both TNF and the second antigen); etc.

"Multiparatopic" compounds, "multiparatopic" polypeptides and "multiparatopic" constructs, such as e.g., "biparatopic" compounds, polypeptides or constructs, or "triparatopic" compounds, polypeptides or constructs, comprise or essentially consist of two or more building blocks that each have a different paratope.

Accordingly, the ISVDs of the invention that bind TNF can be in essentially isolated form (as defined herein), or they may form part of a compound, polypeptide or construct, which may comprise or essentially consist of one or more ISVDs that bind TNF and which may optionally further comprise one or more further amino acid sequences (all optionally linked via one or more suitable linkers). The present invention relates to a compound, polypeptide or construct that comprises or essentially consists of at least one ISVD according to the invention, such as one or more ISVDs of the invention (or suitable fragments thereof), binding TNF as defined herein.

The one or more ISVDs of the invention can be used as a binding unit or building block in such a compound, polypeptide or construct, so as to provide a monovalent, multivalent or multiparatopic compound, polypeptide or construct of the invention, respectively, all as described herein. The present invention thus also relates to a compound or polypeptide which is monovalent comprising or essentially consisting of one monovalent polypeptide or ISVD of the invention. The present invention thus also relates to a compound, polypeptide or construct which is a multivalent compound, multivalent polypeptide or multivalent construct, respectively, such as e.g., a bivalent or trivalent compound, polypeptide or construct comprising or essentially consisting of two or more ISVDs of the invention (for multivalent and multispecific compounds or polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998).

The invention further relates to a multivalent compound or polypeptide (also referred to herein as a "multivalent compound(s) of the invention" and "multivalent polypeptide(s) of the invention", respectively) that comprises or (essentially) consists of at least one ISVD (or suitable fragments thereof) directed against TNF, preferably human TNF, and one additional ISVD.

In an aspect, in its simplest form, the multivalent compound, polypeptide or construct of the invention is a bivalent compound, polypeptide or construct of the invention comprising a first ISVD, such as a Nanobody, directed against TNF, and an identical second ISVD, such as a Nanobody, directed against TNF, wherein said first and said second ISVDs, such as Nanobodies, may optionally be linked via a linker sequence (as defined herein). In its simplest form a multivalent compound, polypeptide or construct of the invention may be a trivalent compound, polypeptide or construct of the invention, comprising a first ISVD, such as Nanobody, directed against TNF, an identical second ISVD, such as Nanobody, directed against TNF and an identical third ISVD, such as a Nanobody, directed against TNF, in which said first, second and third immunoglobulin ISVDs, such as Nanobodies, may optionally be linked via one or more, and in particular two, linker sequences.

In another aspect, the multivalent compound, polypeptide or construct of the invention may be a bispecific compound, polypeptide or construct of the invention, comprising a first ISVD, such as a Nanobody, directed against TNF, and a second ISVD, such as a Nanobody, directed against a second antigen, in which said first and second ISVDs, such as Nanobodies, may optionally be linked via a linker sequence (as defined herein); whereas a multivalent compound, polypeptide or construct of the invention may also be a trispecific compound, polypeptide or construct of the invention, comprising a first ISVD, such as a Nanobody, directed against TNF, a second ISVD, such as a Nanobody, directed against a second antigen and a third ISVD, such as a Nanobody, directed against a third antigen, in which said first, second and third ISVDs, such as Nanobodies, may optionally be linked via one or more, and in particular two, linker sequences.

In a particular aspect, the compound, polypeptide or construct of the invention is a trivalent, bispecific compound, polypeptide or construct, respectively. A trivalent, bispecific compound, polypeptide or construct of the invention in its simplest form may be a trivalent compound, polypeptide or construct of the invention (as defined herein), comprising two identical ISVDs, such as Nanobodies, against TNF and a third ISVD, such as a Nanobody, directed against another antigen, in which said first, second and third ISVDs, such as Nanobodies, may optionally be linked via one or more, and in particular two, linker sequences.

In another aspect, the compound or polypeptide of the invention is a bispecific compound or polypeptide. A bispecific compound, polypeptide or construct of the invention in its simplest form may be a bivalent compound, polypeptide or construct of the invention (as defined herein), comprising an ISVD, such as a Nanobody, against TNF and a second ISVD, such as a Nanobody, directed against another antigen, in which said first and second ISVDs, such as Nanobodies, may optionally be linked via a linker sequence.

In a preferred aspect, the multivalent compound, polypeptide or construct of the invention comprises or essentially consists of two or more immunoglobulin single variable domains directed against TNF. In an aspect, the invention relates to a compound, polypeptide or construct that comprises or essentially consists of at least two ISVDs according to the invention, such as 2, 3 or 4 ISVDs (or suitable fragments thereof), binding TNF. The two or more ISVDs may optionally be linked via one or more peptidic linkers.

In a preferred aspect, the compound, polypeptide or construct of the invention comprises or essentially consists of at least two ISVDs, wherein said at least two ISVDs can be the same or different, but of which at least one ISVD is directed against TNF, such as binding TNF.

In a particular aspect, the compound, polypeptide or construct of the invention comprises or essentially consists of at least two ISVDs, wherein at least two ISVDs are independently chosen from the group consisting of SEQ ID NO:s 8-41 and 61-66 and 69.

The relative affinities may depend on the location of the ISVDs in the resulting compound, polypeptide or construct of the invention. It will be appreciated that the order of the ISVDs in a compound or polypeptide of the invention (orientation) can be chosen according to the needs of the person skilled in the art. The order of the individual ISVDs as well as whether the compound or polypeptide comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the compound, polypeptide or construct of the invention can be (from N-terminus to C-terminus): (i) ISVD 1 (e.g. Nanobody 1)-[linker]-ISVD 2 (e.g. Nanobody 2); or (ii) ISVD 2 (e.g. Nanobody 2)-[linker]-ISVD 1 (e.g. Nanobody 1); (wherein the linker is optional). All orientations are encompassed by the invention. Compounds, polypeptides and constructs that contain an orientation of ISVDs that provides desired binding characteristics can be easily identified by routine screening.

In the compounds or constructs of the invention, such as the polypeptides of the invention, the two or more building blocks, such as e.g. ISVDs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific compounds or polypeptides will be clear to the skilled person, and may generally be any linker or spacer used in the art to link amino acid sequences. Preferably, said linker or spacer is suitable for use in constructing compounds, constructs, proteins or polypeptides that are intended for pharmaceutical use.

In an embodiment, the invention relates to a compound or polypeptide as defined herein, wherein said ISVDs are directly linked to each other or are linked via a linker. In another embodiment, the invention relates to a compound or polypeptide as defined herein, wherein a first ISVD and/or a second ISVD and/or possibly a third ISVD and/or possibly an ISVD binding serum albumin are linked via a linker.

Some particularly preferred linkers and spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as a Nanobody, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table E, e.g. SEQ ID NO:s 85-100.

Some other particularly preferred linkers are poly-alanine (such as AAA), as well as the linkers GS30 (SEQ ID NO: 85 in WO 06/122825) and GS9 (SEQ ID NO: 84 in WO 06/122825).

In an embodiment, the invention relates to a compound as defined herein, wherein said linker is chosen from the group consisting of linkers of SGS, 7GS, 9GS, 10GS, 15GS, 18GS, 20GS, 25GS, 30GS, 35GS and 40GS.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final compound or construct of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific compound or construct of the invention, such as the polypeptide of the invention, optionally after some limited routine experiments.

For example, in multivalent compounds or polypeptides of the invention that comprise building blocks, such as ISVDs or Nanobodies directed against TNF and another target, the length and flexibility of the linker are preferably such that it allows each building block, such as an ISVD, of the invention present in the polypeptide to bind to its cognate target, e.g. the antigenic determinant on each of the targets. Again, based on the disclosure herein, the skilled person will be able to determine the optimal linker(s) for use in a specific compound or construct of the invention, such as a polypeptide of the invention, optionally after some limited routine experiments.

It is also within the scope of the invention that the linker(s) used confer one or more other favourable properties or functionality to the compounds or constructs of the invention, such as the polypeptides of the invention, and/or provide one or more sites for the formation of derivatives and/or for the attachment of functional groups (e.g. as described herein for the derivatives of the ISVDs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific compound, polypeptide or construct of the invention, optionally after some limited routine experiments.

Finally, when two or more linkers are used in the compounds or constructs such as polypeptides of the invention, these linkers may be the same or different. Again, based on the disclosure herein, the skilled person will be able to determine the optimal linkers for use in a specific compound or construct or polypeptide of the invention, optionally after some limited routine experiments.

For a general description of multivalent and multispecific compounds and polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 1996/

34103, WO 1999/23221, WO 2004/041862, WO 2006/122786, WO 2008/020079, WO 2008/142164 or WO 2009/068627.

The invention also relates to nucleotide sequences or nucleic acids that encode amino acid sequences, TNF binders, polypeptides, fusion proteins, compounds and constructs described herein. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 2004/041862, WO 2006/122786, WO 2008/020079, WO 2008/142164 or WO 2009/068627.

In an aspect the invention relates to a nucleic acid encoding an ISVD, polypeptide, compound or construct according to the invention.

In another aspect the invention relates to an expression vector comprising a nucleic acid according to the invention.

The invention also relates to hosts or host cells that contain such nucleotide sequences or nucleic acids, and/or that express (or are capable of expressing), the amino acid sequences, TNF binders, polypeptides, fusion proteins, compounds and constructs described herein. Again, such host cells can be generally as described in the published patent applications of Ablynx N.V., such as for example WO 2004/041862, WO 2006/122786, WO 2008/020079, WO 2008/142164 or WO 2009/068627.

In an aspect the invention relates to a host or host cell comprising a nucleic acid according to the invention, or an expression vector according to the invention.

The invention also relates to a method for preparing an amino acid sequence, TNF binders, polypeptides, fusion protein, compounds or construct as described herein, which method comprises cultivating or maintaining a host cell as described herein under conditions such that said host cell produces or expresses an amino acid sequence, TNF binders, polypeptides, fusion protein, compounds or construct as described herein, and optionally further comprises isolating the amino acid sequence, TNF binders, polypeptides, fusion protein, compounds or construct so produced. Again, such methods can be performed as generally described in the published patent applications of Ablynx N.V., such as for example WO 2004/041862, WO 2006/122786, WO 2008/020079, WO 2008/142164 or WO 2009/068627.

In a particular aspect the invention relates to a method for producing an ISVD according to the invention or a compound according to the invention or a polypeptide according to the invention, said method at least comprising the steps of:
a) expressing, in a suitable host cell or host organism or in another suitable expression system, a nucleic acid sequence as defined herein; optionally followed by:
b) isolating and/or purifying the ISVD according to the invention, the compound according to the invention or the polypeptide according to the invention, respectively.

The invention also relates to a composition that comprises at least one amino acid sequence, TNF binder, polypeptide, fusion protein, compound or construct as described herein.

The invention also relates to a pharmaceutical composition that comprises at least one amino acid sequence, TNF binder, polypeptide, fusion protein, compound or construct as described herein, and optionally at least one pharmaceutically acceptable carrier, diluent or excipient and/or adjuvant, and optionally comprises one or more further pharmaceutically active polypeptides and/or compounds. Such preparations, carriers, excipients and diluents may generally be as described in the published patent applications of Ablynx N.V., such as for example WO 2004/041862, WO 2006/122786, WO 2008/020079, WO 2008/142164 or WO 2009/068627.

When amino acid sequences, TNF binders, polypeptides, fusion proteins, compounds or constructs described herein have an increased half-life, they are preferably administered to the circulation. As such, they can be administered in any suitable manner that allows the amino acid sequences, TNF binders, polypeptides, fusion proteins, compounds or constructs to enter the circulation, such as intravenously, via injection or infusion, or in any other suitable manner (including oral administration, subcutaneous administration, intramuscular administration, administration through the skin, intranasal administration, administration via the lungs, etc.) that allows the amino acid sequences, TNF binders, polypeptides, fusion proteins, compounds or constructs to enter the circulation. Suitable methods and routes of administration will be clear to the skilled person, again for example also from the teaching of the published patent applications of Ablynx N.V., such as for example WO 2004/041862, WO 2006/122786, WO 2008/020079, WO 2008/142164 or WO 2009/068627.

In another aspect, the invention relates to a method for the prevention and/or treatment of at least one disease or disorder that can be prevented or treated by the use of a an amino acid sequence, TNF binder, polypeptide, fusion protein, compound or construct as described herein, which method comprises administering, to a subject in need thereof, a pharmaceutically active amount of an amino acid sequence, TNF binder, polypeptide, fusion protein, compound or construct of the invention, and/or of a pharmaceutical composition comprising the same. The diseases and disorders that can be prevented or treated by the use of a polypeptide, fusion protein, compound or construct as described herein will generally be the same as the diseases and disorders that can be prevented or treated by the use of the therapeutic moiety that is present in the polypeptide, fusion protein, compound or construct of the invention. Particularly, the present invention relates to compound, composition, construct, polypeptide, TNF binder or ISVD as described herein for use as a medicament.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated. A composition of the invention need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

In one embodiment, an indication that a therapeutically effective amount of a composition has been administered to the patient is a sustained improvement over baseline of an indicator that reflects the severity of the particular disorder. The pharmaceutical compositions of the present invention comprise a therapeutically effective amount of an ISVD, compound or polypeptide of the present invention formulated together with one or more pharmaceutically acceptable carriers or excipients. By a "therapeutically effective amount" of an ISVD, compound or polypeptide of the invention is meant an amount of the composition which confers a therapeutic effect on the treated subject, at a reasonable benefit/risk ratio applicable to any medical treatment. The therapeutic effect is sufficient to "treat" the patient as that term is used herein.

In an embodiment, the present invention relates to a composition, construct, compound, TNF binder, ISVD or polypeptide as described herein, for use in the treatment of a disease and/or disorder of the digestive tract.

In an embodiment, the present invention relates to a composition, construct, compound, TNF binder, ISVD or polypeptide as described herein, wherein said disease and/or disorder of the digestive tract is inflammatory bowel disease (IBD), irritable bowel syndrome, Crohn's disease, ulcerative colitis, mucositis, aphthous stomatitis, celiac disease, trauma to the digestive tract and cancers to the digestive tract.

Patients with irritable bowel syndrome have altered intestinal permeability despite having little or no detectable histological changes in the intestines (Dunlop Am J Gastroenterol. 2006 June; 101(6): 1288-94). Patients with celiac disease have altered intestinal permeability and characteristic damage to the villi of the small intestine that is distinguishable from IBD. Inflammatory bowel disease is thought to result from a dysregulated immune response initiated by microbial-host interactions. The immune system responds to non-pathogenic commensal bacteria generating chronic inflammation. Similarly, in necrotizing enterocolitis, a stressed underdeveloped immune system generates an inappropriate response to normal intestinal bacteria, inducing a potentially fatal form of colitis (filling et al, 2006, J Immunol, 177, 3273-82).

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of an amino acid sequence, TNF binder, polypeptide, fusion protein, compound or construct of the invention, and/or of a pharmaceutical composition comprising the same.

The amino acid sequence, TNF binder, polypeptide, fusion protein, compound or construct and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, TNF binder, polypeptide, fusion protein, compound or construct of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, TNF binders, polypeptides, fusion proteins, compounds or constructs of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used, the amino acid sequences, TNF binders, polypeptides, fusion proteins, compounds or constructs of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, TNF binder, polypeptide, fusion protein, compound or construct of the invention will be used. It is however within the scope of the invention to use two or more amino acid sequences, TNF binders, polypeptides, fusion proteins, compounds or constructs of the invention in combination.

The amino acid sequences, TNF binder, polypeptides, fusion proteins, compounds or constructs of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, TNF binders, polypeptides, fusion proteins, compounds or constructs of the invention may be used in combination with other pharmaceutically active compounds or principles that are or can be used for the prevention and/or treatment of the diseases and disorders that can be prevented or treated with the amino acid sequences, TNF binders, polypeptides, fusion proteins, compounds or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

As the amino acid sequences, TNF binders, polypeptides, fusion proteins, compounds or constructs of the invention are capable of binding to TNF, they can in particular be used for the prevention and or treatment of diseases or disorders that can be treated by other biological drugs (like antibodies, for example adalimumab/HUMIRA™ or Infliximab/REMICADE™) that are capable of binding to TNF and/or modulating TNF. Such diseases and disorders will be clear to the skilled person. The TNF binders of the invention can in particular be used for the prevention and treatment of the diseases and disorders mentioned in WO 2004/041862 and WO 2006/122786.

As mentioned, one specific aspect of the invention relates to TNF binders of the invention that are in monovalent format. These monovalent TNF binders of the invention are particularly suitable for topical applications (including applications on the skin, in the GI tract or the lungs) and/or for topical administration (e.g. to the skin), oral administration (e.g. to the GI tract), administration by suppository (again, e.g. to the GI tract) and/or administration to the lungs (e.g. by inhalation). As such, they can be used for the prevention and/or treatment of diseases and disorders of the skin, lungs or GI tract that can be prevented or treated by application of a TNF inhibitor to the skin, lungs or GI tract, respectively (such as inflammatory and/or autoimmune diseases affecting the skin, lungs or GI tract, respectively).

In an embodiment, the present invention relates to a composition, compound, construct, TNF binder, polypeptide or ISVD as described herein, wherein the composition, the compound, the construct, the TNF binder, the polypeptide or the ISVD is administered topically to the digestive tract.

In an embodiment, the present invention relates to a composition, compound, construct, TNF binder, polypeptide or ISVD as described herein, wherein the composition, compound, construct, TNF binder, polypeptide or ISVD is administered orally in a dosage form suitable for oral administration to the gastrointestinal tract (GI).

In an embodiment, the present invention relates to a composition, compound, construct, TNF binder, polypeptide or ISVD as described herein, wherein the composition, compound, construct, TNF binder, polypeptide or ISVD is administered in a dosage form for oral administration to the GI tract wherein the dosage form is selected from tablets, capsules, pills powders, granules, emulsions, microemulsions, solutions, suspensions, syrups and elixirs.

In an embodiment, the present invention relates to a composition, compound, construct, TNF binder, polypeptide or ISVD as described herein, wherein the composition, compound, construct, TNF binder, polypeptide or ISVD is administered rectally for treatment of a disease or disorder of the digestive tract.

In an embodiment, the present invention relates to a composition, compound, construct, TNF binder, polypeptide or ISVD as described herein, wherein the composition, compound, construct, TNF binder, polypeptide or ISVD is administered rectally in a dosage form for rectal administration, preferably selected from suppositories and enemas.

In an embodiment, the present invention relates also to a composition, compound, construct, TNF binder, polypeptide or ISVD as described herein, wherein the composition, compound, construct, TNF binder, polypeptide or ISVD is administered parenterally by subcutaneous injection, intracutaneous injection, intravenous injection, intramuscular injection, intralesional injection, or infusion techniques.

Some specific but non-limiting examples of such diseases and disorders are diseases or disorders of the GI tract such as inflammatory bowel disease (IBD) Crohn's disease, irritable bowel syndrome, ulcerative colitis, mucositis, aphthous stomatitis, celiac disease, trauma to the digestive tract and/or cancers to the digestive tract. As mentioned, when used for these purposes, the monovalent TNF binders of the invention preferably have a D (or E1D) mutation at position 1 and a C-terminal extension (such as a C-terminal alanine), and the TNF binders of SEQ ID NO:s 40, 39, 36, 64, 69, 37, 38, 41, 62-63, and 65-66 in particular SEQ ID NO:s 40, 39, 36, 64 and 69, most particularly SEQ ID NO: 40 are preferred examples of TNF binders of the invention that are particularly suited for these purposes.

Thus, in a further aspect, the invention relates to a TNF binder of the invention (as described herein) that is essentially in monovalent format (and that preferably as a D or E1D mutation at position 1 and a C-terminal extension such as C-terminal alanine) for use in the prevention and treatment of diseases and disorders of the skin, lungs or GI tract, and in particular in the prevention and treatment of inflammatory and/or autoimmune diseases affecting the skin, lungs or GI tract. Said TNF binder is preferably chosen from the group consisting of SEQ ID NO:s 40, 39, 36, 64, 69, 37, 38, 41, 62-63, and 65-66, in particular SEQ ID NO:s 40, 39, 36, 64 and 69, most particularly SEQ ID NO: 40.

The invention also relates to a TNF binder of the invention (as described herein) that is essentially in monovalent format (and that preferably as a D or E1D mutation at position 1 and a C-terminal extension such as C-terminal alanine) for use in the prevention and treatment of diseases or disorders of the GI tract such as inflammatory bowel disease (IBD) Crohn's disease, irritable bowel syndrome, ulcerative colitis, mucositis, aphthous stomatitis, celiac disease, trauma to the digestive tract and/or cancers to the digestive tract, in particular IBD and Crohn's disease. Again, said TNF binder is preferably chosen from the group consisting of SEQ ID NO:s 40, 39, 36, 64, 69, 37, 38, 41, 62-63, and 65-68, in particular SEQ ID NO:s 40, 39, 36, 64 and 69, most particularly SEQ ID NO: 40.

The invention also relates to a pharmaceutical composition that is intended for (and/or suitable for) topical application to the skin, administration by inhalation or other administration to the lungs, and/or oral administration, rectal administration or other administration to the GI tract, that comprises a TNF binder of the invention that essentially is in monovalent format (and that preferably as a D or E1D mutation at position 1 and a C-terminal extension such as C-terminal alanine). Again, said TNF binder is preferably chosen from the group consisting of 40, 39, 36, 64, 69, 37, 38, 41, 62-63, and 65-68, in particular SEQ ID NO:s 40, 39, 36, 64 and 69, most particularly SEQ ID NO: 40. The invention also relates to a method for the prevention or treatment of a disease or disorder of the skin, which method comprises applying to the skin of a subject in need of such treatment a TNF binder of the invention that essentially is in monovalent format (and that preferably as a D or E1D mutation at position 1 and a C-terminal extension such as C-terminal alanine) or a composition comprising such a monovalent TNF binder.

The invention also relates to a method for the prevention or treatment of a disease or disorder of the skin, which method comprises administering (e.g. by inhalation) to the lungs of a subject in need of such treatment a TNF binder of the invention that essentially is in monovalent format (and that preferably as a D or E1D mutation at position 1 and a C-terminal extension such as C-terminal alanine) or a composition comprising such a monovalent TNF binder.

The invention also relates to a method for the prevention or treatment of a diseases or disorders of the GI tract such as inflammatory bowel disease (IBD) Crohn's disease, irritable bowel syndrome, ulcerative colitis, mucositis, aphthous stomatitis, celiac disease, trauma to the digestive tract and/or cancers to the digestive tract, in particular IBD or Crohn's disease, which method comprises administering (e.g. oral or rectal administration) to the GI tract of a subject in need of such treatment a TNF binder of the invention that essentially is in monovalent format (and that preferably as a D or E1D mutation at position 1 and a C-terminal extension such as C-terminal alanine) or a composition comprising such a monovalent TNF binder.

As mentioned before, at sites of inflammation the mucosal barrier of the digestive tract is often compromised, because of which orally administered proteins can enter intestinal tissues and the systemic circulation. In an embodiment, the invention thus also relates to a composition, compound, construct, TNF binder, polypeptide or ISVD as described herein, wherein the composition, compound, construct, TNF binder, polypeptide or ISVD reaches the intestinal tissues and systemic circulation of a patient.

Other aspects, embodiments, advantages and applications of the invention will become clear from the further description herein.

The invention will now be further described by means of the following non-limiting preferred aspects, examples and figures, in which:

FIG. 1 is a table listing some of the amino acid positions that will be specifically referred to herein and their numbering according to some alternative numbering systems (such as Aho and IMGT);

FIG. 2 shows an alignment of SEQ ID NOs: 1, 59 and 58;

Figure 6:
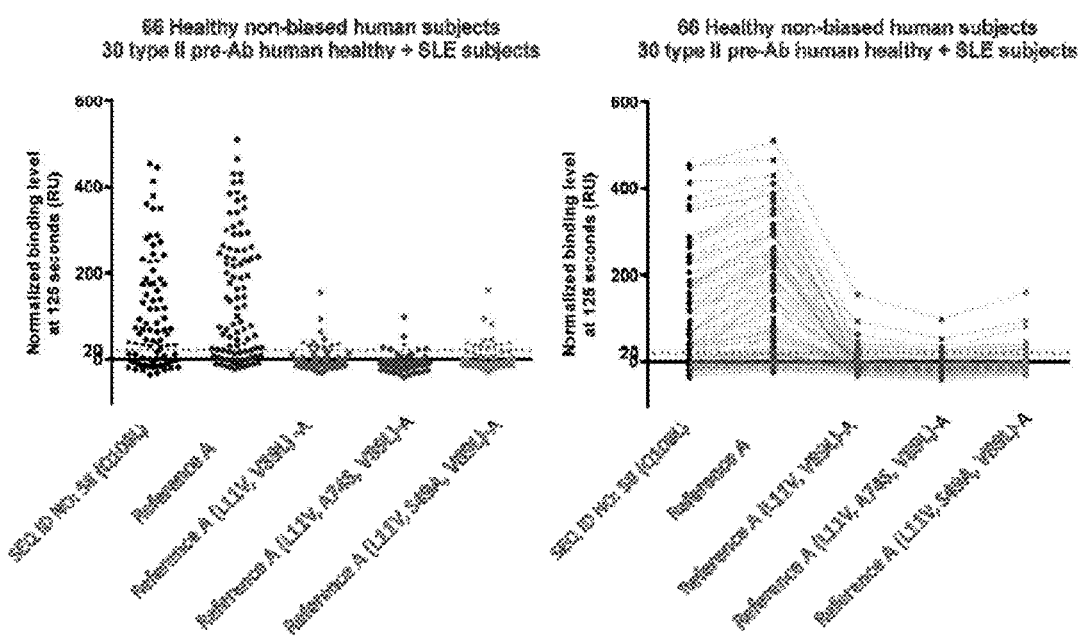

FIG. 3 lists the amino acid sequences referred to herein;

Figure 4:
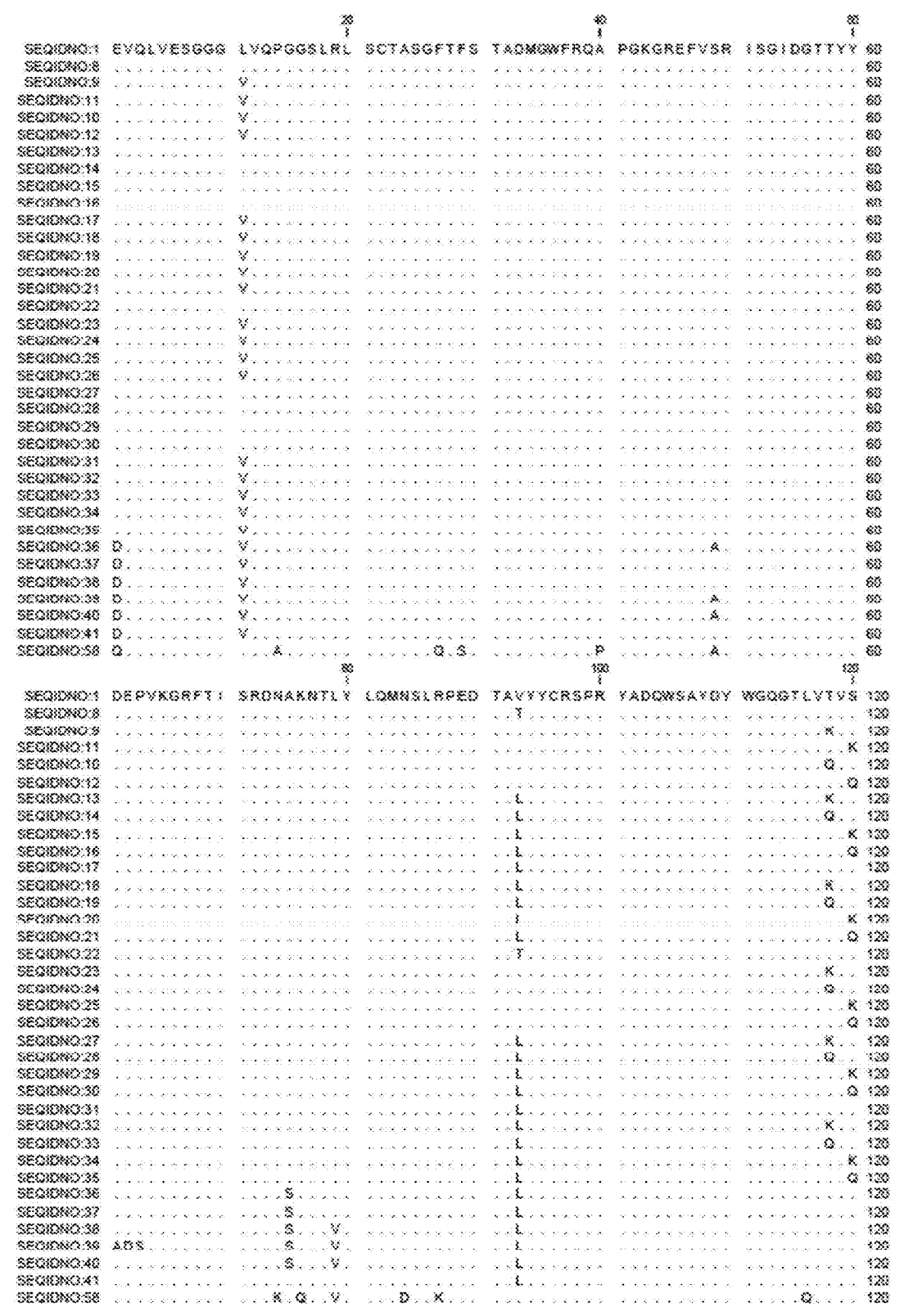

FIG. 4 shows an alignment of SEQ ID NOs: 1, 8 to 41 and 58;

FIG. 5 shows an alignment of SEQ ID NOs: 1, 31 and 36 to 41;

FIG. 6 shows two corresponding plots of data points obtained in Example 1 when 96 serum samples (66 from human healthy subjects and 30 from SLE patients) were tested for binding to the following amino acid sequences: SEQ ID NO:58 (with Q108L mutation), Reference A, Reference A (L11V, V89L)-Ala, Reference A (L11V, A74S, V89L)-Ala and Reference A (L11V, 549A, V89L)-Ala. Each dot represents the binding level for one of the 96 samples tested. The data points shown in the right hand panel and the left hand panel are the same; in the right hand panel the data points measured with each individual sample for each of the compounds tested (i.e. to SEQ ID NO:58 (Q108L), Reference A, Reference A (L11V, V89L)-A, Reference A (L11V, A74S, V89L)-A and Reference A (L11V, 549A, V89L)-A) are connected by means of a line (as a result, the declination of the line gives an indication of the extent to which binding by pre-existing antibodies is reduced when the mutations of the invention and the C-terminal alanine are introduced);

FIG. 7 is a table listing the binding data (5 columns giving normalized PreAb binding levels (RU at 125 seconds) and 4 columns giving percentage of reduction in PreAb binding compared to Reference A of the data points compiled in FIG. 6.

Figure 8C:
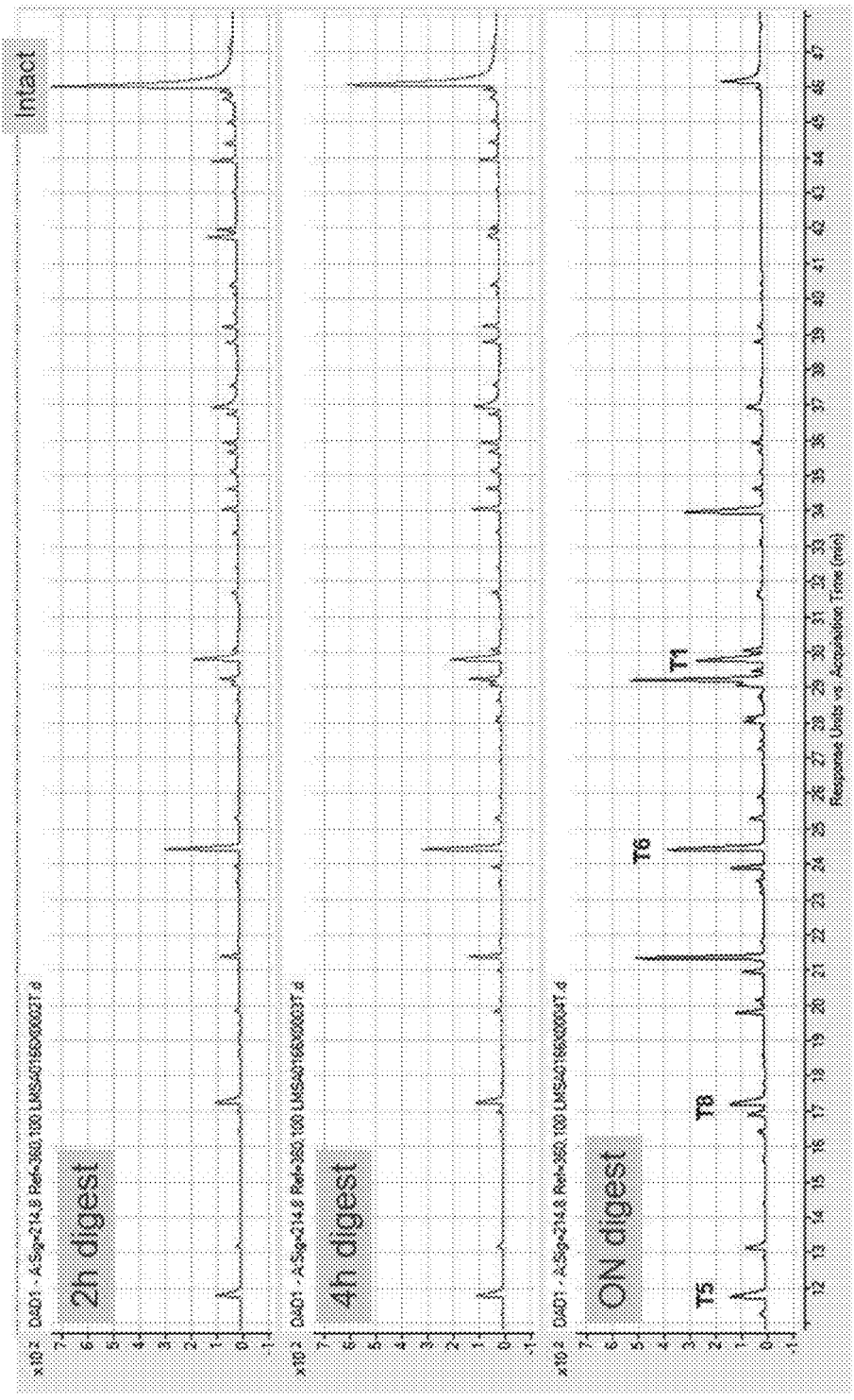

FIG. 8A: Predicted ("P") and Experimentally ("E") determined trypsin and chymotrypsin cleavage sites based on A016600015 sequence. FIG. 8B: A016600015 analysis on Coomassie stained SDS PAGE gel. FIG. 8C: Exemplary result of a tryptic digest analysis via RPC LC-MS of A016600015 sequence.

Figure 9:
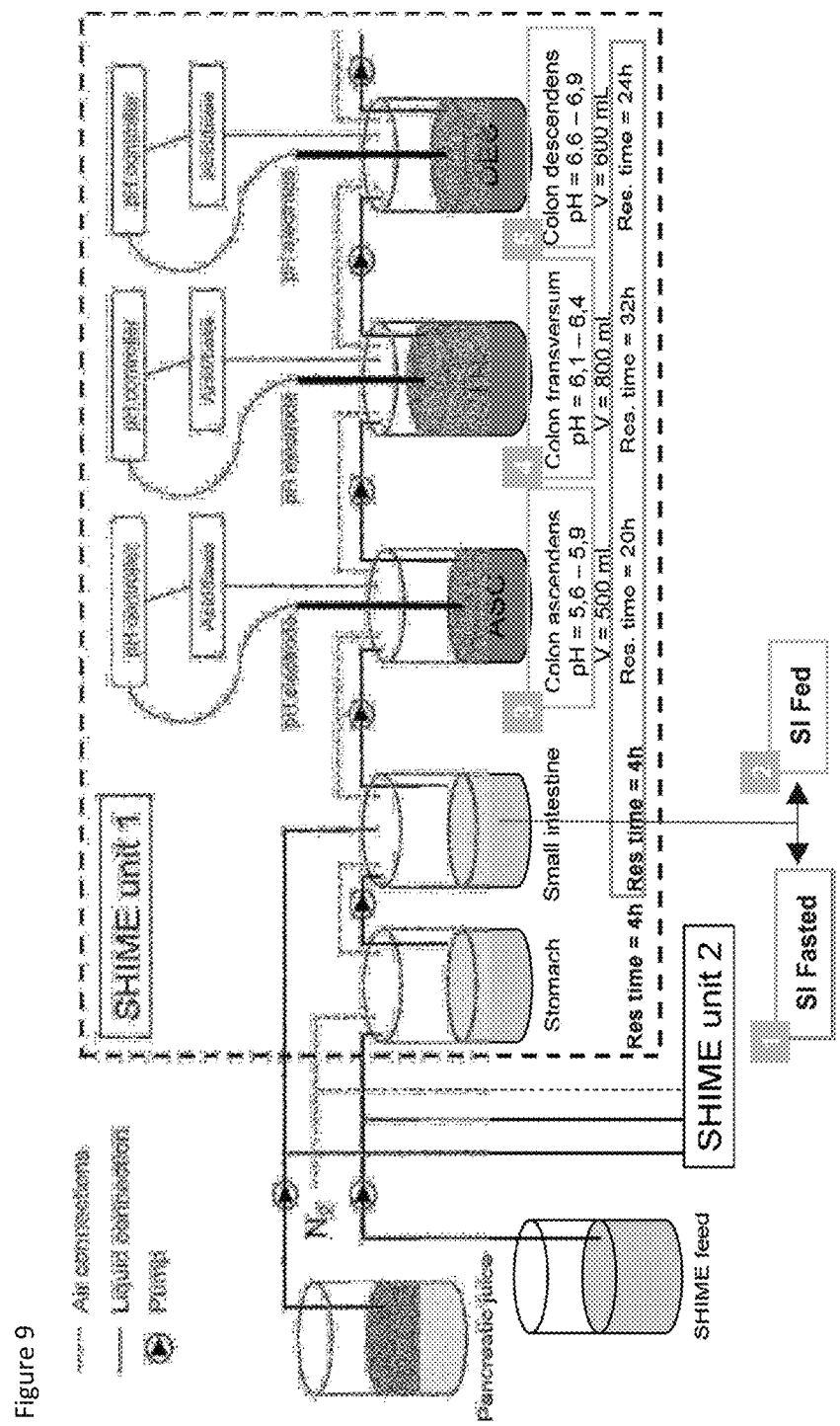

FIG. 9 schematic depiction of SHIME model.

FIG. 10 competition FACS on HEK293 H-mTNF cells treated with Enbrel (EC30=0.02 nM; panel A) and Enbrel (EC90=0.2 nM; panel B). IRR000027=irrelevant Nanobody.

Figure 11:
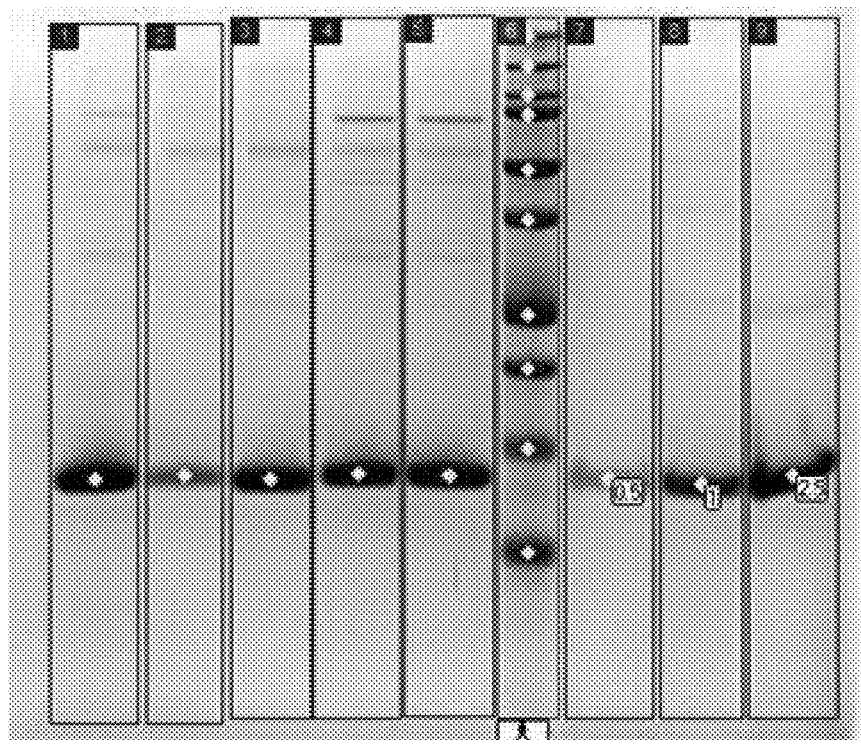

FIG. 11 shows expression results of A016600021, A016600039 and A016600040 on a 12% NuPage Bis-Tris gel under non-reducing conditions, 5 µl sample was applied. Lanes are as follows: (1) A016600021; (2) A016600039; (3) A016600040; (4) irrelevant comparator; (5) irrelevant comparator; (6) Precision Plus Protein Standard (BioRad); (7) Standard 0.5 µg; (8) Standard 1.0 µg; (9) Standard 2.5 µg.

EXAMPLES

The present inventors set out to optimize the amino acid sequence ("Sequence Optimization") of TNF-binders. In this case, the TNF-binders are intended for oral administration, because of which the TNF-binders should preferably be protease stable. Moreover, in the process of sequence optimisation it is also intended to (1) humanize the TNF-binders; (2) knock out potential epitopes of pre-existing antibodies; as well as (3) knock out sites for post-translational modifications (PTM). On the same time these characteristics should be brought into conformity with the functional characteristics of the TNF-binders, i.e. inhibiting TNFα, which should preferably be about the same or even ameliorated.

Example 1: Nanobody Production in *Pichia pastoris* and Purification Via Protein-A Binding

*Pichia pastoris* X33 cells containing the anti-TNFα Nanobody constructs were grown (30° C., 250 rpm) 24 well plates (24 mL) in a BGCM citrate buffer. After two days, the medium was switched to a methanol containing buffer (BMCM citrate) to induce the expression. Fresh methanol was added on a regular basis to compensate for the methanol consumption and evaporation, and the medium was harvested after two days. The Nanobodies were purified via capturing on protein-A column (Poros) or MEP Hypercel (Pall) followed by elution in Glycine buffer according to manufacturer's instructions. Nanobodies were subsequently desalted towards PBS using a 2 mL Zebaspin column (Pierce). Fractions were concentrated using VivaSpin columns (MWCO 5000, PES). Concentrations of the Nanobody fractions were measured using the Trinean Dropsense. Concentration was based on OD280 measurement with normalization for OD340 values. The purity and integrity of the Nanobodies was verified by SDS-PAGE and MS analysis using a Reversed Phase HPLC system coupled to an ESI-Q-TOF mass spectrometer (Q-TOF Ultimate (Waters).

Example 2: Humanization

The protein sequences of the TNF-binders of the present invention were eventually retrieved from llamas and are partially distinct from homologous antibodies occurring naturally in humans. Therefore, these TNF-binders are potentially immunogenic when administered to human patients.

Generally, for humanization purposes the Nanobody sequences are made more homologous to human germline consensus sequence. With the exception of the Nanobody "hallmark" residues, specific amino acids in the framework regions that differ between the Nanobody and a human germline consensus sequence are altered to the human counterpart in such a way that the protein structure, activity and stability are preferably kept intact.

In this case, after an alignment with the human germline V gene database, DP51 was identified as having the highest homology with SEQ ID NO: 58. All possible permutations were elaborated in view of altering the parental Nanobody sequence more conform to the human DP51 germline consensus sequence, while keeping preferably the other Nanobody characteristics intact or these characteristics are even ameliorated.

Eventually a total of 12 amino acid residues were introduced into SEQ ID NO: 58: 1E, 14P, 27F, 29F, 40A, 49S, 73N, 75K, 78L, 82aN, 83R and 108L. Notably, Q27F and S29F are part of CDR1, but did not affect binding (cf. SEQ ID NO: 1; data not shown).

Example 3: Reducing Binding of Pre-Existing Antibodies 3.1 Experimental Part

The human samples used in Example 3.2 below were either obtained from commercial sources or from human volunteers (after all required consents and approvals were obtained) and were used in according with the applicable legal and regulatory requirements (including but not limited to those regarding medical secret and patient privacy).

In Example 3.2 below, unless explicitly indicated otherwise, the binding of pre-existing antibodies that are present in the samples used (i.e. from healthy volunteers, rheumatoid arthritis (RA) patients and SLE patients) to the Nanobodies tested was determined using ProteOn as follows:

Nanobodies were captured either on serum albumin or via a FLAG3 tag using monoclonal anti-FLAG M2.

In case of binding of pre-existing antibodies on Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 μl/min) and HSA was injected at 10 μg/ml in ProteOn Acetate buffer pH4.5 (flow rate 100 μl/min) to render immobilization levels of approximately 3200 RU. After immobilization, surfaces were deactivated with ethanolamine HCl (flow rate 30 μl/min). Nanobodies were injected for 2 minutes at 45 μl/min over the HSA surface to render a Nanobody capture level of approximately 200 RU. The samples containing pre-existing antibodies were centrifuged for 2 minutes at 14,000 rpm and supernatant was diluted 1:10 in PBS-Tween20 (0.005%) before being injected for 2 minutes at 45 μl/min followed by a subsequent 400 seconds dissociation step. After each cycle (i.e. before a new Nanobody capture and blood sample injection step) the HSA surfaces were regenerated with a 2 minute injection of HCl (100 mM) at 45 μl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

In case of binding of pre-existing antibodies on FLAG-tagged Nanobodies captured on monoclonal anti-FLAG M2 (Sigma) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 μl/min) and anti-FLAG M2 mAb was injected at 10 μg/ml in ProteOn Acetate buffer pH4.5 (flow rate 100 μl/min) to render immobilization levels of approximately 4000 RU. After immobilization, surfaces were deactivated with ethanolamine HCl (flow rate 30 μl/min). Nanobodies were injected for 2 minutes at 45 μl/min over the anti-FLAG M2 surface to render a Nanobody capture level of approximately 100 RU. To reduce non-specific binding of the blood samples to the anti-FLAG M2 surface 100 nM 3×FLAG peptide (Sigma) was added to the blood samples. The samples containing pre-existing antibodies were centrifuged for 2 minutes at 14,000 rpm and supernatant was diluted 1:10 in PBS-Tween20 (0.005%) before being injected for 2 minutes at 45 μl/min followed by a subsequent 600 seconds dissociation step. After each cycle (i.e. before a new Nanobody capture and blood sample injection step) the anti-FLAG M2 surfaces were regenerated with a 10 seconds injection of Glycine pH1.5 (10 mM) at 150 μl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-anti-FLAG M2 dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

3.2: Introducing the Mutations of the Invention in Reference A (SEQ ID NO: 1) Leads to a Reduction in Binding by Pre-Existing Antibodies.

The following amino acid sequences were used: SEQ ID NO: 58 (with Q108L mutation), Reference A, Reference A (L11V, V89L)-Ala, Reference A (L11V, A74S, V89L)-Ala and Reference A (L11V, S49A, V89L)-Ala, all with an N-terminal HIS6-FLAG3 tag (SEQ ID NO: 42). These Nanobodies were tested for binding by pre-existing antibodies that are present in the samples from 96 serum samples from healthy human volunteers. The compounds were captured using the FLAG-tag and binding was measured using ProteOn according to the protocol given in the preamble to this Experimental Part.

The results are shown in FIG. 6. FIG. 7 lists the results for each of the samples that forms one of the data points in FIG. 6.

It can be seen that for most of the 96 samples tested, introducing the mutations according to the invention leads to a reduction in pre-existing antibody binding, with the degree of reduction generally being dependent on the level to which the pre-existing antibodies in each sample were capable of binding to Reference A.

Example 4: Chemical Stability Assessment

The chemical stability of the various humanized and/or optimized Nanobodies were assessed via forced oxidation and temperature stress tests.

A new reference compound was made, i.e. A016600015 (SEQ ID NO: 61). This new reference compound is more conform to presumed clinical candidates, and thus enables a better assessment of the impact of mutations. A016600015 is identical to Reference A (SEQ ID NO: 1) except for a C-terminal Alanine and an Aspartate at amino acid residue 1. The C-terminal Ala was introduced in view of reducing PEAs according to WO 2012/175741 (cf. Example 3). The N-terminal Glutamate was substituted for an Aspartate at amino acid residue 1 after an assessment of pyroglutamate formation. The activity of the new reference A016600015 was virtually identical to Reference A (data not shown). This new compound A016600015 is further used throughout the examples as the reference compound unless indicated otherwise.

Based on the results of Example 3, anti-PEA mutations L11V and V89L were introduced (amongst others) compared to new reference compound A016600015, resulting in A016600018 (SEQ ID NO: 37) and A016600019 (SEQ ID NO: 38). The sequences are depicted in FIG. 3.

4.1 Forced Oxidation Stability

Nanobody samples of the reference compound A016600015 (1 mg/ml) were subjected for four hours at RT and in the dark to 10 mM $H_2O_2$ in PBS, in parallel with control samples without $H_2O_2$, followed by buffer switch to PBS using Zeba desalting spin columns (0.5 ml) (Thermo Scientific). Stressed and control samples were then analyzed by means of RPC on a Series 1200 or 1290 machine (Agilent Technologies) over a Zorbax 300SB-C3 column (Agilent Technologies) at 70° C. Oxidation of Nanobodies was quantified by determination of % peak area of pre-peaks occurring as a result of oxidative stress, compared to the main protein peak.

No variants were observed in the oxidation stressed samples of the reference compound A016600015 (data not shown).

4.2 Temperature Stress Stability

Nanobody samples (1-2 mg/ml) were stored in PBS for four weeks at −20° C. (negative control) 25 and 40° C. After this incubation period, Nanobodies were digested with Trypsin or LysC. Peptides of stressed and control samples were then analyzed by means of RPC on a Series 1290 machine (Agilent Technologies) over an Acquity UPLC BEH300-C18 column (Agilent Technologies) at 60° C. The column is coupled to a Q-TOF mass spectrometer (6530 Accurate Mass Q-TOF (Agilent)). Integration of the peptide map UV 214 nm or EIC (Extracted Ion Chromatogram) chromatograms allow for reliable quantification of a given modification.

Only at 40° C. some isomerisation and pyro-glutamate variants were observed. Notably, amino acid residue 54D, which is located in the environmentally exposed CDR2 and potentially amenable to isomerisation, demonstrated virtually no isomerisation. Isomerisation of amino acid residue 1 was inappreciable if the Nanobodies were kept at or below 25° C. for extended periods of time.

4.3 Melting Temperatures of via Thermal Shift Assay (TSA)

The melting temperature of a Nanobody is a measure of its biophysical stability.

The melting temperatures of various Nanobodies were assessed via a thermal shift assay (TSA) essentially according to Ericsson et al. 2006 (Anals of Biochemistry, 357: 289-298). In short, 5 μl of purified monovalent Nanobodies (800 μg/ml) were incubated with 5 μL of the fluorescent probe Sypro Orange (Invitrogen, 56551) (final concentration 10×) in 10 μL of buffer (100 mM phosphate, 100 mM borate, 100 mM citrate, 115 mM NaCl, buffered at different pH ranging from 3.5 to 9). The samples were heated in a LightCycler 48011 machine (Roche), from 37 to 99° C. at the rate of 4.4° C./s, after which they were cooled down to 37° C. at a rate of 0.03° C./s. Upon heat-induced unfolding, hydrophobic patches of the proteins are exposed to which the Sypro Orange binds resulting in an increase in fluorescence intensity (Ex/Em=465/580 nm). The inflection point of the first derivative of the fluorescence intensity curve serves as a measure of the melting temperature (Tm).

The reference compound A016600015 (SEQ ID NO: 61) was compared with A016600018 (SEQ ID NO: 37) and A016600019 (SEQ ID NO: 38). In contrast to A016600015, both A016600018 and A016600019 comprise the anti-PEA mutations L11V and V89L according to Example 3.

The results are depicted in Table 4.3

TABLE 4.3

| NB ID | anti-PEA | amount (μg) | Tm (° C.) pH 7 |
|---|---|---|---|
| A016600015 | — | 87 | 59 |
| A016600018 | L11V V89L | 38 | 59 |
| A016600019 | L11V V89L | 16 | 56 |

As can be seen from Table 4.3, the anti-PEA mutations appeared to have either no effect on the Tm (A016600018) or a negative effect on the Tm (A016600019). Notably, the difference between A016600018 ("00018") and A016600019 ("00019") is 78L and 78V, respectively. Overall, any effects of this difference in amino acid residue 78 were shown to be insignificant compared to the introduction of the anti-PEA mutations (see also below).

When producing, it was also seen that the expression of these variants comprising the anti-PEA mutations was suboptimal. This was further quantified using the method of Example 1.

The results are shown in Table 4.3.

Indeed, the amount retrievable from both variants comprising the anti-PEA mutations was about 2-fold lower (A016600018) or even 4-fold lower (A016600019) than from the reference Nanobody. This came as a complete surprise to the inventors, since the introduction of these anti-PEA mutations L11V and V89L did not result in such a serious drop in the ability to recover Nanobodies before as determined for any other clone.

4.4 Protease Stability

It is intended that the TNF-inhibitors may eventually be administered orally. However, the stomach and intestines constitute a naturally hostile environment since they are designed for the enzymatic break down and absorption of partially solid foods. In general, proteolysis of a protein substrate can only occur if 8-10 amino acid residues within the polypeptide chain can bind and adapt to the specific stereochemistry of the protease's active site (Fontana et al. 2004 Acta Biochim Pol, 51, 299-321). Hence, the susceptibility to enzymatic cleavage depends largely on the physical properties of the substrate.

K64, S94, P95 and R96, resulting in variant A016600013; SEQ ID NO: 65.

However, mutating these sites resulted in reduced expression levels and intracellular accumulation of the variant (A016600013; SEQ ID NO: 65). In fact, when amino acid residue 38 was back mutated, which improved expression, the resulting variant (A016600014; SEQ ID NO: 66) was completely contrary to expectations more protease sensitive than the reference compound A016600015 (data not shown). Hence, it was decided to not mutate these positions in the reference compound and Nanobodies under study, i.e. A016600018 and A016600019.

A summary of the results is depicted in Table 4.4.

TABLE 4.4

| | | | % intact Nanobody after incubation (hours) with proteases | | | | | | | |
|---|---|---|---|---|---|---|---|---|---|---|
| | | | Trypsin | | | | Chymotrypsin | | | |
| Nanobody | L11 | V89 | 0 h | 2 h | 4 h | ON | 0 h | 2 h | 4 h | ON |
| A016600015 | . | . | 100 | 95 | 99 | 79 | 100 | 16 | 18 | 15 |
| A016600019 | V | L | 100 | 83 | 91 | 78 | 100 | 27 | 39 | 31 |
| A016600018 | V | L | 100 | 89 | 85 | 63 | 100 | 38 | 31 | 14 |

In order to identify potential protease degradation sites and design more stable variants, the present inventors set out to identify the trypsin and chymotrypsin cleavage sites according to standard methods.

The predicted protease sites ("P") of SEQ ID NO: 58 and new reference compound A016600015 ("00015") are depicted as ("X") in FIG. 8A for both trypsin and chemotrypsin.

From this figure it can already be concluded that:
CDR3 comprises 9 potential protease cleavage sites.
humanization mutation Q75K (VH3-DP51) introduced a potential trypsin cleavage site.
humanization mutation K73N (VH3-DP51) eliminated a potential trypsin cleavage site.
the anti-PEA mutations L11V and V89L were neutral in this regard, i.e. these mutations did not introduce or eliminate potential protease cleavage sites, as expected.

In order to assess the predicted protease cleavage sites in a more in vivo setting, the Nanobodies were digested with trypsin and chymotrypsin. In particular, anti-TNFα Nanobodies were incubated in 10% trypsin or α-chymotrypsin solutions. Two µg Nanobody was submitted to tryptic digest for 2 h, 4 h and overnight at 37° C., or chymotryptic digest for 2 h, 4 h or overnight at 25° C. The proteolytic reaction was stopped by addition of TFA (0.1% final). Reaction mixtures were either analysed via RPC LC-MS or separated on a SDS PAGE gel and stained with Coomassie blue. Using ImageQuant (GE) the amount of intact material was calculated and normalised to 0 h as reference time point.

An exemplary result of a tryptic digest on a Coomassie stained SDS PAGE gel is provided in FIG. 8B. An exemplary result of a tryptic digest analysis via RPC LC-MS is provided in FIG. 8C. The experimentally ("E") confirmed cleavage sites are depicted in FIG. 8A as trypsin ("E") and chemotrypsin ("E").

From FIG. 8A it is clear that the number of actual cleavage sites is reduced. Nevertheless, various tryptic and chemotryptic recognition sites remain.

In order to optimize trypsin resistance, 5 positions were selected in order to engineer one optimized variant: R38, Example 5: Stability in Intestinal Fluids Derived from a SHIME Model To investigate the stability of the anti-TNFα Nanobodies in the human GI tract, the Nanobodies were incubated in 5 different fluids derived from a SHIME (Simulator of Human Intestinal Microbial Ecosystem), representing the human gastrointestinal tract (GI). The SHIME model is a scientifically validated dynamic model of the complete gastrointestinal tract, which is used to study physicochemical, enzymatic and microbial parameters in the gastrointestinal tract in a controlled in vitro setting.

The SHIME model consists of five reactors which sequentially simulate the stomach (acid conditions and pepsin digestion), small intestine (digestive processes) and the 3 regions of the large intestine, i.e. the ascending ("A"), transverse ("T") and descending colon ("D") (microbial processes). Careful control of the environmental parameters in these reactors allowed complex and stable microbial communities which are highly similar in both structure and function to the microbial community in the different regions of the human colon (see FIG. 9). All GI fluids were provided by ProDigest (Technologiepark 4, 9052 Zwijnaarde, Belgium). The anti-TNF Nanobodies were tested for a maximum period of 39 hours in the GI-fluids. After the incubation in the GI-fluids, stability of the Nanobodies was determined via functionality testing in a competition ELISA. The Nanobodies were tested at a fixed concentration of 100 µg/ml at 37° C. in 5 different GI fluids in the SHIME model. At different time-points samples were taken and stored in the −20° C. with or without the addition of protease inhibitors, according to the schedule in Table 5.1. The samples were transferred to coated ELISA plates and subsequently tested in the competition ELISA. In brief, A016600015 was coated at a concentration of 1 µg/ml in PBS. After blocking, a fixed concentration of 0.3 nM biot-hTNFa together with a titration series of the variants in the different GI fluids was added. Detection was performed with extravidin-HRP.

TABLE 5.1

Incubation schedule

| Fluid | Time-points |
|---|---|
| SI Fasted | 0, 1, 2, 4, 6, 8 h* |
| SI Fed | 0, 1, 2, 4, 6, 8 h* |
| Colon A | 0, 1, 2, 4, 8, 15, 20, 24 h |
| Colon T | 0, 1, 2, 4, 8, 15, 20, 24, 39 h |
| Colon D | 0, 1, 2, 4, 8, 15, 20, 24, 32 h |
| PBS | 0, 1, 2, 4, 6, 8, 15, 20, 24, 32 h |

*after incubation addition of 1 mg/ml Pefabloc and 1 µM Pepstatin (protease inhibitors)

An exemplary result in colon "T" is provided in Table 5.2

TABLE 5.2

| | | 0 h | 1 h | 2 h | 4 h | 8 h | 15 h | 20 h | 24 h | 39 h |
|---|---|---|---|---|---|---|---|---|---|---|
| 00015 | IC50 | 7.3E−10 | 5.0E−10 | 6.4E−10 | 6.2E−10 | 9.7E−10 | 1.3E−09 | 1.9E−09 | 2.8E−09 | 2.0E−08 |
| | ratio | 1.00 | 0.69 | 0.88 | 0.85 | 1.34 | 1.72 | 2.56 | 3.88 | 27.41 |
| | % | 100% | 145% | 113% | 117% | 75% | 58% | 39% | 26% | 4% |
| 00018 | IC50 | 5.7E−10 | 5.5E−10 | 6.9E−10 | 1.2E−09 | 2.8E−09 | 9.5E−09 | 3.2E−08 | 4.2E−08 | 6.2E−07 |
| | ratio | 1.00 | 0.97 | 1.22 | 2.19 | 4.96 | 16.68 | 55.58 | 73.79 | 1097.18 |
| | % | 100% | 103% | 82% | 46% | 20% | 6% | 2% | 1% | 0% |
| 00019 | IC50 | 5.0E−10 | 4.7E−10 | 4.5E−10 | 9.1E−10 | 7.2E−10 | 1.7E−09 | 3.0E−09 | 5.2E−09 | 4.1E−08 |
| | ratio | 1.00 | 0.93 | 0.89 | 1.81 | 1.43 | 3.36 | 6.02 | 10.32 | 82.22 |
| | % | 100% | 108% | 112% | 55% | 70% | 30% | 17% | 10% | 1% |

Based on the results with fluids derived from the different SHIME compartments, the stability evaluation allows a ranking of the Nanobodies representing the stability in all GI compartments: 00015>00019>00018.

Collectively, eliminating protease cleavage sites appears to have no positive effect, such as on stability and protease sensitivity of this family of Nanobodies. The introduction of anti-PEA mutations L11V and V89L in A16600015 appear to have a negative effect on the stability of this particular Nanobody.

Example 6: Stabilized Variants

Since eliminating the protease cleavage sites did not result in the anticipated results, the inventors further set out elaborate anti-TNF-α variants, which would inherently be more stable but in which the humanization and anti-PEA mutations were preferably not compromised. This required an unconventional approach in view of various amino acid residues displaying mutually exclusive characteristics, such as humanization versus protease stability versus affinity.

6.1 Internal Cysteine Bond and Elimination of CDR3 Chemotrypsin Cleavage Site

Located in CDR3 and potentially affecting the binding properties, it was nonetheless decided to construct a variant in which the amino acid residue Y100d, which is a chemotrypsin cleavage site, was eliminated by an Y100dL substitution (A016600046 100dL; SEQ ID NO: 62). Variant A016600045 (SEQ ID NO: 69) was engineered to assess the impact of the tyrosine on position 100d of CDR3 further.

In addition, the inventors hypothesized that variants could be engineered which would be inherently stable via the introduction of an intradomain disulfide bond (cf. Wozniak-Knopp et al. 2012 PLoS One. 2012; 7(1): e30083). This would require the introduction of two cysteines residues which then should pair to form a cystine. After resolving the protein structure of the Nanobody and its interaction with the target TNF-α via crystallization studies (data not shown), the inventors decided to mutate amino acids S49C and 169C mutations for introducing an intradomain disulfide bond, although amino acid residue S49 is adjacent to CDR2, and was introduced in view of humanization purposes (corresponding to human germline DP51, see Example 2). The new variant comprising S49C, 169C and Y100dL is annotated A016600052 (SEQ ID NO: 63).

In order to assess the influence of amino acid position 49 in depth, this amino acid residue was mutated to an alanine. Notably, this mutation at position 49 would correspond to the—albeit different—human germline IgHV3-IgHJ. All of the new variants A016600046 (SEQ ID NO: 62), A016600016 (SEQ ID NO: 36), A016600020 (SEQ ID NO: 39) and A016600021 (SEQ ID NO: 40) comprise A49.

In addition, in variant A016600020 (SEQ ID NO: 39) the positions D60A, E61D and P62S were evaluated in view of physical stability. Amino acid residues A60, D61 and S62 are located adjacent to the experimentally confirmed chymotrypsin cleavage site Y58 and within the CDR2 according to Kabat, which implies a high risk of potency loss.

Furthermore, a protease cleavage site was accidently introduced by the humanizing mutation Q75K. Without being bound by any theory, the inventors hypothesized that changing the adjacently located amino acid residue A74S would potentially affect both humanization as well as protease sensitivity, but only to a degree, i.e. it was hoped for that both humanization and the protease sensitivity were diminished to an acceptable degree. Variants comprising S74 are A016600016 ("00016"), A016600020 ("00020"), A016600021 ("00021"), A016600046 ("00046") and A016600052 ("00052") (SEQ ID NO:s 36, 39, 40, 62 and 63, respectively). The comparator variant was A016600038 ("00038"; SEQ ID NO: 64), which is identical to A016600021 (SEQ ID NO: 40), but with 74S instead of 74A.

The resulting sequences are provided in FIG. 3.

6.2 Characteristics of Stabilized Variants

Next, these variants were assessed for various characteristics, essentially as set out in Examples 3 and 4.

In first instance, production of variants 00016, 00020 and 00021 was determined in *P. pastoris* according to Example 1.

A summary of the obtained results is provided in Table 6.2A.

TABLE 6.2A

| Nanobody | L11 | S49 | D60 | E61 | P62 | A74 | L78 | V89 | Amount (μg) | Tm at pH 7 (° C.) | Stability in GI fluid (ranking) |
|---|---|---|---|---|---|---|---|---|---|---|---|
| A016600021 | V | A | . | . | . | S | V | L | 332 | 65 | 1 |
| A016600016 | V | A | . | . | . | S | . | L | 499 | 65 | 2 |
| A016600020 | V | A | A | D | S | S | V | L | 374 | 75 | 3 |

From these results it can be seen that these mutations resulted in an increase in production of more than 4-5 times the production of the reference compound, which produced 87 μg (cf. Example 4.3), or even more 20-30 than the closely related variants 00018 and 00019.

Next, the thermal stability of these variants was determined according to Example 4.3. A summary of the obtained results is also provided in Table 6.2A.

Not only the production increased dramatically, but also the thermal stability increased unexpectedly with 5-16° C. compared to the reference compound, but even up to 16-19° C. compared to the more closely related variants 00018 and 00019.

Unexpectedly, amino acid residue A49 obviates the influence of the anti-PEA amino acid residues V11 and L89 on production and stability.

Various variants of Example 6.1 were assessed together in the GI fluids derived from the SHIME model according to Example 5.

A summary of the resulting activity at the end of the incubation period under various conditions of A016600021, A016600038, A016600046 and A016600052 is provided in Table 6.2B. Incubation in PBS confirmed the inherent stability of the Nanobodies (data not shown).

Notably, variant A016600039 (SEQ ID NO: 68) which is identical to variant 00040 (SEQ ID NO: 67) but for A74S, showed that S74 was consistently less stable than A74 in the SHIME model.

Based on all results including the results with fluids derived from the different SHIME compartments, an overall stability evaluation allows a ranking of the Nanobodies representing the stability in all GI compartments: 00021>00016>00020>00040>00015>00019>00018.

Hence, the anti-PEA mutations L11V and V89L in A16600015 appear to have a negative effect on the stability of this particular Nanobody, which could be alleviated by 49A, but not by 49C-69C. Moreover, in Nanobodies comprising anti-PEA mutations L11V and V89L, the amino acid residue 74S was beneficial to stability in the SHIME model.

6.3 A016600021 has Favourable Characteristics (over A016600039 and A016600040)

For oral administration it is believed that high dosing may be required next to the stability. In order to have acceptable costs, the candidate is preferably produced at high amounts, purified without considerable loss and formulated at high concentration. Hence, the inventors set out experiments to test these parameters.

First, the inventors set out to compare the expression levels A016600039 and A016600040 with A016600021.

TABLE 6.2B

| | C/C0 vs time in h | | | | | | | |
|---|---|---|---|---|---|---|---|---|
| | CD colon A | CD colon D | CD colon T | SI fasted* | SI fed* | UC2 colon A | UC2 colon D | UC2 colon T |
| A016600021 | 66 | 58 | 76 | 65 | 31 | 86 | 57 | 71 |
| A016600038 | 48 | 41 | 47 | 60 | 33 | 77 | 50 | 59 |
| A016600046 | 47 | 29 | 62 | 52 | 24 | 92 | 59 | ≥100 |
| A016600052 | 41 | 49 | 40 | ND | ND | 64 | 43 | 55 |
| A016600039 | 38 | 26 | 39 | 23 | 20 | 78 | 20 | 55 |
| A016600040 | 38 | 40 | 19 | 67 | 24 | 91 | 83 | 63 |
| A016600045 | 85 | ≥100 | 49 | 60 | 26 | 68 | 41 | ≥100 |

*diseased;
ND is not determined;
CD is Crohn's Disease;
UC is ulcerative colitis The variants A016600046 Y100dL (SEQ ID NO: 62) in which a protease cleavage site was removed and variant A016600052 (SEQ ID NO: 63), which was further stabilized via an intradomain cysteine bond did not provide any improvements in this regard. Notably, the IC50 of variants 00046 and 00052 increased 2-5 times compared to 00021 (1.13 nM and 3.56 nM, respectively compared to 0.67 nM) because of the mutation in CDR3.

The SHIME results essentially confirmed and extended the results of the Tm and production. In addition, the SHIME model revealed that variant 00021 (SEQ ID NO: 40) is consistently more stable than variant A016600040 ("00040"; SEQ ID NO: 67) and variant 00038 (SEQ ID NO: 64), which is indicative for the positive contribution of a Serine at position 74.

As can be seen in FIG. 11, the expression of A016600039 (SEQ ID NO: 68) was considerably lower than the expression levels of A01660021 (SEQ ID NO: 40) and A016600040 (SEQ ID NO: 67). These results were also quantified via AKTAmicro, of which the results are depicted in the Table 6.3

TABLE 6.3

| Clone | Yield Aktaμ (g/L cell free medium) |
|---|---|
| A016600021 | 6.3 |
| A016600039 | 0.49 |
| A016600040 | 2.3 |

Regarding the manufacturability of A016600021 versus A016600040, both were tested on maximal solubility during concentration of fermentation broth. The maximal solubility in clarified fermentation broth is only 30 g/L for A016600040 (vs >75 g/L for A016600021). In addition, major losses were encountered during further purification of A016600040.

Hence, in addition to the stability, A016600021 has also—unexpectedly—favourable production and purification characteristics over A016600039 and A016600040.

Based on the advantageous stability, expression and purification characteristics, the inventors focussed on A016600021, of which solubility was determined. To a complete surprise of the inventors, A016600021 was soluble to an unprecedented 200 mg/ml in H$_2$O.

Example 7: Stabilized Variants Outperform Benchmarks

The variants A016600021 (SEQ ID NO: 40), A016600038 (SEQ ID NO: 64) and A016600045 (SEQ ID NO: 69) were assessed for binding to membrane bound human TNF (mTNF) in a competition assay with Enbrel (Etanercept), a TNF-R2 based anti-TNF therapeutic agent. Thereto a cell line stably expressing a non-cleavable form of human TNF was generated by transfection of HEK293H cells with a eukaryotic expression vector encoding the human TNF R77T/S78T variant (termed HEK293H-mTNF), as previously described (Harashima et al., 2001 J Immunol 166:130-136). After selection by co-expression of the puromycin resistance gene, sorting of individual mTNF expressing cells was performed via FACS (BD FACS Aria) upon staining of the cells with Remicade (Infliximab) and secondary Goat F(ab')2 Anti-Human IgG, Mouse ads-PE. Constitutive expression of membrane bound TNF on the selected individual clones was confirmed by flow cytometry (BD FACS Array).

At first instance, binding of Enbrel to mTNF on these cells was evaluated. Thereto 5·10$^5$ cells of a single HEK293H-mTNF clone were seeded in round bottom 96 well plates and directly incubated with different concentrations of Enbrel diluted in FACS buffer (PBS supplemented with 10% FBS and 0.05% Sodium Azide) for 90 minutes at 4° C. Cells were washed with FACS buffer and stained with secondary Goat F(ab')2 Anti-Human IgG, Mouse ads-PE antibody for 30 minutes at 4° C. After washing and incubation of the cells in FACS buffer in presence of the dead stain TO-PRO-3 Iodide, binding of Enbrel to mTNF on viable HEK293H-mTNF cells was measured by readout on BD FACS Array. From the obtained dose response curve EC30 and EC90 values of Enbrel for binding to mTNF were defined as being respectively 0.02 nM and 0.2 nM. Both concentrations were later applied in the competition assay with TNF-targeting Nanobodies.

To evaluate mTNF binding of A016600021, A016600038 and A016600045, a competition experiment with Enbrel at fixed EC30 and EC90 concentrations was setup. Potency of anti-TNF Nanobodies was compared with the benchmark compound Cimzia (certolizumab pegol). Additionally an irrelevant Nanobody (IRR00027) was included as a negative control. In this assay, identical conditions as described above for Enbrel binding were applied, except for the first incubation step which in this experiment involves co-treatment of the cells with a fixed concentration of Enbrel (EC30 or EC90) in combination with different concentrations of the anti-TNF Nanobodies or Cimzia ranging from 300 nM to 12.5 pM. Readout on BD FACS Array determined binding of Enbrel on HEK293H-mTNF cells which was clearly reduced upon co-treatment with increasing concentrations of Nanobodies as well as with Cimzia indicating competition of the anti-TNF agents with Enbrel for binding to mTNF. IC50 values of the anti-TNF agents were determined as indicated in Table 7.

TABLE 7

|  | Enbrel (EC30: 0.02 nM) | Enbrel (EC90: 0.2 nM) |
| --- | --- | --- |
| A016600021 | 0.43 nM | 0.65 nM |
| A016600038 | 0.43 nM | 0.70 nM |
| A016600045 | 0.54 nM | 0.76 nM |
| Cimzia | 7.9 nM | 4.8 nM |

The obtained results demonstrate that A016600021, A016600038 and A016600045 have a 6-7 times better potency than Cimzia at EC90 and a stunning 15-18 times better potency than Cimzia at EC30. The stabilized variants have a comparable potency to compete with Enbrel for mTNF binding.

In a competition FACS it was demonstrated that the Nanobodies could also completely inhibit the binding of Enbrel to mTNF. This would be indicative for a superior suitability as a medicament for oral application. In contrast, high concentrations of Cimzia resulted only in partial blocking of Enbrel binding (FIG. 10).

The entire contents of all of the references (including literature references, issued patents, published patent applications, and co-pending patent applications) cited throughout this application are hereby expressly incorporated by reference, in particular for the teaching that is referenced hereinabove.

TABLE A

| Reference A and its CDRs and PMP6C11 | | |
| --- | --- | --- |
| SEQ ID NO | Description | Sequence |
| 58 | NC55TNF-NC7 (PMP6C11). WO06/122786: SEQ ID NO: 125 | QVQLVESGGGLVQAGGSLRLSCTASGQTSSTADMGWFRQPPGKGR EFVARISGIDGTTYYDEPVKGRFTISRDKAQNTVYLQMDSLKPED TAVYYCRSPRYADQWSAYDYWGQGTQVTVSS |
| 59 | WO2015/173325 SEQ ID NO: 345 | EVQLVESGGGVVQPGGSLRLSCTASGFTFSTADMGWFRQAPGKGR EFVSRISGIDGTTYYDEPVKGRFTISRDNAKNTLYLQMNSLRPED TALYYCRSPRYADQWSAYDYWGQGTLVTVSS |

TABLE A-continued

Reference A and its CDRs and PMP6C11

| SEQ ID NO | Description | Sequence |
|---|---|---|
| 1 | Reference A: | EVQLVESGGGLVQPGGSLRLSCTASGFTFSTADMGWFRQAPGKGREFVSRISGIDGTTYYDEPVKGRFTISRDNAKNTLYLQMNSLRPEDTAVYYCRSPRYADQWSAYDYWGQGTLVTVSS |
| 2 | CDR1 (Kabat) | TADMG |
| 3 | CDR2 (Kabat) | RISGIDGTTYYDEPVKG |
| 4 | CDR3 (Kabat/Abm) | PRYADQWSAYDY |
| 5 | CDR1 (Abm) | GFTFSTADMG |
| 6 | CDR2 (Abm) | RISGIDGTTY |
| 7 | CDR3 (Kabat/Abm) | PRYADQWSAYDY |

Note:
SEQ ID NO: 4 is identical to SEQ ID NO: 7

TABLE B

Possible combinations of amino acids at positions 11, 89, 110 and 112.

| | 11 | 89 | 110 | 112 | | 11 | 89 | 110 | 112 | | 11 | 89 | 110 | 112 | | 11 | 89 | 110 | 112 |
|---|---|---|---|---|---|---|---|---|---|---|---|---|---|---|---|---|---|---|---|
| COMBINATION | L | T | T | S | COMBINATION | V | T | T | S | | L | V | Q | S | | V | V | Q | S |
| | L | T | T | K | | V | T | T | K | | L | L | T | K | | V | L | T | S |
| | L | T | T | Q | | V | T | T | Q | | L | L | T | Q | | V | L | T | K |
| | L | T | K | S | | V | T | K | S | | L | L | K | S | | V | L | T | Q |
| | L | T | Q | S | | V | T | Q | S | | L | L | Q | S | | V | L | K | S |
| | L | V | T | K | | V | V | T | K | | | | | | | V | L | Q | S |
| | L | V | T | Q | | V | V | T | Q | | | | | | | | | | |
| | L | V | K | S | | V | V | K | S | | | | | | | | | | |

TABLE B-1

Possible combinations of amino acids at positions 11, 89, 110, 112, 49 and 74.

| | 11 | 89 | 110 | 112 | 49 | 74 | | 11 | 89 | 110 | 112 | 49 | | 11 | 89 | 110 | 112 | 74 |
|---|---|---|---|---|---|---|---|---|---|---|---|---|---|---|---|---|---|---|
| COMBINATION | L | T | T | S | A | S | COMBINATION | L | T | T | S | A | COMBINATION | L | T | T | S | S |
| | L | T | T | K | A | S | | L | T | T | K | A | | L | T | T | K | S |
| | L | T | T | Q | A | S | | L | T | T | Q | A | | L | T | T | Q | S |
| | L | T | K | S | A | S | | L | T | K | S | A | | L | T | K | S | S |
| | L | T | Q | S | A | S | | L | T | Q | S | A | | L | T | Q | S | S |
| | L | V | T | K | A | S | | L | V | T | K | A | | L | V | T | K | S |
| | L | V | T | Q | A | S | | L | V | T | Q | A | | L | V | T | Q | S |
| | L | V | K | S | A | S | | L | V | K | S | A | | L | V | K | S | S |
| | L | V | Q | S | A | S | | L | V | Q | S | A | | L | V | Q | S | S |
| | L | L | T | K | A | S | | L | L | T | K | A | | L | L | T | K | S |
| | L | L | T | Q | A | S | | L | L | T | Q | A | | L | L | T | Q | S |
| | L | L | K | S | A | S | | L | L | K | S | A | | L | L | K | S | S |
| | L | L | Q | S | A | S | | L | L | Q | S | A | | L | L | Q | S | S |

TABLE B-2

Possible combinations of amino acids at positions 11, 89, 110, 112, 49 and 74.

| | 11 | 89 | 110 | 112 | 49 | 74 | | 11 | 89 | 110 | 112 | 49 | | 11 | 89 | 110 | 112 | 74 |
|---|---|---|---|---|---|---|---|---|---|---|---|---|---|---|---|---|---|---|
| COMBINATION | V | T | T | S | A | S | COMBINATION | V | T | T | S | A | COMBINATION | V | T | T | S | S |
| | V | T | T | K | A | S | | V | T | T | K | A | | V | T | T | K | S |

TABLE B-2-continued

Possible combinations of amino acids at positions 11, 89, 110, 112, 49 and 74.

| 11 | 89 | 110 | 112 | 49 | 74 |
|----|----|----|----|----|----|
| V | T | T | Q | A | S |
| V | T | K | S | A | S |
| V | V | T | K | A | S |
| V | V | T | Q | A | S |
| V | V | K | S | A | S |
| V | V | Q | S | A | S |
| V | L | T | S | A | S |
| V | L | T | K | A | S |
| V | L | T | Q | A | S |
| V | L | K | S | A | S |
| V | L | Q | S | A | S |
| V | T | Q | S | A | S |

| 11 | 89 | 110 | 112 | 49 |
|----|----|----|----|----|
| V | T | T | Q | A |
| V | T | K | S | A |
| V | V | T | K | A |
| V | V | T | Q | A |
| V | V | K | S | A |
| V | V | Q | S | A |
| V | L | T | S | A |
| V | L | T | K | A |
| V | L | T | Q | A |
| V | L | K | S | A |
| V | L | Q | S | A |
| V | T | Q | S | A |

| 11 | 89 | 110 | 112 | 74 |
|----|----|----|----|----|
| V | T | T | Q | S |
| V | T | K | S | S |
| V | V | T | K | S |
| V | V | T | Q | S |
| V | V | K | S | S |
| V | V | Q | S | S |
| V | L | T | S | S |
| V | L | T | K | S |
| V | L | T | Q | S |
| V | L | K | S | S |
| V | L | Q | S | S |
| V | T | Q | S | S |

TABLE C-1

Schematic representation of some compounds of the invention without a half-life extending ISVD.

[TNF binder of the invention]
[TNF binder of the invention]-X(n)
[TNF binder of the invention]-[TNF binder of the invention]
[TNF binder of the invention]-[TNF binder of the invention]-X(n)
[TNF binder of the invention]-[TNF2]
[TNF binder of the invention]-[TNF2]-X(n)
[TNF2]-[TNF binder of the invention]
[TNF2]-[TNF binder of the invention]-X(n)
[TNF binder of the invention]-[Targeting unit]
[Targeting unit]-[TNF binder of the invention]-
[TNF binder of the invention]-[Targeting unit]-X(n)
[TNF binder of the invention]-[TNF binder of the invention]-[Targeting unit]-X(n)

Legend:

"[TNF binder of the invention]" represents a TNF binder of the invention

"-" represents either a direct covalent linkage or a suitable linker, such as a 9GS, 15GS or 35GS linker "X(n)" represents a C-terminal extension as defined herein such as a single alanine residue.

"[TNF2]" represents a binding domain or binding unit (and in particular ISVD) against TNF different from the TNF binder of the invention.

"[Targeting unit]" represents a binding domain or binding unit (and in particular ISVD) that targets the compound of the invention to a specific cell, tissue or organ

TABLE C-2

Schematic representation of some compounds of the invention with a half-life extending ISVD.

[TNF binder of the invention]-[HLE]
[HLE]-[TNF binder of the invention]
[TNF binder of the invention]-[HLE]-X(n)
[HLE]-[TNF binder of the invention]-X(n)
[TNF binder of the invention]-[TNF binder of the invention]-[HLE]
[TNF binder of the invention]-[HLE]-[TNF binder of the invention]
[HLE]-[TNF binder of the invention]-[TNF binder of the invention]
[TNF binder of the invention]-[TNF binder of the invention]-[HLE]-X(n)
[TNF binder of the invention]-[HLE]-[TNF binder of the invention]-X(n)
[HLE]-[TNF binder of the invention]-[TNF binder of the invention]-X(n)
[TNF binder of the invention]-[TNF2]-[HLE]
[TNF binder of the invention]-[HLE]-[TNF2]
[HLE]-[TNF binder of the invention]-[TNF2]
[HLE]-[TNF2]-[TNF binder of the invention]
[TNF2]-[TNF binder of the invention]-[HLE]
[TNF2-[HLE]-[TNF binder of the invention]
[TNF binder of the invention]-[TNF2]-[HLE]-X(n)
[TNF binder of the invention]-[HLE]-[TNF2]-X(n)
[HLE]-[TNF binder of the invention]-[TNF2]-X(n)
[HLE]-[TNF2]-[TNF binder of the invention]-X(n)
[TNF2]-[TNF binder of the invention]-[HLE]-X(n)
[TNF2]-[HLE]-[TNF binder of the invention]-X(n)
[TNF binder of the invention]-[Targeting unit]-[HLE]
[Targeting unit]-[TNF binder of the invention]-[HLE]
[TNF binder of the invention]-[Targeting unit]-[HLE]-X(n)

TABLE C-2-continued

Schematic representation of some compounds of the invention with a half-life extending ISVD.

[HLE]-[Targeting unit]-[TNF binder of the invention]-[HLE]-X(n)

Legend:

"[TNF binder of the invention]" represents a TNF binder of the invention

"-" represents either a direct covalent linkage or a suitable linker, such as a 9GS, 15GS or 35GS linker "X(n)" represents a C-terminal extension as defined herein such as a single alanine residue.

"[HLE]" represents a half-life extending binding domain or binding unit (and in particular a half-life extending ISVD), such as an ISVD (and in particular Nanobody) against (human) serum albumin;

"[TNF2]" represents a binding domain or binding unit (and in particular ISVD) against TNF different from the TNF binder of the invention.

"[Targeting unit]" represents a binding domain or binding unit (and in particular ISVD) that targets the compound of the invention to a specific cell, tissue or organ

TABLE D

Serum albumin binding ISVD sequences ("ID" refers to the SEQ ID NO as used herein)

| Name | ID | Amino acid sequence |
|---|---|---|
| Alb8 | 70 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb23 | 71 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb129 | 72 | EVQLVESGGGVVQPGNSLRLSCAASGFTFSSFGMSWVRQAPGKGLEWVSSISGSGSDTLYADSVKGRFTISRDNAKTTLYLQMNSLRPEDTATYYCTIGGSLSRSSQGTLVTVSSA |
| Alb132 | 73 | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| Alb11 | 74 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| Alb11(S112K)-A | 75 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVKVSSA |
| Alb82 | 76 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |
| Alb82-A | 77 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA |
| Alb82-AA | 78 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA |
| Alb82-AAA | 79 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAAA |
| Alb82-G | 80 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSG |
| Alb82-GG | 81 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGG |
| Alb82-GGG | 82 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGGG |
| Alb92 | 83 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| Alb223 | 84 | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |

TABLE E

Various amino acid sequences ("ID" refers to the SEQ ID NO as used herein)

| Name | ID | Amino acid sequence |
|---|---|---|
| 5GS linker | 85 | GGGGS |
| 7GS linker | 86 | SGGSGGS |
| 8GS linker | 87 | GGGGCGGGS |
| 9GS linker | 88 | GGGGSGGGS |
| 10GS linker | 89 | GGGGSGGGGS |
| 15GS linker | 90 | GGGGSGGGGSGGGGS |
| 18GS linker | 91 | GGGGSGGGGSGGGGGGGS |
| 20GS linker | 92 | GGGGSGGGGSGGGGSGGGGS |
| 25GS linker | 93 | GGGGSGGGGSGGGGSGGGGSGGGGS |
| 30GS linker | 94 | GGGGSGGGGSGGGGSGGGGSGGGGSGGGGS |

TABLE E-continued

Various amino acid sequences ("ID" refers to the SEQ ID NO as used herein)

| Name | ID | Amino acid sequence |
|---|---|---|
| 35GS linker | 95 | GGGGSGGGGSGGGGSGGGGSGGGGSGGGGSGGGGS |
| 40GS linker | 96 | GGGGSGGGGSGGGGSGGGGSGGGGSGGGGSGGGGSGGGGS |
| G1 hinge | 97 | EPKSCDKTHTCPPCP |
| 9GS-G1 hinge | 98 | GGGGSGGGSEPKSCDKTHTCPPCP |
| Llama upper long hinge region | 99 | EPKTPKPQPAAA |
| G3 hinge | 100 | ELKTPLGDTTHTCPRCPEPKSCDTPPPCPRCPEPKSCDTPPPCPRCPEPKSCDTPPPCPRCP |

The invention claimed is:

1. An immunoglobulin single variable domain (ISVD) comprising SEQ ID NO: 40.

2. An immunoglobulin single variable domain (ISVD) consisting of SEQ ID NO: 40.

* * * * *